(12) United States Patent
Basstanie et al.

(10) Patent No.: US 11,446,260 B2
(45) Date of Patent: Sep. 20, 2022

(54) PHARMACEUTICAL COMPOSITION OF S-KETAMINE HYDROCHLORIDE

(71) Applicant: Janssen Pharmaceutica NV, Beerse (BE)

(72) Inventors: Esther D. G. Basstanie, Zandhoven (BE); Johanna Bentz, Newark, CA (US); Roger C. A Embrechts, Oud-Turnhout (BE); Nico Rudolph Niemeijer, Best (NL)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/221,950

(22) Filed: Dec. 17, 2018

(65) Prior Publication Data

US 2019/0117591 A1   Apr. 25, 2019

Related U.S. Application Data

(63) Continuation of application No. 14/211,874, filed on Mar. 14, 2014, now abandoned.

(60) Provisional application No. 61/791,237, filed on Mar. 15, 2013.

(51) Int. Cl.
| | |
|---|---|
| *A61K 31/135* | (2006.01) |
| *A61P 25/24* | (2006.01) |
| *A61K 9/00* | (2006.01) |
| *A61K 47/28* | (2006.01) |
| *A61K 31/575* | (2006.01) |
| *A61K 47/02* | (2006.01) |
| *A61K 31/136* | (2006.01) |

(52) U.S. Cl.
CPC .......... *A61K 31/135* (2013.01); *A61K 9/0043* (2013.01); *A61K 31/136* (2013.01); *A61K 31/575* (2013.01); *A61K 47/02* (2013.01); *A61K 47/28* (2013.01)

(58) Field of Classification Search
CPC .............................. A61K 31/135; A61P 25/24
See application file for complete search history.

(56) References Cited

U.S. PATENT DOCUMENTS

| | | |
|---|---|---|
| 4,994,467 A | 2/1991 | Zimmerman |
| 5,024,998 A | 6/1991 | Bodor |
| 5,543,434 A | 8/1996 | Weg |
| 6,017,961 A | 1/2000 | Flores et al. |
| 6,040,479 A | 3/2000 | Steiner et al. |
| 6,176,242 B1 | 1/2001 | Rise |
| 6,321,942 B1 | 11/2001 | Krampen et al. |
| 6,427,680 B1 | 8/2002 | Oechsel |
| 6,572,849 B2 | 6/2003 | Shahinian, Jr. |
| 6,599,883 B1 | 7/2003 | Romeo et al. |
| 7,273,889 B2 | 9/2007 | Mermelstein et al. |
| 7,687,080 B2 | 3/2010 | Wolicki |
| 7,745,665 B2 | 6/2010 | Gant et al. |
| 7,896,850 B2 | 3/2011 | Kronestedt et al. |
| 7,973,043 B2 | 7/2011 | Migaly |
| 8,785,500 B2 | 7/2014 | Charney et al. |
| 9,569,220 B2 | 2/2017 | Jacobs |
| 9,592,207 B2 | 3/2017 | Charney et al. |
| 10,098,854 B2 | 10/2018 | Drevets et al. |
| 2004/0138298 A1 | 7/2004 | Mermelstein et al. |
| 2004/0214215 A1 | 10/2004 | Yu et al. |
| 2004/0265364 A1 | 12/2004 | Ozturk et al. |
| 2005/0095277 A1 | 5/2005 | Ozturk et al. |
| 2006/0223788 A1 | 10/2006 | Cathcart |
| 2006/0276550 A1 | 12/2006 | Bhagwat |
| 2007/0256688 A1 | 11/2007 | Schuster et al. |
| 2007/0287753 A1* | 12/2007 | Charney ............... A61K 9/0019 514/647 |
| 2008/0171075 A1 | 7/2008 | Ozturk et al. |
| 2009/0306137 A1 | 12/2009 | Wolfgang et al. |
| 2011/0112131 A1 | 5/2011 | Holtman et al. |
| 2011/0306674 A1 | 12/2011 | Schiene et al. |
| 2012/0059666 A1 | 3/2012 | Kost et al. |
| 2012/0225949 A1 | 9/2012 | Papalos |
| 2013/0172361 A1 | 7/2013 | Fava et al. |
| 2013/0209585 A1 | 8/2013 | Kim |
| 2013/0236573 A1 | 9/2013 | Singh et al. |
| 2014/0079740 A1 | 3/2014 | Salama |
| 2014/0093592 A1 | 4/2014 | Singh et al. |
| 2014/0256821 A1 | 9/2014 | Charney et al. |
| 2015/0196501 A1 | 7/2015 | Erickson et al. |
| 2016/0074340 A1 | 3/2016 | Caers et al. |
| 2016/0175266 A1 | 6/2016 | Mermelstein et al. |
| 2016/0332962 A1 | 11/2016 | Chen et al. |

(Continued)

FOREIGN PATENT DOCUMENTS

| | | |
|---|---|---|
| AU | 2016203771 A1 | 6/2016 |
| CN | 103705909 A | 4/2014 |

(Continued)

OTHER PUBLICATIONS

Gomes et al., Neurotoxicity of Subarachnoid Preservative-Free S (+)-Ketamine in Dogs, 2011, Pain Physician, 14, pp. 83-90 (Year: 2011).*

Stevenson, C., Ketamine: A Review, 2005, Update in Anaesthesia, 20, pp. 25-29 (Year: 2005).*

Diazgranados et al, Rapid Resolution of Suicidal ideation After a Single Infusion of an N-Methyl-D Aspartate Antagonist in Patient With Treatment-Resistant Major Depressive Disorder, J Clin Psychiatry, 2010, pp. 1605-1611, vol. 71, Issue 12.

Diazgranados et al, A randomized add-on trial of an N-methyl-D-aspartate antagonist in treatment-resistant bipolar depression. Archives of general psychiatry 67, 2010, pp. 793-802.

Diaz, et al., Ineffectiveness of Repeated Intravenous Ketamine Infusions in Treatment-Resistant Depression After a Post-Ketamine Relapse:Time for a Rethink?, Journal of Clinical Psychopharmacology, 2018, pp. 1-2.

(Continued)

*Primary Examiner* — Jeffrey S Lundgren
*Assistant Examiner* — Chris E Simmons
(74) *Attorney, Agent, or Firm* — BakerHostetler

(57) ABSTRACT

The present invention is directed to an aqueous formulation of S-ketamine hydrochloride, preferably for nasal administration, wherein the formulation does not contain an antimicrobial preservative.

75 Claims, 3 Drawing Sheets

(56) References Cited

U.S. PATENT DOCUMENTS

| | | | |
|---|---|---|---|
| 2016/0338977 | A1 | 11/2016 | Singh et al. |
| 2017/0049780 | A1 | 2/2017 | Wainer et al. |
| 2017/0071242 | A1 | 3/2017 | Crespo et al. |
| 2017/0095429 | A1 | 4/2017 | Erickson et al. |
| 2018/0042936 | A1 | 2/2018 | Lombard |
| 2018/0296478 | A1 | 10/2018 | Salce et al. |

FOREIGN PATENT DOCUMENTS

| | | | |
|---|---|---|---|
| CN | 104798728 | A | 7/2015 |
| DE | 2062620 | | 7/1971 |
| DE | 4312016 | A1 | 10/1994 |
| DE | 19619665 | A1 | 11/1997 |
| DE | 102007009888 | A1 | 9/2008 |
| EP | 1103256 | A1 | 5/2001 |
| ES | 2484068 | A1 | 8/2014 |
| FR | 2739294 | A1 | 4/1997 |
| GB | 1330878 | A | 9/1973 |
| JP | 63-002932 | A | 1/1988 |
| NZ | 619257 | A | 7/2015 |
| WO | 94/23711 | A1 | 10/1994 |
| WO | 95/22965 | | 8/1995 |
| WO | 96/25925 | | 8/1996 |
| WO | 97/07750 | | 3/1997 |
| WO | 00/04875 | | 2/2000 |
| WO | 02/34293 | A2 | 5/2002 |
| WO | 2004/045601 | A1 | 6/2004 |
| WO | 2007/111880 | A2 | 10/2007 |
| WO | 2009/131794 | A1 | 10/2009 |
| WO | 2011/020061 | A2 | 2/2011 |
| WO | 2013/003669 | A2 | 1/2013 |
| WO | 2013/056229 | A1 | 4/2013 |
| WO | 2013/149102 | A1 | 10/2013 |
| WO | 2014/020155 | A1 | 2/2014 |
| WO | 2014/031975 | A1 | 2/2014 |
| WO | 2014/033680 | A1 | 3/2014 |
| WO | 2014/169272 | A1 | 10/2014 |
| WO | 2015/031410 | A1 | 3/2015 |
| WO | 2015/037248 | A1 | 3/2015 |
| WO | 2015/101693 | A1 | 7/2015 |
| WO | 2015/158854 | A1 | 10/2015 |
| WO | 2016/001599 | A1 | 1/2016 |
| WO | 2016/044150 | A1 | 3/2016 |
| WO | 2016/109427 | A1 | 7/2016 |
| WO | 2016/187491 | A1 | 11/2016 |
| WO | 2017/003935 | A1 | 1/2017 |
| WO | 2019/126108 | A1 | 6/2019 |

OTHER PUBLICATIONS

Diamond, et al., Ketamine infusions for treatment resistant depression: a series of 28 patients treated weekly or twice weekly in an ECT clinic, Journal of Psychopharmacology, 2014, pp. 536-544, vol. 28 Issue 6.

Dewilde, et al., The promise of ketamine for treatment-resistant depression: current evidence and future directions, Ann. N.Y. Acad. Sci, 2015, pp. 1-11.

Desseilles, et al., Assessing the Adequacy of Past Antidepressant Trails: A Clinician's Guide to the Antidepressant Treatment Response Questionnaire, J Clin Psychiatry, 2011, pp. 1152-1154, vol. 72 Issue 8.

Dennis Charney, Ketamine as a Rapid Treatment for Post-traumatic Stress Disorder (PTSD) (KetPTSD), ClinicalTrials.gov, Sep. 9, 2008, Ketamine, NCT00749203.

Denk, et al., Figure 1. Western Blot Analysis of Peripheral Blood Cells in a Study of (S)-Ketamine infusion for the treatment of Depressive Symptomsa, letters to the Editor, 2011, pp. 1-2.

Deisenhammer, et al., How Much Time Is Left for Intervention Between Consideration and Accomplishment of a Suicide Attempt?, J Clin Psychiatry, Mar. 25, 2008, pp. 19-24, vol. 70 Issue 1.

Debattista, et al., Acute Antidepressant Effects of Intravenous Hydrocortisone and CRH in Depressed Patients: A Double-Blind, Placebo-Controlled Study, Am J Psychiatry, Mar. 2, 2000, pp. 1334-1337, vol. 157 Issue 8.

Deakin, et al., PharmacoMRI and cognitive effects of the potential antidepressant AZD6765 compared with ketamine in untreated major depressive disorder, Affective disorders and antidepressants—Antidepressants (clinical), 2012, pp. S264-S264, Abstract.

DE102007009888 A1 English Translation, Sep. 2008; Translated Jan. 26, 2015.

DAWN., Drug Abuse Warning Network, 2011: National Estimates of Drug-Related Emergency Department Visits, National ED Estimates, 2011, pp. 1-100.

Davidson, et al., Anesthesia and neurotoxicity to the developing brain: the clinical relevance, Pediatric Anesthesia, 2011, pp. 716-721, vol. 21.

Danish University of Pharmaceutical Sciences., Nasal Administration of Sufentanil+Ketamine for Procedure-related Pain in Children, ClinicalTrials.gov, Jan. 12, 2010, Ketamine, NCT01047241.

Daly, et al., ESKETINTRD3003 ASCP Pipeline Presentation, Janssen Research & Therapeutic Area, May 29, 2018, pp. 1-21.

Daly, et al., Efficacy and Safety of Intranasal Esketamine Adjunctive to Oral Antidepressant Therapy in Treatment-Resistant Depression A Randomized Clinical Trial, JAMA Psychiatry, 2018, pp. 139-148, vol. 75 Issue 2.

D'sa, et al., Antidepressants and neuroplasticity, Bipolar Disorders, Feb. 1, 2002, pp. 183-194, vol. 4.

Cusin, et al., Long-Term Maintenance With Intramuscular Ketamine for Treatment-Resistant Bipolar II Depression, Am J Psychiatry, 2012, pp. 868-867, vol. 169 Issue 8.

Cusin, et al., Ketamine augmentation for outpatients with treatment-resistant depression: Preliminary evidence for two-step intravenous dose escalation, Australian & New Zealand Journal of Psychiatry, 2016, pp. 1-10.

Crosby, et al., Suicidal Thoughts and Behaviors Among Adults Aged graterthan & equal 18 Years—United States, 2008-2009, Centers for Disease Control and Prevention, Oct. 21, 2011, pp. 1-28, vol. 60 Issue 13.

Corwin Boake., Edouard Claparede and the Auditory Verbal Learning Test, Journal of Clinical and Experimental Neuropsychology, Oct. 18, 2000, pp. 286-292, vol. 22 Issue 2.

Corssen, et al., Computerized Evaluation of Psychic Effects of Ketamine, Anesthesia & Analgesia, 1971, pp. 397-401, vol. 50 Issue 3.

Corso, et al., Medical Costs and Productivity Losses Due to Interpersonal and Self-Directed Violence in the United States, Am J Prev Med, 2007, pp. 474-482, vol. 32 Issue 6.

Correll, et al., Two Case Studies of Patients with Major Depressive Disorder Given Low-Dose (Subanesthetic) Ketamine Infusions, Pain Medicine , 2006, pp. 92-95, vol. 7 Issue 1.

Correia-Melo, et al., Rapid infusion of esketamine for unipolar and bipolar depression: a retrospective chart review, Neuropsychiatric Disease and Treatment, Jun. 21, 2017, pp. 1627-1632, vol. 13.

Cornwell, et al., Synaptic Potentiation Is Critical for Rapid Antidepressant Response to Ketamine in Treatment-Resistant Major Depression, Biol Psychiatry, Mar. 29, 2012, pp. 555-561, vol. 72.

Compton, et al., Cognitive-Behavioral Psychotherapy for Anxiety and Depressive Disorders in Children and Adolescents: An Evidence-Based Medicine Review, J. Am. Acad. Child Adolesc. Psychiatry, Nov. 17, 2003, pp. 930-959, vol. 43 Issue 8.

Columbia University., Ketamine in the Treatment of Depression, ClinicalTrials.gov, Mar. 20, 2012, Ketamine, NCT01558063.

Clinical Trials.gov_NCT01998958, A Study to Evaluate the Safety and Efficacy of Intranasal Esketamine in Treatment-resistant Depression. ClinicalTrials.gov Identifier: NCT01998958. Jul. 14, 2014 [online], [Retrieved on Sep. 23, 2015]. Retrieved from the Internet: <URL: https://clinicaltrials.gov/archive/NCT01998958/2014_07_14> PDF File: p. 1-40. p. 1, Brief Summary, Phase, and the last para; and p. 2, para 1 and 3.

Clements, et al., Bioavailability, Pharmacokinetics, and Analgesic Activity of Ketamine in Humans, Journal of Pharmaceutical Sciences, 1982, pp. 539-542, vol. 71 Issue 5.

Clancy, et al., Translating Developmental Time Across Mammalian Species, Neuroscience, Apr. 11, 2011, pp. 7-17, vol. 105 Issue 1.

(56) References Cited

OTHER PUBLICATIONS

Cipriani, et al., Lithium in the prevention of suicide in mood disorders: updated systematic review and meta-analysis, BMJ, Jun. 27, 2013, pp. 1-13, vol. 346.

Cipriani, et al., Lithium in the Prevention of Suicidal Behavior and All-Cause Mortality in Patients With Mood Disorders: A Systematic Review of Randomized Trials, Am J Psychiatry, 2005, pp. 1805-1819, vol. 162 Issue 10.

Chu, et al., A Tool for the Culturally Competent Assessment of Suicide: The Cultural Assessment of Risk for Suicide (CARS) Measure, Psychological Assessment, Jan. 28, 2013, pp. 1-12.

Chong, et al., Development of a Sublingual/Oral Formulation of Ketamine for Use in Neuropathic Pain Preliminary Findings from a Three-Way Randomized, Crossover Study, Clin Drug Invest, 2009, pp. 317-324, vol. 5.

Children's Hospital Medical Center, Cincinnati., Pain Reduction With Intranasal Medications for Extremity Injuries (PRIME), ClinicalTrials.gov, May 20, 2016, ketamine, NCT02778880.

Cheung, et al., The use of antidepressants to treat depression in children and adolescents, CMAJ, Jan. 17, 2006, pp. 193-200, vol. 174 Issue 2.

Cheung, et al., Review of the efficacy and safety of antidepressants in youth depression, Journal of Child Psychology and Psychiatry, 2005, pp. 735-754, vol. 46 Issue 7.

Chen, et al., High prevalence of major depression among treatment-seeking ketamine-dependent patients, Abstracts/ Drug and Alcohol Dependence, 2017, pp. e39-e40, vol. 171.

Chen, et al., Effect of Low Dose of Ketamine on LeamingMemory Function in Patients Undergoing Electroconvulsive Therapy-A Randomized, Double-Blind, Controlled Clinical Study, Journal of ECT, 2016, pp. 1-7, Page Number.

Chen, et al, Determination of ketamine and metabolites in urine by liquid chromatography-mass spectrometry, Talanta, Jan. 16, 2007, pp. 1217-1222, vol. 72.

Chang, et al., The Depressed Patient and Suicidal Patient in the Emergency Department: Evidence-Based Management and Treatment Strategies, EB Medicine, Sep. 1, 2011, pp. 1-24, vol. 13 Issue 9.

Chang, et al, Metabolic Disposition on Tritium-Labeled Ketamine (KETALAR); c1-581 in Normal Human Subjects, Clinical Pharmacology, 1970, pp. 597-597.

Chang, et al, Major Depressive Disorder Induced by Chronic Ketamine Abuse: A Case Report, Primary Care Companion CNS Disorders, Jun. 23, 2016, pp. 1-3, vol. 18 Issue 3.

Chambers, et al., Developmental Neurocircuitry of Motivation in Adolescence: A Critical Period of Addiction Vulnerability, Am J Psychiatry, 2003, pp. 1041-1052, vol. 160 Issue 6.

Centre Hospitalier Universitaire De Ntmes., Effects of Ketamine in the Acute Phase of Suicidal Ideation (KETIS), ClinicalTrials.gov, Nov. 24, 2014, Ketamine, NCT02299440.

Celon Pharma SA., Safety and Pharmacokinetic Study of Inhaled Esketamine in Healthy Volunteers, Clinical Trials gov, Jan. 23, 2018, Esketamine, NCT03407872.

Cedars-Sinai Medical Center., Ketamine for Preventing Depression in Patients Undergoing Treatment for Pancreatic or Head and Neck Cancers, ClinicalTrials.gov, May 13, 2015, Ketamine, NCT02442739. Singh 2016.

Singh Jaskaran: "Intranasal sketamine in, Treatment Resistant Depression—A Double-blind, Randomized, Efficacy and Dose Response Study", International Journal of Neuropsychopharmacology, Cambridge Univ. Press, Cambridge, vol. 19, No. Suppl. 1, May 31, 2016 (May 31, 2016), XP009511636, p. 24, ISSN: 1461-1457, DOI: 10.7490/F1000RESEARCH.1111967.I.

Spitzer, "A brief measure for assessing generalized anxiety disorder—the GAD-7". Arch. Intern. Med., 2006, 166(10), 1092-1097.

Spitzer, JAMA, 1999, 282(18), 1737-1744.

Stucki et al., "Development of ready-to-use ketamine hydrochloride syringes for safe use in post-operative pain", European Journal of Hospital Pharmacy, 2008, vol. 14, Issue 1, pp. 14-18.

Tagum, "Redefining affective disorders: relevance for drug Development", CNS Neurosci. ther., 2008, 14(1), 2-9.

Tamura et al., "An examination of the efficiency of the sequential parallel design in psychiatric clinical trials", Clinical Trails, 2007, 4, 309-317.

Tamura, "Estimation of treatment effect for the sequential parallel design", Stat. Med., 2011, 30(30), 3496-3506.

Trivedi et al., "The Inventory of Depressive Symptomatology, Clinical Rating (IDS-C) and Self-Report (IDS-SR) in public sector patients with mood disorders: a psychometric evaluation", Psychol. Med., 2004, 34(1), 73-82.

Vollenweider et al., Differential psychopathology and patterns of cerebral glucose utilisation produced by (S)-and (R)-ketamine in healthy volunteers using positron emission tomography (PET), European Neuropsychopharmacology (1997) pp. 25-38, vol. 7.

Wang et al., "Effects of penetration enhancers on the permeability of ketamine hydrochloride through an isolated rabbit's nasal mucosa", Journal of Shenyang Pharmaceutical University, 2004, Issue 5, pp. 321-323 & 340.

White, "Comparative Pharmacology of the Ketamine Isomers. Studies in Volunteers", Br. J. Anaesth., 1985, 57(2), 197-203.

Williams, "Development and reliability of a structured interview guide for the Montgomery asberg depression rating Scale (SIGMA)", Br. J. Psychiatry, 2008, 192(1), 52-58 on days 1 (pre-dose and 2 hour post-dose), 2, 8 (pre-dose), 9, and 15, using the structured interview guide (SIGMA). See, Williams 2008.

Yang et al., "R-Ketamine: A rapid onset and sustained antidepressant without psychotomimetic side effects", Transl. Psychiatry, 2015, 5, 1-11.

Zarate, National Institute of Mental Health, Brain & Behavior Research Foundation Webinar, Ketamine & Next Generation Therapies With Rapid Antidepressant Effects, Aug. 13, 2013, 47 pages.

Zou, et al, Potential Neurotoxicity of Ketamine in the Developing Rat Brain, Toxicological Sciences, Dec. 6, 2009, pp. 149-158, vol. 108 Issue 1.

Zhong, et al, Mood and neuropsychological effects of different doses of ketamine in electroconvulsive therapy for treatment-resistant depression, Journal of Affective Disorders, May 12, 2016, pp. 124-130, vol. 201.

Zarate, et al., Replication of Ketamine's Antidepressant Efficacy in Bipolar Depression: A Randomized Controlled Add-on Trial, Biol Psychiatry, Jun. 1, 2012, pp. 1-18, vol. 71 Issue 11.

Zarate, et al., Regulation of Cellular Plasticity Cascades in the Pathophysiology and Treatment of Mood Disorders, AnnalsNew York Academy of Sciences, 2003, pp. 273-291, vol. 1003.

Zarate, et al., Brief Reports an Open-Label Trial of the Glutamate-Modulating Agent Riluzole in Combination with Lithium for the Treatment of Bipolar Depression, Biol. Psychiatry, 2005, pp. 430-432, vol. 57.

Zarate, et al., An open-Lable Trial of Riluzole in Patients With Treatment-Resistant major Depression, Am J Psychiatry, Jan. 1, 2004, pp. 171-174, vol. 161.

Zarate, et al., A Randomized Trail of an N-methyl-D-aspartate Antagonist in Treatment-Resistant Major Depression, Arch Gen Psychiatry, 2006, pp. 856-864, vol. 63.

Zarate, et al., A Double-Blind, Placebo-Controlled Study of Memantine in the Treatment of Major Depression, Am J Psychiatry, 2006, pp. 153-155, vol. 163 Issue 1.

Zanos, et al., Intracellular Signaling Pathways Involved in (S)-and (R)-Ketamine Antidepressant Actions, Biological Psychiatry, Jan. 1, 2008, pp. 2-4, vol. 83.

Zanos, et al., Effects of a ketamine metabolite on synaptic NMDAR function, Nature, Jun. 22, 2017, pp. E1-E2, vol. 546.

Young, et al., Young Mania Rating Scale (YMRS), Br J Psychiatry, 1978, pp. 429-435, vol. 133.

Yilmaz, et al., Prolonged effect of an anesthetic dose of ketamine on behavioral despair, Pharmacology, Biochemistry and Behavior, 2002, pp. 341-344, vol. 71.

Yang, et al., R-ketamine: a rapid-onset and sustained antidepressant without psychotomimetic side effects, Transl Psychiatry, Sep. 1, 2015, pp. 1-19, vol. 5 Issue 9.

Yale University., PET Imaging of mGLuRS With Drug Challenge, ClinicalTrials.gov, Sep. 24, 2012, ketamine, NCT01691092.

(56) References Cited

OTHER PUBLICATIONS

Yale University., Ketamine Infusion for Adolescent Depression and Anxiety, ClinicalTrials.gov, Oct. 20, 2015, Ketamine, NCT02579928.
Yale University., Ketamine in Borderline Personality Disorder, ClinicalTrials.gov, Jan. 10, 2018, Ketamine, NCT03395314.
Yale University., Ketamine for Low Mood States in the ER, ClinicalTrials.gov, Sep. 27, 2010, Ketamine, NCT01209845.
Yale University., Imaging SV2A in Mood Disorders, ClinicalTrials.gov, Apr. 12, 2016, ketamine, NCT02734602.
Yale University., Examining the Effect of Ketamine on Glutamate/Glutamine Cycling, ClinicalTrials.gov, Jan. 15, 2014, Ketamine, NCT02037035.
Yale University., Cognitive Therapy to Sustain the Antidepressant Effects of Intravenous Ketamine in Treatment-resistant Depression, ClinicalTrials.gov, Jan. 23, 2017, ketamine, NCT03027362.
Yale University., Cognitive Behavioral Therapy in Prolonging the Antidepressant Effects of Intravenous Ketamine, ClinicalTrials.gov, Nov. 13, 2014, Ketamine, NCT02289248.
Yale University., Alpha-Amino-3-Hydroxy-5-Methyl-4-Isoxazole Propionic Acid Receptor Components of the Anti-Depressant Ketamine Response, ClinicalTrials.gov, Dec. 8, 2017, Ketamine, NCT03367533.
Yale University, Trial of Ketamine and Lithium Therapy in Bipolar Depression, ClinicalTrials.gov, Jan. 15, 2013, Ketamine, NCT01768767.
Yale University, Ketamine for Depression and Alcohol Dependence (KetamineDep), ClinicalTrials.gov, Mar. 12, 2012, Ketalar (ketamine), NCT01551329.
Wonkwang University Hospital., Dexamethasone and Ketamine on Change of Postoperative Mood, ClinicalTrials.gov, Jun. 21, 2017, Ketamine, NCT03194594.
Womble, et al., Effects of Ketamine on Major Depressive Disorder in a Patient With Posttraumatic Stress Disorder, AANA Journal, 2013, pp. 118-119, vol. 81 Issue 2.
Wirz-Justice, et al., Sleep Deprivation in Depression: What Do We Know, Where Do We Go?, Biol Psychiatry, May 18, 1999, pp. 445-453, vol. 46.
Williams, et al., Opioid Receptor Anesthesia attenuates Antidepressant Effects of Ketamine, Biological Psychiatry, May 12, 2018, pp. 1-1.
Williams, et al., Attenuation of Antidepressant Effects of Ketamine by Opioid Receptor Antagonism, ajp. psychiatryonline.org, 2018, pp. 1-11, pagenumber.
William V. Bobo, M.D., Effect of Lithium Versus Placebo in Adults With Treatment-Resistant Depression Who Are Receiving Ketamine, ClinicalTrials.gov, Sep. 25, 2017, Ketamine, NCT03290963.
William Beaumont Hospitals., IN Ketamine vs IN Midazolam and Fentanyl for Laceration Repair, ClinicalTrials.gov, May 18, 2018, Ketamine, NCT03528512.
Wilkinson, et al., Cognitive Behavior Therapy May Sustain Antidepressant Effects of Intravenous Ketamine in Treatment-Resistant Depression, Psychother Psychosom, May 11, 2017, pp. 162-167, vol. 86.
Wikipedia, Esketamine, Wikipedia, Sep. 1, 2015, pp. 1-4, Wikipedia.
Who_Expert Peer Review Report, Expert Committee on Drug Dependence Thirty-sixth Meeting, WHO_Expert peer review report, 2014, pp. 1-4, Agenda item 6.2.
Who_ Essential Medicines and Health Products., Essential medicines, WHO_Essential medicines and health products, 2015, pp. 1-3, Page Number.
Who_Depression Fact Sheet., Media centre Depression, WHO Depression fact sheet, 2012, pp. 1-3, Fact sheet N°369.
Who Critical Review Ketamine., Introduction, WHO critical review ketamine, 2006, pp. 1-30, 34th ECDD 2006/4.3.
White et al., Comparative Pharmacology of Ketamine Isomers, Br. J. Anaesth., 57(2):197-203, 1985.
Weksler, et al., Nasal ketamine for paediatric premedication, Canadian Journal of Anaesthesia, 1993, pp. 119-121, vol. 40 Issue 2.
Wasserman, et al., Saving and Empowering Young Lives in Europe (SEYLE): a randomized controlled trial, BMC Public Health, 2010, pp. 1-14, vol. 10 Issue 192.
Washington, et al., Determination of baseline human nasal pH and the effect of intranasally administered buffers, International Journal of Pharmaceutics, Nov. 24, 1999, pp. 139-146, vol. 198.
Washington University School of Medicine., Nitrous Oxide as Treatment for Major Depression—a Pilot Study, ClinicalTrials.gov, May 15, 2014, Nitrous Oxide, NCT02139540.
Washington University School of Medicine, Treatment Resistant Depression (Pilot), ClinicalTrials.gov, Aug. 10, 2010, ketamine, NCT01179009.
Washington University School of Medicine, Cognitive Recovery After Electroconvulsive Therapy and General Anesthesia (RCC2), ClinicalTrials.gov, May 4, 2016, Ketamine, NCT02761330.
Washington et al., Determination of baseline human nasal pH and the effect of intranasally administered buffers, International Journal of Pharmaceutics 198:139-146, 2000.
Wang, et al., NMDA/NR28 Selective Antagonists in the Treatment of Ischemic Brain Injury, Current Drug Targets—CNS & Neurological Disorders, 2005, pp. 143-151, vol. 4 Issue 2.
Wang, et al., Independent Telephone-based Assessment of Depressive Symptoms in China, Csp, 2018, pp. 1-1, Page Number.
Wan, et al., Ketamine Safety and Tolerability in Clinical Trials for Treatment-Resistant Depression, J Clin Psychiatry, 2015, pp. 1-11, vol. 76 Issue 3.
Vranken, et al, Iontophoretic administration of S(C)-ketamine in patients with intractable central pain: A placebo-controlled trial, Pain, Aug. 15, 2005, pp. 224-231, vol. 118, Elsevier B.V.
Best, et al., Combined transcranial magnetic stimulation and ketamine for treatment of refractory mood disorder, anxiety, and pain: A case report, Curr Neurobiol, Jan. 25, 2015, pp. 1-4, vol. 8 Issue 1.
Berum, et al., Definition, Assessment, and staging of Traetmenty-Resistant Refractory Major Depression: A Review of Current Concepts and Methods, Can J Psychiatry, 2007, pp. 46-54, vol. 52 Issue 1.
Bertolote, et al., Suicide attempts, plans, and ideation in culturally diverse sites: the Who Supre-Miss community survey, Psychological Medicine, 2005, pp. 1457-1465, vol. 35.
Bertolote, et al., Aglobal perspective on the mangnitude of suicide mortality, British Library, 2009, pp. 91-98, Chapter 14.
Berman, et al., The Efficacy and Safety of Aripiprazole as Adjunctive Therapy in Major Depressive Disorder: A Multicenter, Randomized, Double-Blind, Placebo-Controlled Study, J Clin Psychiatry, 2007, pp. 843-853, vol. 68 Issue 6.
Berman, et al., Antidepressant Effects of Ketamine in Depressed Patients, Biol Psychiatry, Aug. 12, 1999, pp. 351-354, vol. 47.
Beijing Tiantan Hospital, Ketamine and Postoperative Depressive Symptom, ClinicalTrials.gov, Mar. 22, 2017, Ketamine, NCT03086148.
Beck, et al., Assessment of Suicidal Intention: The Scale for Suicide Ideation, Journal of Consulting and Clinical Psychology, 1979, pp. 343-352, vol. 47 Issue 2.
Beck, et al., Assessment of Depression :The Depression Inventory, Psychological Measurements in Psychopharmacology. Mod Probl. Pharmacopsychait., 1974, pp. 151-169, vol. 7.
Beck, et al, Scale for Suicide Ideation: Psychometric Properties of a Self-Report Version, Journal of Clinical Psychology, 1988, pp. 499-505, vol. 44 Issue 4.
Beardslee, et al., A Family-Based Approach to the Prevention of Depressive Symptoms in Children at Risk: Evidence of Parental and Child Change, Pediatrics, 2003, pp. e119-e131, vol. 112 Issue 2.
Baylor College of Medicine., Research Study for Major Depressive Disorder: Investigation of Glutamate Medications, ClinicalTrials.gov, Jan. 5, 2007, ketamine, NCT00419003.
Baylor College of Medicine., Optimization of IV Ketamine for Treatment Resistant Depression, ClinicalTrials.gov, Oct. 8, 2008, Ketamine, NCT00768430.
Bartova, et al., Intravenous Administration of S-ketamine in a Severely Depressed Treatment-resistant Patient Receiving Tranylcypromine: a Case Report, Eur.Psychiat, 2015, pp. 1-1.
Bartova, et al., Combination of intravenous S-ketamine and oral tranylcypromine in treatment-resistant depression:A report of two cases, European Neuropsychopharmacology, Jul. 28, 2015, pp. 2183-2184, vol. 25.

(56) References Cited

OTHER PUBLICATIONS

Barbe, et al., Suicidality and Its Relationship to Treatment Outcome in Depressed Adolescents, Suicide and Life-Threatening Behavior, Aug. 15, 2003, pp. 44-55, vol. 34 Issue 1.

Ballard, et al., Neural Correlates of Suicidal Ideation and Its Reduction in Depression, International Journal of Neuropsychopharmacology, 2015, pp. 1-6.

Ballard, et al., Improvement in suicidal ideation after ketamine infusion: Relationship to reductions in depression and anxiety*, Journal of Psychiatric Research, Jul. 31, 2014, pp. 161-166, vol. 58.

Baldessarini, et al., Decreased risk of suicides and attempts during long-term lithium treatment: a meta-analytic review, Bipolar Disorders, Mar. 13, 2006, pp. 625-639, vol. 8.

Baji, et al., Age and Sex Analyses of Somatic Complaints and Symptom Presentation of Childhood Depression in a Hungarian Clinical Sample, J Clin Psychiatry, 2009, pp. 1467-1472, vol. 70 Issue 10.

Azevedo, et al., Transdermal Ketamine as an Adjuvant for Postoperative Analgesia After Abdominal Gynecological Surgery Using Lidocaine Epidural Blockade, Anesth Analg, Aug. 11, 2000, pp. 1479-1482, vol. 91.

Ayuso-Mateos, et al., Depressive disorders in Europe: prevalence figures from the ODIN study, British Journal of Psychiatry, Apr. 6, 2001, pp. 308-3016, vol. 179.

Astrazeneca., Study Where Pharmaco Magnetic Resonance Imaging (MRI) Effects of AZD6765 Will be Compared to Placebo in Depressive Male and Female Subjects, ClinicalTrials.gov, Jan. 12, 2010, Ketamine, NCT01046630.

Asarnow, et al., Treatment of Selective Serotonin Reuptake Inhibitor-Resistant Depression in Adolescents: Predictors and Moderators of Treatment Response, J Am Acad Child Adolesc Psychiatry, Sep. 29, 2009, pp. 330-339, vol. 48 Issue 3.

Asarnow, et al., Effectiveness of a Quality Improvement Intervention for Adolescent Depression in Primary Care Clinics, JAMA, Jan. 19, 2005, pp. 311-319, vol. 293 Issue 3.

Asarnow, et al., Depression in Youth: Psychosocial Interventions, Journal of Clinical Child Psychology, Mar. 14, 2000, pp. 33-47, vol. 30 Issue 1.

Asarnow, et al., Depression and role impairment among adolescents in primary care clinics, Journal of Adolescent Health, Nov. 4, 2004, pp. 477-483, vol. 37.

Anonymous: "NCT02133001 on 2014_06_23: ClinicalTrials.gov Archive", Jun. 23, 2014 (Jun. 23, 2014), pp. 1-6, XP055230128, Retrieved from the Internet: URL:https://clinicaltrials.gov/archive/NCT 02133001/2014_06_23.

Anna Meuronen, MD., Intranasal Esketamine and Fentanyl for Pain in Minor Trauma, ClinicalTrials.gov, Feb. 5, 2018, Esketamine, NCT03421275.

Angst, et al., Mortality of patients with mood disorders: follow-up over 34-38 years, Journal of Affective Disorders, Apr. 3, 2001, pp. 167-181, vol. 68.

Angold, et al., Puberty and depression: the roles of age, pubertal status and pubertal timing, Psychological Medicine, 1998, pp. 51-61, vol. 28.

Angold, et al., Comorbidity, J.Child Psychol. Psychiat, 1999, pp. 57-87, vol. 40 Issue 1.

Angelica Lavito., Ketamine is emerging as a popular treatment for depression. New research suggests the drug acts like an opioid, Biotech and Pharmaceuticals, Aug. 29, 2018, pp. 1-5.

Andrade, et al., Intranasal Drug Delivery in Neuropsychiatry: Focus on Intranasal Ketamine for Refractory Depression, J Clin Psychiatry, 2015, pp. e628-e631, vol. 76 Issue 5.

Anderson, et al., Ketamine augmentation of electroconvulsive therapy to improve neuropsychological and clinical outcomes in depression (Ketamine-ECT): a multicentre, double-blind, randomised, parallel-group, superiority trial, Lancet Psychiatry, Mar. 27, 2017, pp. 365-377, vol. 4.

Anderson, et al., Evidence-based guidelines for treating depressive disorders with antidepressants: A revision of the 2000 British Association for Psychopharmacology guidelines, Journal of Psychopharmacology, 2008, pp. 343-396, vol. 22 Issue 4.

Anand, et al., Attenuation of the Neuropsychiatric Effects of Ketamine With Lamotrigine., Arch Gen Psychiatry., 2000, pp. 270-276, vol. 57.

Amercian Pharmaceutical Review., Controlled Release Roundtable, Lonza, Jun. 30, 2017, pp. 1-10.

Amercian Association of Suicidology., Facts About Suicide and Depression, American Association of Suicidology, 2010, pp. 1-4.

Alphs L, et al., Validation of Suicidal Ideation and Behavior Assessment Tool (SIBAT): Intra-and Inter-rater Reliability, European Symposium on Suicide & Suicidal Behavior (ESSSB), 2018, pp. 1-1, Poster 222.

Alosh, et al., A consistency-adjusted alpha-adaptive strategy for sequential testing, Statistics in Medicine, Apr. 8, 2010, pp. 1559-1571, vol. 29.

Allen, et al., Serum BDNF as a peripheral biomarker of treatment-resistant depression and the rapid antidepressant response: A comparisonof ketamine and ECT, Journal of Affective Disorders, Jul. 29, 2015, pp. 306-311, vol. 186.

Allen, et al., Screening for Suicidal Ideation and Attempts among Emergency Depatment Medical Patients: Instrument and Results from the Psychiatric Emergency Research Collaboration, Suicide and Life-Threatening Behavior, 2013, pp. 1-12.

Alizadeh, et al., Antidepressant Effect of Combined Ketamine and Electroconvulsive Therapy on Patients With Major Depressive Disorder: A Randomized Trial, Iran J Psychiatry Behav Sci, Sep. 23, 2015, pp. e1573-e1578, vol. 9 Issue 3.

Alison Goate, DPhil., Changing the Equation for Alzheimer's, Mount Sinai Science & Medicine, 2018, pp. 1-2.

Aligeti, et al., Rapid Resolution of Suicidal Behavior and Depression With Single Low-Dose Ketamine Intravenous Push Even After 6 Months of Follow-Up, Journal of Clinical Psychopharmacology, 2014, pp. 533-535, vol. 34 Issue 4.

Alessandri, et al., Effects of Ketamine on Tunnel Maze and Water Maze Performance in the Rat, Behavioral and Neural Biology, 1989, pp. 194-212, vol. 52.

Albott, et al., Neurocognitive Effects of Repeated Ketamine Infusions in Co-Occurring Posttraumatic Stress Disorder and Treatment-Resistant Depression, Biological Psychiatry, May 15, 2017, pp. S405-S405, vol. 81.

Al Shirawi, et al., Oral Ketamine in Treatment-Resistant Depression A Clinical Effectiveness Case Series, J Clin Psychopharmacol, 2017, pp. 464-467, vol. 37 Issue 4.

Aitken, et al., Section of Measurement in Medicine., Proc. Roy. Soc. Med., 1969, pp. 989-993, vol. 62.

Phelps et al., Family history of alcohol dependence and initial antidepressant response to an N-methyl-D-aspartate antagonist. Biological psychiatry 65, 2009, pp. 181-184.

Pfizer, (S)-(+)-Ketamine Hydrochloride Solution, Material Safety Data Sheet, Nov. 5, 2008, pp. 1-8, Version 1.0.

Pfenninger, et al., Cognitive Impairment after Small-dose Ketamine Isomers in Comparison to Equianalgesic Racemic Ketamine in Human Volunteers, Anesthesiology, 2002, pp. 357-366, vol. 96 Issue 2.

Pfeiffer, et al., Traetment-Resistant Depression and Risk of Suicide, Suicide and Life-Threatening Behavior, Dec. 26, 2012, pp. 1-10.

Per Gisle Djupesland., Nasal drug delivery devices: characteristics and performance in a Clinical Perspective—a Review, Drug Deliv. and Transl. Res, Oct. 18, 2012, pp. 1-21.

Per Gisle Djupesland, Nasal Drug Delivery Devices: Characteristics and Performance in a Clinical Perspective—A Review. Drug Deliv. and Transl. Res. (2013) 3:42-64.

Pennybaker, et al., Symptomatology and Predictors of Antidepressant Efficacy in Extended Responders to a Single Ketamine Infusion, J Affect Disord., Jan. 15, 2015, pp. 1-20, vol. 208.

Peking University First Hospital., Low-dose Ketamine and Post-partum Depression in Patients With Prenatal Depression, ClinicalTrials.gov, Nov. 8, 2017, Ketamine, NCT03336541.

Pearson, et al., Intervention Research With Persons at high Risk for Suicidality: Safety and Ethical Considerations, J Clin Psychiatry, 2001, pp. 17-26, vol. 62 Supp.lementary 25.

(56) References Cited

OTHER PUBLICATIONS

Paule, et al., Behavioral Effects in Primates Ketamine Anesthesia during the first week of life can cause long-lasting cognitive deficits in rhesus monkey, Neurotoxicology and Teratology, 2011, pp. 1-33.
Paul, et al, Comparison of racemic ketamine and S-ketamine in treatment-resistant major depression: Report of two cases, The World Journal of Biological Psychiatry, Sep. 28, 2007, pp. 241-244, vol. 10 Issue 3, Informa UK Ltd.
Paul J. Lamothe., Ketamine for Treatment-resistant Depression: A Multicentric Clinical Trial in Mexican Population, ClinicalTrials. gov, Jun. 5, 2013, Ketamine, NCT01868802.
Paslakis et al, Oral Administration of the NMDA Receptor Antagonist S-Ketamine as Add-On Therapy of Depression: A Case Series, Pharmacopsychiatry, 2010, pp. 33-35, vol. 43.
PApp., et al., Antidepressant activity of non-competitive and competitive NMDA receptor antagonists in a chronic mild stress model of depression, European Journal of Pharmacology, Jun. 21, 1994, pp. 1-7, vol. 263.
Overall, et al., The Brief Psychiatric Rating Scale 1, Psychological Reports, Apr. 17, 1962, pp. 799-812, vol. 10.
Overall, et al., Brief psychiatric rating scale, 2018, pp. 1-6.
Ostroff, et al., Antidepressant Effect of Ketamine During ECT, American Journal of Psychiatry, 2005, pp. 1385-1386, vol. 162 Issue 7.
Oshima, et al., Continuous subcutaneous injection of ketamine for cancer pain, Canadian Journal of Anaesthesia, 1990, pp. 385-392, vol. 37 Issue 3.
Opler, et al., Ameliorating treatment-refractory depression with intranasal ketamine: potential NMDA receptor actions in the pain circuitry representing mental anguish, CNS Spectrums, Jan. 26, 2016, pp. 1-12.
Okamoto et al, Rapid Antidepressant Effect of Ketamine Anesthesia During Electroconvulsive Therapy of Treatment-Resistant Depression, Journal of ECT, 2010, pp. 223-227, vol. 26 Issue 3.
Oishi, et al., Effects of propyl paraben on the male reproductive system, Food and Chemical Toxicology, Jul. 7, 2002, pp. 1807-1813, vol. 40, Elsevier Science Ltd.
O'Connor, et al., Screening for Suicide Risk in Primary Care: A Systematic Evidence Review for the U.S. Preventive Services Task Force, Evidence Synthesis, 2013, pp. 1-126, AHRQ Publication No. 13-05188-EF-1.
Northwestern University., Postpartum Perineal Pain After Obstetric Anal Sphincter Injuries, ClinicalTrials.gov, Mar. 20, 2018, ketamine, NCT03470675.
Northwell Health., Ketamine as an Augmentation Strategy for Electroconvulsive Therapy (ECT) in Depression, ClinicalTrials. gov, Jun. 20, 2013, Ketamine, NCT01881763.
Northside Clinic, Australia., Ketamine as an Anaesthetic Agent in Electroconvulsive Therapy (ECT), ClinicalTrials.gov, May 20, 2008, Ketamine, NCT00680433.
Noppers et al, Absence of long-term analgesic effect from a short-term S-ketamine infusion on fibromyalgia pain: A randomized, prospective, double blind, active placebo-controlled trial, European Journal of Pain, Apr. 11, 2011, pp. 942-949, vol. 15, Elsevier Ltd.
Nock, et al., Prevalence, Correlates, and Treatment of Lifetime Suicidal Behavior Among Adolescents, JAMA Psychiatry, Nov. 7, 2013, pp. 300-310, vol. 70 Issue 3.
Nock, et al., Cross-national prevalence and risk factors for suicidal ideation, plans and attempts, The British Journal of Psychiatry, 2008, pp. 98-105, vol. 192.
Nock, et al., Cross-National Analysis of the Associations among Mental Disorders and Suicidal Behavior: Findings from the WHO World Mental Health Surveys, PLoS Medicine, 2009, pp. 1-17, vol. 6 Issue 8.
Nierenberg, et al., Suicide risk management for the sequenced treatment alternatives to relieve depression study: app.lied NIMH guidelines, Journal of Psychiatric Research, Mar. 12, 2004, pp. 583-589, vol. 38.

Nierenberg, et al., A Comparison of Lithium and T3 Augmentation Following Two Failed Medication Treatments for Depression: A STAR'D Report, Am J Psychiatry, Jun. 23, 2006, pp. 1519-1530, vol. 163 Issue 9.
Niciua, et al., Subanesthetic Dose Ketamine Does Not Induce an Affective Switch in Three Independent Samples of Treatment-Resistant Major Depression, Biol Psychiatry, Nov. 15, 2013, pp. 1-3, vol. 74 Issue 10.
Niciu, et al., Ketamine's Antidepressant Efficacy is Extended for at Least Four Weeks in Subjects with a Family History of an Alcohol Use Disorder, International Journal of Neuropsychopharmacology, Jul. 2, 2014, pp. 1-7.
Newcomer, et al., Ketamine-Induced NMDA Receptor Hypofunction as a Model of Memory Impairment and Psychosis, Neuropsychopharmacology, 1999, pp. 106-118, vol. 20 Issue 2.
New York University School of Medicine, Study on the Use of Low Dose Ketamine After Gastric Bypass and Gastrectomy, ClinicalTrials. gov, May 22, 2015, Ketamine, NCT02452060.
New York University School of Medicine, Ketamine as a Rapidly-Acting Antidepressant in Depressed Emergency Department Patients, ClinicalTrials.gov, Apr. 8, 2014, Ketamine, NCT02106325.
New York State Psychiatric Institute., Ketamine in the Treatment of Suicidal Depression, ClinicalTrials.gov, Oct. 4, 2012, Ketamine, NCT01700829.
New York State Psychiatric Institute., Ketamine for Suicidality in Bipolar Depression, ClinicalTrials.gov, Sep. 17, 2013, Ketamine, NCT01944293.
New York State Psychiatric Institute., Investigation of the NMDA Antagonist Ketamine as a Treatment for Tinnitus, ClinicalTrials. gov, Nov. 8, 2017, Ketamine Hydrochloride in saline, NCT03336398.
New York State Psychiatric Institute, NMDA Antagonists in Bipolar Depression, ClinicalTrials.gov, Apr. 17, 2013, ketamine, NCT01833897.
Neurorx, Inc., Sequential Therapy for the Treatment of Severe Bipolar Depression. (STABIL-B), ClinicalTrials.gov, Nov. 28, 2016, Ketamine, NCT02974010.
Neurorx, Inc., NRX101 Glx Biomarker Validation Study (NRX-GLX), ClinicalTrials.gov, Jan. 18, 2018, NRX-101, NCT03402152.
Neurorx, Inc., NRX100 vs. Placebo for Rapid Stabilization of Acute Suicidal Ideation and Behavior in Bipolar Depression (SevereBD), ClinicalTrials.gov, Jan. 11, 2018, ketamine, NCT03396601.
Neurorx, Inc., NRX-101 for Maintenance of Remission From Severe Bipolar Depression in Patients With Suicidal Ideation (SBD-ASIB), ClinicalTrials.gov, Jan. 10, 2018, NRX-101, NCT03396068.
Nationwide Children's Hospital., An Open Prospective Trial of IV Ketamine in Suicidal Adolescents, ClinicalTrials.gov, Jan. 29, 2014, Ketamine, NCT02048423.
National Strategy for Suicide Prevention, Goals and Objectives for Action, National Strategy for Suicide Prevention, 2012, pp. 1-184.
National Institute of Neurology and Neurosurgery, Mexico., Clinical Trial of the Use of Ketamine in Treatment Resistant Depression, ClinicalTrials.gov, Nov. 20, 2015, Ketamine, NCT02610712.
National Institute of Mental Health (NIMH)., Rapid Antidepressant Effects of Ketamine in Major Depression, ClinicalTrials.gov, Aug. 2, 2004, Ketamine, NCT00088699.
National Institute of Mental Health (NIMH)., Neuropharmacologic Imaging and Biomarker Assessments of Response to Acute and Repeated-Dosed Ketamine Infusions in Major Depressive Disorder, ClinicalTrials.gov, Feb. 27, 2017, Ketamine, NCT03065335.
National Institute of Mental Health (NIMH), The Neurophysiological Effects of Intravenous Alcohol as Potential Biomarkers of Ketamine's Rapid Antidepressant Effects in Major Depressive Disorder, ClinicalTrials.gov, Apr. 24, 2014, Ketamine, NCT02122562.
Skolnick, et al., Antidepressants for the new millennium, European Journal of Pharmacology, Apr. 30, 1999, pp. 31-40, vol. 375.
Skolnick, et al., Adaptation of N-Methyl-D-Aspartate (NMDA) Receptors following Antidepressant Treatment Implications for the Pharmacotherapy of Depression, Pharamacopsychiat, 1996, pp. 23-26, vol. 29.
Singh, et al., A Double-Blind, Randomized, Placebo-Controlled, Dose-Frequency Study of Intravenous Ketamine in Patients With Treatment-Resistant Depression, AmJ Psychiatry, 2016, pp. 816-826, vol. 173.

(56) References Cited

OTHER PUBLICATIONS

Short, AL., Side-effects associated with ketamine use in depression: a systematic review, Lancet Psychiatry, 2018, pp. 65-78, vol. 5.

Shiroma, et al., Neurocognitive performance and serial intravenous subanesthetic ketamine in treatment-resistant depression, International Journal of Neuropsychopharmacology, 2014, pp. 1805-1813, vol. 17.

Shiroma, et al., Augmentation of response and remission to serial intravenous subanesthetic ketamine in treatment resistant depression, Journal of AffectiveDisorders, Oct. 29, 2013, pp. 123-129, vol. 155.

Shi Jinyun, Study of Ketamine as an Antidepressant in Major Depressive Disorder, ClinicalTrials.gov, Apr. 9, 2012, Ketamine, NCT01573741.

Sheba Medical Center., Ketamine Infusions for Major Depression Disorder (Ketamie), ClinicalTrials.gov, Aug. 19, 2014, Ketamine, NCT02219867.

Sheba Medical Center., D-cycloserine for Relapse Prevention Following Intravenous Ketamine in Treatmentresistant Depression, ClinicalTrials.gov, May 13, 2016, Ketamine, NCT02772211.

Shaw et al., Ketamine amplifies induced gamma frequency oscillations in the human cerebral cortex. European neuropsychopharmacology : The journal of the European College of Neuropsychopharmacology 25, 2015, pp. 1136-1146.

Shalvata Mental Health Center, Intra-nasal vs. Intravenous Ketamine Administration, ClinicalTrials.gov, Jan. 1, 2016, Ketamine, NCT02644629.

Scotia. Irwin, MD, Pho., Study of Oral Ketamine Versus Placebo for Treating Depression in Patients Undergoing Treatment for Cancer, ClinicalTrials.gov, Jul. 19, 2016, Ketamine, NCT02836288.

Schule, et al., Repeated S-Ketamine Infusions in Treatment-Resistant Depression, Topic: E02-e-Poster Oral Session 02: Depression and Suicide, 2014, pp. 1-1, Article EPA-1659.

Schonenberg, et al., Ketamine aggravates symptoms of acute stress disorder in a naturalistic sample of accident victims, Journal of Psychopharmacology, 2008, pp. 493-497, vol. 22 Issue 5.

Scheidegger et al., Ketamine administration reduces amygdalo-hippocampal reactivity to emotional stimulation. Human brain mapping 37, 2016, pp. 1941-1952.

Saveanu, et al., The International Study to Predict Optimized Treatment in Depression (iSPOT-D): Outcomes from the acute phase of antidepressant treatment, Journal of Psychiatric Research, Dec. 23, 2014, pp. 1-12, vol. 61.

Sarchiapone, et al., Association of Polymorphism (Val66met) of Brain-Derived Neurotrophic Factor with Sucide Attempts in Depressed Patients, Neuropsychobiology, Jul. 7, 2008, pp. 139-145, vol. 57.

Sarah-Jayne Blakemore., The social brain in adolescence, Nature Reviews! Neuroscience, 2008, pp. 267-277, vol. 9.

Sapolsky, et al, Commentary Is Impaired Neurogenesis Relevant to the Affective Symptoms of Depression?, Biol Psychiatry, 2004, pp. 137-139, vol. 56.

Sanacora, et al., Subtype-Specific Alterations of y-Aminobutyric Acid and Glutamate in Patients With Major Depression, Arch Gen Psychiatry, 2004, pp. 705-713, vol. 61.

Salvadore G Ed—Sanacora Gerard et al: "Impact of the Val66Met Polymorphism of Brain-Derived Neurotrophic Factor on Esketamine and Ketamine Antidepressant Effects in Patients with Treatment-Resistant Depression", Biological Psychiatryvol. 77, No. 9 supplement, May 1, 2015 (May 1, 2015), p. 360S.

Salvadore et al., Anterior cingulate desynchronization and functional connectivity with the amygdala during a working memory task predict rapid antidepressant response to ketamine. Neuropsychopharmacology: official publication of the American College of Neuropsychopharmacology 35, 2010, pp. 1415-1422.

Sadove, et al, Analgesic Effects of Ketamine Administered in Subdissociative Doses, Anaesthesia and Analgesia. Current Researches, 1971, pp. 452-457, vol. 50 Issue 3.

Sackeim, et al., Vagus Nerve Stimulation (VNS™) for Treatment-Resistant Depression: Efficacy, Side Effects, and Predictors of Outcome, N Europsychopharmacology, 2001, pp. 714-728, vol. 25 Issue 5.

Rybakowski et al., Single ketamine infusion in bipolar depression resistant to antidepressants: are neurotrophins involved? Human psychopharmacology 28, 2013, pp. 87-90.

Rush, et al., Acute and Longer-Term Outcomes in Depresses Outpatients Requiring one or Several Treatment Steps; A STAR'D Report, Am. J. Psychiatry, 2006, pp. 1905-1917, vol. 163.

Rush, et al, Research Issues in the Study of Difficult-to-Treat Depression, Biol Psychiatry, Jan. 13, 2003, pp. 743-753, vol. 53.

Rothman, et al., Noncompetitive N-Methyl-D-Aspartate Antagonists Affect Multiple Lonie Currents, The Journal of Pharamacology and Experimental Therapeutics, Mar. 30, 1988, pp. 137-142, vol. 246, Issue 1.

Rot, et al., Ketamine for Depression: Where Do We Go from Here?, Biol Psychiatry, May 9, 2012, pp. 1-31.

Ribeiro, et al., The Use of Ketamine for the Treatment of Depression in the Context of Psychotic Symptoms, Biological Psychiatry, May 1, 2016, pp. e65-e66, vol. 79.

Rhode Island Hospital, Intranasal Ketamine for Procedural Sedation in Pediatric Laceration Repair, ClinicalTrials.gov, Mar. 23, 2007, Ketamine, NCT00451724.

Remigius U Agu., Challenges in nasal drug absorption: how far have we come?, Future Science, Jul. 12, 2016, pp. 1-2, vol. 7 Issue 7.

Reeves, et al., Efficacy of Risperidone Augmentation to Antidepressants in the Management of Suicidality in Major Depressive Disorder: A Randomized, Double-Blind, Placebo-Controlled Pilot Study, J Clin Psychiatry, 2008, pp. 1228-1236, vol. 69 Issue 8.

Rebecca Price, Intravenous Ketamine Plus Neurocognitive Training for Depression, ClinicalTrials.gov, Aug. 2, 2017, Intravenous ketamine, NCT03237286.

Rasmussen, et al., Serial infusions of low-dose ketamine for major depression, Journal of Psychopharmacology, 2013, pp. 444-450, vol. 27 Issue 5.

Randall, et al., Assessment of Self-Harm Risk Using Implicit Thoughts, Psychological Assessment, May 6, 2013, pp. 1-8~.

Quintana, et al., Dose-dependent social-congnitive effects of intranasal oxytocin delivered with novel breath powered device in adults with autism spectrum disorder: a randomized placebo-controlled double-blind crossover trial, Translational Psychiatry, May 23, 2017, pp. 1-9, vol. 7.

Psychiatric University Hospital, Zurich., A Multimodal Neuroimaging Study of Brain Activation Patterns Under Ketamine, ClinicalTrials.gov, Aug. 1, 2018, Ketamine, NCT03609190.

Przegalinski, et al., Antidepressant-like Effects of a Partial Agonist at Strychnine-insensitive Glycine Receptors and a competitive NMDA Receptor Antagonist, Neurophararmacology, 1997, pp. 31-37, vol. 36 Issue 1.

Pringle, et al., A Strategic App roach for Prioritizing Research and Action to Prevent Suicide, Psychiatric Services, 2013, pp. 71-75, vol. 64 Issue 1.

Price_et_al, Effects of Intravenous Ketamine on Explicit and Implicit Measures of Suicidality in Treatment-Resistant Depression, Biol Psychiatry, 2009, pp. 522-526, vol. 66, Society of Biological Psychiatry.

Price, et al., Effects of Ketamine on Explicit and Implicit Suicidal Cognition: A Randomized Controlled Trial in Treatment-Resistant Depression, Depress Anxiety., 2014, pp. 1-18, vol. 31, Issue 4.

Price, et al., Effects of Intravenous Ketamine on Explicit and Implicit Measures of Suicidality in Treatment-Resistant Depression, Biol Psychiatry, Apr. 28, 2009, pp. 1-5.

Pouya Movahed Rad., Ketamine as an Alternative Treatment to ECT in Major Depressive Disorder, ClinicalTrials.gov, Jan. 20, 2016, Ketamine, NCT02659085.

Posner, et al., The Columbia-Suicide Severity Rating Sclae: Initial Validity and internal Consistency Findings From Three Multisite studies with adolescents and Adults, Am JP sychiatry, 2011, pp. 1266-1277, vol. 168 Issue 12.

Posner, et al., Columbia Classification Algorithm of Suicide Assessment (C-CASA): Classification of Suicidal Events in the FDA's

(56) References Cited

OTHER PUBLICATIONS

Pediatric Suicidal Risk Analysis of Antidepressants, Am J Psychiatry, 2007, pp. 1035-1043, vol. 164.
Poreh, et al., The BPQ: A Scale for the Assessment of Borderline Personality Based on DSM-IV Criteria, Journal of Personality Disorders, 2006, pp. 247-260, vol. 20 Issue 3.
Pierre Blier., Exploiting N-Methyl-D-Aspartate Channel Blockade for a Rapid Antidepressant Response in Major Depressive Disorder, Biol Psychiatry, May 30, 2013, pp. 238-239, vol. 74.
Pi Mylan Ketamine HCL Injection, Ketamine Hydrochloride—ketamine hydrochloride injection, selution Mylan Institutional LLC, Pi Mylan Ketamine HCl Injection, 2012, 1-16.
Janssen Research & Development, LLC, A Mass Balance Study With a Microtracer Dose of 14C-esketamine in Healthy Male Participants, ClinicalTrials.gov, Feb. 4, 2016, Esketamine, NCT02674295.
Janssen Research & Development, LLC, A Long-term, Safety and Efficacy Study of Intranasal Esketamine in Treatment-resistant Depression (SUSTAIN-2), ClinicalTrials.gov, Jul. 14, 2015, Esketamine, NCT02497287.
Janssen Research & Development, LLC, A Double-blind Study to Assess the Efficacy and Safety of Intranasal Esketamine for the Rapid Reduction of the Symptoms of Major Depressive Disorder, Including Suicidal Ideation, in Participants Who Are Assessed to be at Imminent Risk for Suicide, ClinicalTrials.gov, May 7, 2014, Esketamine, NCT02133001.
Janssen Pharmaceutical K.K., A Study to Evaluate the Efficacy, Safety and Tolerability of Fixed Doses of Intranasal Esketamine in Japanese Participants With Treatment Resistant Depression, ClinicalTrials.gov, Sep. 28, 2016, Esketamine, NCT02918318.
Janicak, et al., Ketamine Treatment for Major Depression, Psychopharm Review, 2011, pp. 89-96, vol. 46 Issue 12.
James Murrough., Use of Ketamine to Enhance Electroconvulsive Therapy (ECT) in Depression, ClinicalTrials.gov, Mar. 7, 2011, Ketamine, NCT01309581.
James Murrough., Intranasal Ketamine in Treatment-Resistant Depression, ClinicalTrials.gov, Feb. 25, 2011, Ketamine, NCT01304147.
James Murrough., Continuation Ketamine in Major Depression, ClinicalTrials.gov, Oct. 25, 2007, Ketamine, NCT00548964.
James Murrough, Ketamine for Suicidal Ideation, ClinicalTrials.gov, Jan. 10, 2012, Ketamine, NCT01507181.
Jafarinia, et al., Efficacy and safety of oral ketamine versus diclofenac to alleviate mild to moderate depression in chronic pain patients: A double-blind, randomized.controlled trial, Journal ofAffectiveDisorders, Jun. 1, 2016, pp. 1-8, vol. 204.
Jack Aurora., Development of Nasal Delivery systems: A Review, Drug Development & Delivery, 2017, pp. 1-4, vol. 2 Issue 7.
Jack Aurora, Development of Nasal Delivery Systems: A Review. Drug Development and Delivery. vol. 2 No. 7, Oct. 2002.
Isometsa, et al., Suicide in Major Depression, Aml Psychiatry, 1994, pp. 530-536, vol. 151 Issue 4.
Irwin, et al., Oral Ketamine for the Rapid Treatment of Depression and Anxiety in Patients Receiving Hospice Care, Journal of Palliative Medicine, Jan. 13, 2010, pp. 903-908, vol. 13 Issue 7.
Irwin, et al., Daily Oral Ketamine for the Treatment of Depression and Anxiety in Patients Receiving Hospice Care: A 28-Day Open-Label Proof-of-Concept Trial, Journal of Palliative Medicine, 2013, pp. 958-965, vol. 16 Issue 8.
Ionescu, et al., Rapid and Sustained Reductions in Current Suicidal Ideation Following Repeated Doces of Intravenous Ketamine:, J Clin Psychiatry, 2016, pp. e1-e7.
Ionescu, et al., Effect of Baseline Anxious Depression on Initial and Sustained Antidepressant Response to Ketamine, J Clin Psychiatry, 2014, pp. e932-e938, vol. 75 Issue 9.
International Search Report re: PCT/US2016/33404 dated Aug. 16, 2016.
International Search Report re: PCT/US2015/44830 dated Nov. 23, 2015.
International Search Report re: PCT/US2015/049961 dated Jan. 12, 2016.
International Search Report re: PCT/US2014/027074 dated May 27, 2014.
International Search Report re: PCT/US2014/027059 dated Jul. 16, 2014.
International Search Report re: PCT/US2013/030476 dated Apr. 24, 2013.
International Search Report re: PCT/EP2016/060922 dated Jul. 28, 2016.
Instituto Mexicano Del Seguro Social., Effect of Ketamine in Depressive Symptoms of Elderly Patients With Visual Impairment., ClinicalTrials.gov, Mar. 22, 2018, Ketamine, NCT03473431.
Inonu University., Effects of Sevoflurane and Ketamine on QT in Electroconvulsive Therapy, ClinicalTrials.gov, Jun. 6, 2013, Ketamine, NCT01870219.
Inonu University., Effect of the Addition of Ketamine to Sevoflurane Anesthesia in Electroconvulsive Therapy, ClinicalTrials.gov, Oct. 20, 2014, Ketamine, NCT02267980.
Ingrid Torjesen., Ketamine helps a third of patients with treatment resistant depression, finds small UK study, BMJ, Apr. 3, 2014, pp. 92576-92576, vol. 348.
Iglewicz, et al., Ketamine for the Treatment of Depression in Patients Receiving Hospice Care: A Retrospective Chart Review of Thirty-One Cases, Psychosomatics., 2015, pp. 329-337, vol. 56 Issue 4.
Icahn School of Medicine at Mount Sinai., MRI Studies of Emotion in Depression, ClinicalTrials.gov, Apr. 29, 2015, ketamine, NCT02429011.
Icahn School of Medicine at Mount Sinai, Treatment Study of Bipolar Depression, ClinicalTrials.gov, Jul. 28, 2009, ketamine, NCT00947791.
Icahn School of Medicine at Mount Sinai, Ketamine Plus Lithium in Treatment-Resistant Depression, ClinicalTrials.gov, Jun. 19, 2013, Ketamine, NCT01880593.
Icahn School of Medicine at Mount Sinai, Ketamine and Nitroprusside for Depression, ClinicalTrials.gov, Apr. 6, 2017, Ketamine, NCT03102736.
Ibrahim, et al., Rapid decrease in depressive symptoms with an N-methyl-d-aspartate antagonist in ECT-resistant major depression, Progress in Neuro-Psychopharmacology & Biological Psychiatry, Apr. 3, 2011, pp. 1155-1159, vol. 35.
Hyman, et al., Initiation and Adaptation : A Paradigm for Understanding Psychotropic Drug Action, Am J Psychiatry, 1996, pp. 151-162, vol. 153.
Hvidovre University Hospital., Optimal Multimodal Analgesia in Laparoscopic Cholecystectomy, ClinicalTrials. gov, Sep. 21, 2005, S-ketamine, NCT00209885.
Hvidovre University Hospital., Optimal Multimodal Analgesia in Abdominal Hysterectomy, ClinicalTrials.gov, Sep. 21, 2005, S-ketamine, NCT00209872.
Hustveit, et al., Interaction of the Chiral Forms of Ketamine with Opioid Phencyclidine, and Muscarinic Receptors, Pharmacology & Toxicology, Apr. 25, 1995, pp. 355-359, vol. 77.
Husain, et al., Speed of Response and Remission in Major Depressive Disordwer With Acute Electroconvulsive Therapy (ECT); A Consortium for Research in ECT (CORE) Report, J Clin Psychiatry, 2004, pp. 485-491, vol. 65 Issue 4.
Hunt, et al., Suicide amongst psychiatric in-patients who abscond from the ward: a national clinical survey, BMC Psychiatry, Feb. 3, 2010, pp. 1-6, vol. 10 Issue 14.
Huge V. et al., "Effects of low-dose intranasal (S)-ketamine in patients with neuropathic pain", European Journal of Pain, Saunders, London, GB, vol. 14, No. 4, Apr. 1, 2010 (Apr. 1, 2010), pp. 387-394.
Huang et al., Mechanism of Nasal Absorption of Drugs I: Physicochemical Parameters Influencing the Rate of In Situ Nasal Absorption of Drugs in Rats, Journal of Pharmaceutical Sciences, 74(6):608-611, 1985.
Hu, et al., Single i.v. ketamine augmentation of newly initiated escitalopram for major depression: results from a randomized, placebo-controlled 4-week study, Psychological Medicine, Oct. 19, 2015, pp. 623-635, vol. 46.

(56) References Cited

OTHER PUBLICATIONS

Hospital De Clinicas De Porto Alegre., Intranasal Ketamine as a Sedative for Venipuncture, ClinicalTrials.gov, Oct. 11, 2016, Ketamine, NCT02929524.
Hospira, Nowa Wholly Owned Subsidiary of Pfizer, Safety and Efficacy of Repeated Doses of PMI-150 (Intranasal Ketamine) in Acute Postoperative Pain Following Orthopedic Surgery, ClinicalTrials.gov, Jul. 3, 2008, Ketamine, NCT00709436.
Hospira, Nowa Wholly Owned Subsidiary of Pfizer, Safety and Efficacy of PMI-150 (Intranasal Ketamine) for the Treatment of Breakthrough Pain in Cancer Patients, ClinicalTrials.gov, Jun. 27, 2007, Ketamine, NCT00492388.
Horr, et al., Ketamine: A Potential Option For Treatment-Refractory Depression in Elder Adults, Conference Poster, 2014, pp. 179-179, Poster C39.
Hong, J. et al., Curr Opin Allergy Clin Immunol., 2009, pp. 447-453, 9(5).
Hong et al., Allergy to ophthalmic preservatives, Current Opinion in Allergy and Clinical Immunology, 2009, pp. 447-453, vol. 9.
Holma, et al., Incidence and Predictors of Suicide Attempts in DSM-IV Major Depressive Disorder: A Five-Year Prospective Study, Am J Psychiatry, Jan. 19, 2010, pp. 801-808, vol. 167 Issue 7.
Kellner, et al., Relief of Expressed Suicidal Intent by ECT: A Consortium for Research in ECT Study, Am J Psychiatry, 2005, pp. 972-982, vol. 162 Issue 5.
Kapur, et al., Psychiatric inpatient care and suicide in England, 1997 to 2008: a longitudinal study, Psychological Medicine, Jun. 24, 2013, pp. 61-71, vol. 43 Issue 1.
Kapur, et al., Ketamine Has Equal Affinity for NMDA Receptors and the High-Affinity State of the Dopamine 02 Receptor, Biol Psychiatry, 2001, pp. 954-957, vol. 49.
Kane, et al., Clozapine and Haloperidol in Moderately Refractory Schizophrenia, Arch Gen Psychiatry, Mar. 22, 2001, pp. 965-972, vol. 58.
Kallmunzer, et al., Treatment escalation in patients not responding to pharmacotherapy, psychotherapy, and electro-convulsive therapy: experiences from a novel regimen using intiavenous S-ketamine as add-on therapy in treatment-resistant depression, J Neural Transmz', Dec. 31, 2015, pp. 549-552, vol. 123.
Juvenile Bipolar Research Foundation., Intranasal Ketamine In the Treatment of Pediatric Bipolar Disorder (IKBP), ClinicalTrials.gov, Jan. 5, 2012, Ketamine, NCT01504659.
JP63002932 A English Translation, Jan. 1988, Translated Jan. 30, 2015.
Jonkman, et al., Pharmacokinetics and Bioavailability of Inhaled Esketamine in Healthy Volunteers., Anesthesiology, 2017, pp. 675-683, vol. 127 Issue 4.
Jon Hamilton, Ketamine, A Promising Depression Treatment, Seems to Act Like an Opioid,, www.npr.org, Aug. 29, 2018, pp. 1-8, NA.
Jokinen, et al., Karolinska Interpersonal Violence Scale Predicts Suicide in Suicide Attemptsrs, J Clin Psychiatry, Mar. 16, 2010, pp. 1025-1032, vol. 71 Issue 8.
Johnson & Johnson Pharmaceutical Research & Development, L.L.C.., The Effect of Ketamine on Attentiveness, ClinicalTrials.gov, Jul. 19, 2010, Ketamine, NCT01165294.
Johansson J. et al., "Prehospital analgesia using nasal administration of S-ketamine—a case series", Scandinavian Journal of Trauma, Resuscitation and Emergency Medicine, Biomed Central Ltd, London UK, vol. 21, No. 38, May 14, 2013 (May 14, 2013), pp. 1-4.
Johansson et al., Prehospital analgesia using nasal administration of S-ketamine-a case series, Scandinavian Journal of Trauma, 2013, pp. 1-5, vol. 21 Issue 38, BioMed Central Ltd.
Jick, et al., Antidepressants and the Risk of Suicidal Behaviors, JAMA, Jul. 21, 2004, pp. 338-343, vol. 292 Issue 3.
Javelin Pharmaceuticals., Multiple Dose Pharmacokinetics of Intranasal Ketamine, ClinicalTrials.gov, Aug. 23, 2007, Ketamine, NCT00519987.
Javelin Pharmaceuticals., Determination of Drug Interactions of Certain Nasal Medications With Intranasal Ketamine, ClinicalTrials.gov, Aug. 23, 2007, Ketamine, NCT00520104.
Javelin Pharmaceuticals., Assessing the Effects of a Nasal Corticosteroid on PMI-150 (Intranasal Ketamine), ClinicalTrials.gov, Apr. 21, 2008, Ketamine, NCT00662883.
Javelin Pharmaceuticals., Absolute Bioavailability and Nasopharyngeal Absorption of Intranasal Ketamine, ClinicalTrials.gov, Aug. 23, 2007, ketamine, NCT00520169.
Javelin Pharmaceuticals, Safety and Efficacy of Intranasal Ketamine for the Treatment of Postoperative Dental Pain, ClinicalTrials.gov, Jun. 20, 2007, Ketamine, NCT00488787.
Jason McMullan., Intranasal Ketamine as an Adjunct to Fentanyl for the Prehospital Treatment of Acute Traumatic Pain, ClinicalTrials.gov, Aug. 15, 2016, Ketamine, NCT02866071.
Janssen Research & Development, LLC., The Effect of Minocycline on Relapse After Successful Intravenous Ketamine/Minocyclineinduced Symptoms Response in Subjects With Depression, ClinicalTrials.gov, Mar. 12, 2013, Ketamine, NCT01809340.
Janssen Research & Development, LLC., Study to Assess the Effects of Esketamine on Safety of On-road Driving in Healthy Participants (DRiVESaFe), ClinicalTrials.gov, Aug. 28, 2014, Esketamine, NCT02228239.
Janssen Research & Development, LLC., Study to Assess the Effects of Allergic Rhinitis and Co-administration of Mometasone or Oxymetazoline on the Pharmacokinetics, Safety, and Tolerability of Intranasal Esketamine, ClinicalTrials.gov, Jun. 3, 2014, Esketamine, NCT02154334.
Janssen Research & Development, LLC., Pharmacokinetic Study of Intranasal Esketamine and Its Effects on the Pharmacokinetics of Orally-Administered Midazolam and Bupropion in Healthy Participants, ClinicalTrials.gov, Oct. 5, 2015, Esketamine, NCT02568176.
Janssen Research & Development, LLC., Crossover Study to Evaluate the Abuse Potential of Intranasal Esketamine Compared to Racemic Intravenous Ketamine in Nondependent, Recreational Drug Users, ClinicalTrials.gov, Feb. 15, 2016, Esketamine, NCT02682225.
Janssen Research & Development, LLC., A Study to Investigate Evoked Potentials as Markers of Ketamine-induced Cortical Plasticity in Patients With Major Depressive Disorder, ClinicalTrials.gov, Oct. 8, 2013, Ketamine, NCT01957410.
Janssen Research & Development, LLC., A Study to Evaluate the Safety and Efficacy of Intranasal Esketamine in Treatmentresistant Depression (SYNAPSE), ClinicalTrials.gov, Dec. 3, 2013, Esketamine, NCT01998958.
Janssen Research & Development, LLC., A Study to Evaluate the Pharmacokinetics of Intranasal Esketamine Administered With and Without a Nasal Guide on the Intranasal Device, ClinicalTrials.gov, Feb. 12, 2014, Esketamine, NCT02060929.
Janssen Research & Development, LLC., A Study to Evaluate the Efficacy, Safety, and Tolerability of Intranasal Esketamine Plus an Oral Antidepressant in Elderly Participants With Treatment-resistant Depression (TRANSFORM-3), ClinicalTrials.gov, Apr. 21, 2015, Esketamine, NCT02422186.
Janssen Research & Development, LLC., A Study to Evaluate the Efficacy, Safety, and Tolerability of Fixed Doses of Intranasal Esketamine Plus an Oral Antidepressant in Adult Participants With Treatment-resistant Depression (TRANSFORM-1), ClinicalTrials.gov, Apr. 15, 2015, Esketamine, NCT02417064.
Janssen Research & Development, LLC., A Study to Evaluate the Efficacy, Pharmacokinetics, Safety and Tolerability of Flexible Doses of Intranasal Esketamine Plus an Oral Antidepressant in Adult Participants With Treatment-resistant Depression, ClinicalTrials.gov, Feb. 15, 2018, Esketamine, NCT03434041.
Janssen Research & Development, LLC., A Study to Evaluate the Efficacy and Safety of Intranasal Esketamine in Addition to Comprehensive Standard of Care for the Rapid . . . , ClinicalTrials.gov, Mar. 31, 2017, Esketamine, NCT03097133.
Janssen Research & Development, LLC., A Study to Evaluate the Effects of Esketamine on Cardiac Repolarization in Healthy Participants, ClinicalTrials.gov, Apr. 14, 2016, Esketamine, NCT02737605.
Janssen Research & Development, LLC., A Study to Evaluate the Effect of Intranasal Esketamine on Cognitive Functioning in Healthy Subjects, ClinicalTrials.gov, Mar. 21, 2014, Esketamine, NCT02094378.
Janssen Research & Development, LLC., A Study to Assess the Pharmacokinetics, Safety, and Tolerability of Intranasally Admin-

(56) References Cited

OTHER PUBLICATIONS istered Esketamine in Healthy Participants, ClinicalTrials.gov, Jan. 31, 2013, Esketamine, NCT01780259.
Janssen Research & Development, LLC., A Study to Assess the Pharmacokinetics of Intranasally Administered Esketamine in Healthy Japanese and Caucasian Volunteers, ClinicalTrials.gov, Nov. 8, 2013, Esketamine, NCT01980303.
Janssen Research & Development, LLC., A Study to Assess the Effects of Renal Impairment on the Pharmacokinetics, Safety, and Tolerability of Intranasally Administered Esketamine, ClinicalTrials.gov, Nov. 17, 2015, Esketamine, NCT02606084.
Janssen Research & Development, LLC., A Study to Assess the Effect of Ticlopidine on the Pharmacokinetics, Safety, and Tolerability of Intranasally Administered Esketamine in Healthy Participants, ClinicalTrials.gov, Oct. 2, 2017, Esketamine, NCT03298906.
Janssen Research & Development, LLC., A Study of Ketamine in Patients With Treatment-resistant Depression, ClinicalTrials.gov, Jun. 26, 2012, ketamine, NCT01627782.
Janssen Research & Development, LLC., A Pharmacokinetic, Safety and Tolerability Study of Esketamine in Healthy Elderly and Adult Participants, ClinicalTrials.gov, May 2, 2014, Esketamine, NCT02129088.
Janssen Research & Development, LLC., A Long-term Safety Study of Intranasal Esketamine in Treatment-resistant Depression (SUSTAIN-3), ClinicalTrials.gov, May 25, 2016, Esketamine, NCT02782104.
Janssen Research & Development, LLC, Study to Evaluate the Efficacy and Safety of 3 Fixed Doses of Intranasal Esketamine in Addition to Comprehensive Standard of Care for the Rapid Reduction of the Symptoms of Major Depressive Disorder, Including Suicidal Ideation . . . , ClinicalTrials.gov, Jun. 14, 2017, Esketamine, NCT03185819.
Janssen Research & Development, LLC, Pharmacokinetic, Safety, and Tolerability Study of Intranasally Administered Esketamine in Elderly and and Healthy Younger Adult Participants, ClinicalTrials.gov, Jan. 26, 2015, Esketamine, NCT02345148.
Janssen Research & Development, LLC, A Study to Evaluate the Efficacy, Safety, and Tolerability of Flexible Doses of Intranasal Esketamine Plus an Oral Antidepressant in Adult Participants With Treatment-resistant Depression (TRANSFORM-2), ClinicalTrials.gov, Apr. 16, 2015, Esketamine, NCT02418585.
Janssen Research & Development, LLC, A Study to Evaluate the Effects of a Single-Dose and Repeat-Administration of Intranasal Esketamine on On-Road Driving in Participants With Major Depressive Disorder (DriveSaFe2), ClinicalTrials.gov, Sep. 29, 2016, Esketamine, NCT02919579.
Janssen Research & Development, LLC, A Study to Evaluate the Absolute Bioavailability of Intranasal and Oral Esketamine and the Effects of Clarithromycin on the Pharmacokinetics of Intranasal Esketamine in Healthy Participants, ClinicalTrials.gov, Jan. 21, 2015, Esketamine, NCT02343289.
Janssen Research & Development, LLC, A Study to Assess the Effects of Hepatic Impairment on the Pharmacokinetics, Safety, and Tolerability of Intranasally Administered Esketamine, ClinicalTrials.gov, Nov. 20, 2015, Esketamine, NCT02611505.
Janssen Research & Development, LLC, A Study of the Efficacy of Intravenous Esketamine in Adult Patients With Treatment-Resistant Depression, ClinicalTrials.gov, Jul. 13, 2012, Esketamine, NCT01640080.
Janssen Research & Development, LLC, A Study of the Efficacy and Safety of Intranasal Esketamine in the Rapid Reduction of Symptoms of Major Depressive Disorder, in Adult at Imminent Risk for Suicide (Aspire I), ClinicalTrials.gov, Feb. 1, 2017, Esketamine, NCT03039192.
Janssen Research & Development, LLC, A Study of Intranasal Esketamine Plus an Oral Antidepressant for Relapse Prevention in Adult Participants With Treatment-resistant Depression (SUSTAIN-1), ClinicalTrials.gov, Jul. 10, 2015, Esketamine, NCT02493868.
Ho, C.Y. et al., Am J Rhinol., 2008, pp. 125-129, 22(2).

Ho et al., In vitro effects of preservatives in nasal sprays on human nasal epithelial cells, American Journal of Rhinology, 2008, pp. 125-129, vol. 22.
Hijazi et al., Stability of Ketamine and Its Metabolites Norketamine and Dehydronorketamine in Human Biological Samples, Clinical Chemistry 47(9):1713-1715, 2001.
Helsinki University., Psilocybin and Depression (Psilo101), ClinicalTrials.gov, Dec. 21, 2017, ketamine, NCT03380442.
Hedlund, et al., The Hamilton Rating Scale for Depression A Comprehensive Review, Journal of Operational Psychiatry, 1979, pp. 150-165, vol. 10 Issue 2.
Healthcare Quality Report., Highlights From the 2012 National Healthcare Quality and Disparities Reports, Healthcare Quality Report, 2013, pp. 1-212, AHRQ Publication No. 13-0002.
Hassamal, et al., Augmentation Therapy With Serial Intravenous Ketamine Over 18 Months in a Patient With Treatment Resistant Depression, Clin Neuropharm, 2015, pp. 212-216, vol. 38 Issue 5.
Harold A. Sackeim, Ph.D., The Definition and Meaning of Treatment-Resistant Depression, J Clin Psychiatry, 2001, pp. 10-17, vol. 62 Issue 16.
Harihar, et al., Intramuscular ketamine in acute depression: A report on two cases, Indian Journal of Psychiatry, 2013, pp. 186-188, vol. 55 Issue 2.
Hamilton, Hamilton Depression Rating Scale (HAM-D), M. Journal of Neurology, Neurosurgery, and Psychiatry, 1960, pp. 56-62, vol. 23.
Gutzke, et al., Cardiac Transplantation: A Prospective Comparsion of Ketamine and sufentanil for Anesthetic Induction, Journal of Cardiothoracic Anesthesia, 1989, pp. 389-395, vol. 3 Issue 4.
Gurnan, et al., Role of Ketamine in Severe Depression with suicidal ideation—Insights from a Case Study, Asian Journal of Psychiatry, Apr. 12, 2017, pp. 112-113, vol. 29.
Guangzhou Women and Children's Medical Center., Intranasal Ketamine With Dexmedetomidine for the Treatment of Children With Autism Spectrum Disorder, ClinicalTrials.gov, Feb. 15, 2018, Ketamine, NCT03434366.
Gosek, et al., Effectiveness of ketamine in depressed patients resistant to ECT or rTMS therapy, Psychiatr. Pol, 2014, pp. 49-58, vol. 48 Issue 1.
Gonzalo Laje et al: "Brain-Derived Neurotrophic Factor Val66Met Polymorphism and Antidepressant Efficacy of Ketamine in Depressed Patients", Biol Psychiatry , vol. 72, No. 11, Dec. 1, 2012 (Dec. 1, 2012), pages e27-e28.
Gomes et al., Neurotoxicity of Subarachnoid Preservative-Free S (+)-Ketamine in Dogs, Pain Physician, 14:83-90, 2011.
Gliatio, et al., Evaluation and Treatment of Patients with Suicidal Ideation, American Family Physician, Mar. 15, 1999, pp. 1500-1506, vol. 59 Issue 6.
Ghasemi, et al., Rapid antidepressant effects of repeated doses of ketamine compared with electroconvulsive therapy in hospitalized patients with major depressive disorder, Psychiatry Research, Dec. 13, 2013, pp. 355-361, vol. 215.
George, et al., Pilot Randomized Controlled Trial of Titrated Subcutaneous Ketamine in Older Patients with Treatment-Resistant Depression, Am J Geriatr Psychiatry, 2017, pp. 1-11.
GENBANK_AC099753, *Homo sapiens* chromosome 3 clone RP11-466A13, complete sequence. Mar. 20, 2002, [online]. [Retrieved on Oct. 1, 2015], Retrieved from the Internet: <URL: http://www.ncbi.nlm.nih.gov/nuccore/19551144/> PDF file: p. 1-40. p. 1, Definition; p. 3, Origin, p. 27, the nucleotide sequence between 113924-112924, especially the nucleotides between 113.444-113405; and the nucleotide at the position of 113424.
Garcia, et al., Olfactory deposition of inhaled nanoparticles in humans, Inhalation Toxicology, Jul. 21, 2015, pp. 394-403, vol. 27 Issue 8.
Galveza, et al., Long-Lasting Effects of a Single Subcutaneous Dose of Ketamine for Treating Melancholic Depression: A Case Report, Biol Psychiatry, 2014, pp. e1-e2, vol. 76.
Galvez, et al., Repeated intranasal Ketamine for treatment-resistant depression-the way to go? Results from a pilot randomised controlled trail, Journal of Psychopharmacology, 2018, pp. 1-11.
Friedberg, et al., Hypnosis First, Then Dissociation, Anesth Analg, 2003, pp. 913-914, vol. 96.

(56) References Cited

OTHER PUBLICATIONS

Frank, et al., Conceptualization and Rationale for Consensus Definitions of Terms in Major Depressive Disorder, Arch Gen Psychiatry, 1991, pp. 851-855, vol. 48.
Ford, et al., Benzodiazepines may reduce the effectiveness of ketamine in the treatment of depression, Australian & New Zealand Journal of Psychiatry, 2015, pp. 1-1.
Fondation Lenval., Intranasal Ketamine and Fracture Reduction in Pediatric Emergencies (KETAPED) (KETAPED), ClinicalTrials.gov, May 16, 2018, Ketamine, NCT03525821.
First Affiliated Hospital of Chongqing Medical University., Effect of Subanesthetic Dose of Ketamine Combined With Propofol on Cognitive Function in Depressive Patients Undergoing Electroconvulsive Therapy, ClinicalTrials.gov, Dec. 2, 2014, ketamine, NCT02305394.
Feifel, et al., Low-dose ketamine for treatment resistant depression in an academic clinical practice setting, Journal of Affective Disorders, Jun. 20, 2017, pp. 283-288, vol. 221.
Fastner, et al., Intravenous S-Ketamine Does Not Inhibit Alveolar Fluid Clearance in a Septic Rat Model, PLOS ONE, Nov. 11, 2014, pp. 1-9, vol. 9 Issue 11.
Fan, et al., Profiling the psychotic, depressive and anxiety symptoms in chronic ketamine users, Psychiatry Research, Jan. 14, 2016, pp. 311-315, vol. 237.
Fan, et al., Ketamine rapidly relieves acute suicidal ideation in cancer patients: a randomized controlled clinical trial, Oncotarget, Dec. 1, 2016, pp. 2356-2360, vol. 8 Issue 2.
Evelyne D.Troitter., Pain Free Laceration Repairs Using Intra-nasal Ketamine, ClinicalTrials.gov, Feb. 15, 2017, Ketamine, NCT03053947.
Essentia Health., Ketamine Frequency Treatment for Major Depressive Disorder, ClinicalTrials.gov, Mar. 28, 2008, Ketamine, NCT00646087.
Erasme University Hospital, Respiratory Depression During an Analgosedation Combining Remifentanil and Ketamine in TCI for Oocyte Retrieval, ClinicalTrials.gov, Mar. 8, 2018, ketamine, NCT03458143.
Entsuah, et al., Response and Remission Rates in Different Subpopulations With Major Depressive Disorder Administered Venlafaxine, Selective Serotonin Reuptake Inhibitors, or Placebo, J Clin Psychiatry, 2001, pp. 869-877, vol. 62 Issue 11.
Emory University., Intranasal (NAS) Ketamine for Cancer Pain, ClinicalTrials.gov, May 10, 2017, Ketamine, NCT03146806.
Emory University., Heart Rate Variability in Depression, ClinicalTrials.gov, Aug. 18, 2015, Depressive Disorder, NCT02525978.
Ellioti, et al., N-Methyl-D-Aspartate (NMDA) Receptors, Mu and Kapp.a Opioid Tolerance, and Perspectives on New Analgesic Drug Development, Neuropsychopharmacology, May 3, 1995, pp. 347-356, vol. 13 Issue 4.
Elie Dolgin., The Ultimate Endpoint, Nature Medicine, 2012, pp. 190-194, vol. 18 Issue 2.
Duncan, et al., Baseline delta sleep ratio predicts acute ketamine mood response in major depressive disorder, Journal of Affective Disorders, Aug. 5, 2012, pp. 115-119, vol. 145.
Duman, et al., Synaptic plasticity and mood disorders, Molecular Psychiatry, 2002, pp. 1-11, vol. 7 Issue 1.
Duman, et al., Synaptic Dysfunction in Depression: Potential Therapeutic Targets, Science, Oct. 5, 2012, pp. 68-72, vol. 338.
Drevets, et al., Amphetamine-Induced Dopamine Release in Human Ventral Striatum Correlates with Euphoria, Biol Pschiatry, 2001, pp. 81-96, vol. 49.
Draft Guidance., Guidance for Industry Suicidal Ideation and Behavior: Prospective Assessment of Occurrence in Clinical Trials, Clinical/Medical, 2012, pp. 1-16, Revision 1.
Dougals, et al., Practice Guideline for the Assessment and Treatment of Patients With Suicidal Behaviors, American Psychiatric Association Practice Guidelines, Jul. 28, 2003, pp. 1-120.
Donn W Ketcham MD., Where there is no anaesthesiologist; the many usus of ketamine, Tropical Doctor, 1990, pp. 163-166, vol. 20.
Domino, et al., Pharmacologic effects of CI-581, a new dissociative anesthetic, in man, Clinical Pharmacology and Therapeutics, Jan. 4, 1965, pp. 279-291, vol. 6 Issue 3.

Djupesland, et al., Breath Powered Nasal Delivery: A New Route to Rapid Headache Relief, Headache, Jun. 4, 2013, pp. 72-84, vol. 53 Supplementary 2.
Aiphs, et al., Comparative Validation of the ISST-Plus, the S-STS, and the C-SSRS for Assessing Suicidal Thinking and Behavior When Mapped to C-CASA (2010), Janssen Scientific Affairs, LLC, 2012, pp. 1-1, Poster.
Ahn, et al., Proliposomes as an intranasal dosage form for the sustained delivery of propranolol, Journal of Controlled Release, Oct. 13, 1994, pp. 203-210, vol. 34.
Adhvaryu, et al., Short Communication Genotoxic efforts of Ketamine on CHO cells, Arch Toxicol, Apr. 3, 1986, pp. 124-125, vol. 59.
Abdallah, et al., The Rapid Antidepressant Effect of Ketamine in the Electroconvulsive Therapy Setting, J ECT, 2012, pp. 157-161, vol. 28 Issue 3.
Abdallah, et al., The Nucleus Accumbens and Ketamine Treatment in Major Depressive Disorder, Neuropsychopharmacology, Mar. 29, 2017, pp. 1739-1746, vol. 42.
Abdallah, et al., Ketamine Treatment and Global Brain Connectivity in Major Depression, Neuropsychopharmacology, 2017, pp. 1210-1219, vol. 42.
Abdallah, et al., Hippocampal volume and the rapid antidepressant effect of ketamine, Journal of Psychopharmacology, 2015, pp. 591-595, vol. 29 Issue 5.
Abdallah, et al., ECT Attenuates the Rapid Antidepressant Effect of Ketamine, Biol Psychiatry, 2012, pp. 294S, vol. 71.
Aan Het Rot, et al., Safety and Efficacy of Repeated-Dose Intravenous Ketamine for Treatment-Resistant Depression, Biol Psychiatry, Aug. 27, 2009, pp. 139-145, vol. 67.
AACAP Official Action., Practice Parameter for the Assessment and Treatment of Children and Adolescents With Suicidal Behavior, J. Am. Acad. Child Adolesc. Psychiatry, 2001, pp. 24S-51S, vol. 40 Supplementary 7.
United States Naval Medical Center, San Diego., Subanesthetic IV Bolus Ketamine in the Treatment of Acute Depression, ClinicalTrials.gov, Mar. 4, 2015, Ketamine, NCT02378415.
United States Naval Medical Center, San Diego., A Study to Decrease Suicidal Thinking Using Ketamine, ClinicalTrials.gov, Apr. 16, 2015, Ketamine, NCT02418702.
UN Economic Social Council., Changes in the scope of control of substances Note by the Secretariat, UN Economic Social Council, Dec. 16, 2014, pp. 1-15.
UN Convention_Psychotropic Substances, UN Convention Psychotropic Substances, 1971, pp. 1-28.
Udo Bonnett, M.D., Long-Term Ketamine Self-Injections in Major Depressive Disorder: Focus on Tolerance in Ketamine's Antidepressant Response and the Development of Ketamine Addiction, Journal of Psychoactive Drugs, 2015, pp. 276-285, vol. 47 Issue 4.
Turku University Hospital, Dose-response of Ketamine in Patient Controlled Analgesia in Orthopaedic Surgery Patients (DoseRespKeta). ClinicalTrials.gov, Dec. 15, 2016, S-Ketamine, NCT02994173.
Trullas, et al., Functional antagonists at the NMDA receptor complex exhibit antidepressant actions, European Journal of Pharmacology, May 29, 1990, pp. 1-10, vol. 185.
Trivedi, et al., Evaluation of Outcomes With Citalopram for Depression Using Measurement-Based Care in STAR*D: Implications for Clinical Practice, Am J Psychiatry, 2006, pp. 28-40, vol. 163 Issue 1.
Trevithick, et al., Study protocol for the randomised controlled trial: Ketamine augmentation of ECT to improve outcomes in depression (Ketamine-ECT study), Trevithick et al. BMC Psychiatry, 2015, pp. 1-11, vol. 15 Issue 257.
Thomas P. Laughren, Comorbid Mood Disorders and Medical Illness: A Food and Drug Administration Perspective, Biol Psychiatry, 2003, pp. 195-199, vol. 53.
The University of Texas Health Science Center, Houston., The UTHealth Ketamine Project, ClinicalTrials.gov, Aug. 30, 2016, Ketamine, NCT02882711.
The University of Texas Health Science Center, Houston., Low Dose Intravenous Ketamine in Treatment Resistant Depression Patients (ketamine), ClinicalTrials.gov, Oct. 17, 2016, Ketamine, NCT02935595.

(56) References Cited

OTHER PUBLICATIONS

The University of Texas Health Science Center, Houston, Trial of the Rapid Antisuicidal Effects of Intranasal Ketamine in Comorbid Depression and Alcohol Abuse, ClinicalTrials.gov, May 28, 2018, Ketamine, NCT03539887.

The University of Texas Health Science Center at San Antonio., Effects of Low Dose Ketamine Given at Induction of Anesthesia on Postoperative Mood in Patients With Depressive Symptoms, ClinicalTrials.gov, Apr. 21, 2015, Ketamine, NCT02422303.

The University of New South Wales., Ketamine Trial for the Treatment of Depression, ClinicalTrials.gov, Mar. 27, 2015, Ketamine, NCT02401139.

The University of New South Wales, A Study of Ketamine as an Antidepressant, ClinicalTrials.gov, Sep. 27, 2011, Ketamine, NCT01441505.

The Neuroscience Center, LLC., Neuromodulation to Facilitate the Effect of Ketamine (TMS/ketamine), ClinicalTrials.gov, Mar. 22, 2013, Ketamine, NCT01816958.

The Cleveland Clinic., Administration of Subanesthetic Dose of Ketamine and Electroconvulsive Treatment for Treatment Resistant Depression, ClinicalTrials.gov, Aug. 13, 2015, Ketamine, NCT02522377.

The Cleveland Clinic, ELEKT-D: Electroconvulsive Therapy (ECT) vs. Ketamine in Patients With Treatment Resistant Depression (TRD) (ELEKT-D), ClinicalTrials.gov, Apr. 14, 2017, Ketamine, NCT03113968.

Thase, et al., When at First You Dont Succeed: Sequential Strategies for Antidepressant Nonresponders, J Clin Psychiatry, 1997, pp. 23-29, vol. 58 Supplementary 13.

Thase, et al., Remission Rates Following Antidepressant Therapy With Bupropion or Selective Serotonin Reuptake Inhibitors: A Meta-Analysis of Original Data From 7 Randomized Controlled Trials, J Clin Psychiatry, 2005, pp. 974-981, vol. 66 Issue 8.

Tel-Aviv Sourasky Medical Center., Oral Ketamine for Suicidal Ideation, ClinicalTrials.gov, Jan. 16, 2014, Ketamine, NCT02037503.

Tel Aviv Medical Center., Intranasal Ketamine for Acute Traumatic Pain, ClinicalTrials.gov, Jun. 29, 2016, Ketamine, NCT02817477.

Technische Universitat Monchen, Anesthetics and Auditory, Visceral, and Heat Evoked Potentials, ClinicalTrials.gov, Sep. 26, 2007, S-Ketamine, NCT00534586.

TC Erciyes University, Intranasal Dexmedetomidine vs Midazolam-ketamine Combination for Premedication of Pediatric Patients, ClinicalTrials.gov, Feb. 26, 2014, ketamine, NCT02072083.

Tansey et al., Contribution of Common Genetic Variants to Antidepressant Response, Biol Psychiatry, 2013, pp. 679-682, 73.

Tampere University Hospital., Inhaled Nebulised S(+)-Ketamine for Postoperative Analgesia, ClinicalTrials.gov, Mar. 24, 2015, Ketamine, NCT02397356.

Szymkowicza, et al., A 12-month naturalistic observation of three patients receiving repeat intravenous ketamine infusions for their treatment resistant depression, J Affect Disord, 2013, pp. 1-11, vol. 147.

Sunnybrook Health Sciences Centre, Effect of Ketamine vs. Active Placebo on Suicidal Ideation in Depressed Inpatients With Major Depressive Disorder or Bipolar Depression., ClinicalTrials.gov, Nov. 2, 2015, Ketamine, NCT02593643.

Su, et al., Dose-Related Effects of Adjunctive Ketamine in Taiwanese Patients with Treatment-Resistant Depression, Neuropsychopharmacology, May 11, 2017, pp. 2482-2492, vol. 42.

Straiko, et al., Lithium Protects Against Anesthesia-Induced Developmental Neuroapoptosis, Anesthesiology, 2009, pp. 862-868, vol. 110 Issue 4.

Stevenson, Ketamine: A Review, Update in Anaesthesia, 20:25-29, 2005.

Steven Richard Devore Best., Combined ketamine and transcranial magnetic stimulation for treatment resistant depression in the context of chronic OCD: a case report, Devore Best Neuropsychiatric Electrophysiology, 2015, pp. 1-4, vol. 1 Issue 2.

Steven R. Devore Best., Rapid Relief of Treatment Resistant Depression by Facilitated Ketamine Infusion: A Preliminary Report, Activitas Nervosa Superior, Jun. 28, 2014, pp. 28-36, vol. 56, Issue 1-2.

Stannard, et al., Ketamine hydrochloride in the treatment of phantom limb pain, Pain, Apr. 12, 1993, pp. 227-230, vol. 54.

Stanford University., Assessing the Effectiveness of Psychiatric Interventions on the Inpatient Unit, ClinicalTrials.gov, Aug. 10, 2018, Ketamine, NCT03626142.

Stanford University, Double-Blind Trial of Ketamine Therapy Plus or Minus Naltrexone in Treatment Resistant Depression (TRD) (Ket_Nal), ClinicalTrials.gov, Sep. 22, 2016, Naltrexone, NCT02911597.

St Patrick's Hospital, Ireland., Ketamine for Relapse Prevention in Recurrent Depressive Disorder (KINDRED), ClinicalTrials.gov, Jan. 22, 2016, Ketamine, NCT02661061.

St Patrick's Hospital, Ireland., Ketamine for Depression Relapse Prevention Following ECT (KEEP-WELL), ClinicalTrials.gov, Apr. 13, 2015, Ketamine, NCT02414932.

St Patrick's Hospital, Ireland., Ketamine as an Adjunctive Therapy for Major Depression (KARMA-dep), ClinicalTrials.gov, Aug. 21, 2017, Ketamine, NCT03256162.

Srivastava, et al., Safety and efficacy of ketamine infusion in late onset depression, and conversion to treatment response, Indian J Psychiatry, 2015, pp. 328-329, vol. 57 Issue 3.

Sos, et al., Relationship of ketamine's antidepressant and psychotomimetic effects in unipolar depression, Activitas Nervosa Superior Rediviva, Aug. 30, 2013, pp. 57-63, vol. 55 Issue 1-2.

Soni.et al., Safety assessment of propyl paraben: a review of the published literature, Food and Chemical Toxicology, Sep. 25, 2000, pp. 513-532, vol. 39, Elsevier Science LTD.

Soni, M.G. et al., Food Chem Toxicol., 2005, pp. 985-1015, 43(7).

Soni, M.G. et al., Food Chem Toxicol., 2001, pp. 513-532, 39(6).

Soni, et al., Safety assessment of esters of p-hydroxybenzoic acid parabens, Food and Chemical Toxicology, Jan. 31, 2005, pp. 985-1015, vol. 43=.

Sofia, et al., Evaluation of Ketamine HCL for Anti-Depressant Activity, Arch. int. Pharmacodyn., 1975, pp. 68-74, vol. 214.

Smith, et al., Properties of the Optical Isomers and Metabolites of Ketamine on the High Affinity Transport and Catabolism of Monoamines, Neuropharmacology, 1981, pp. 391-396, vol. 20.

Skolnick et al., Glutamate-based antidepressants: 20 years on, Trends in Pharmacological Sciences, 2006, pp. 563-569, vol. 30 Issue 11.

Skolnick, et al., Modulation of glutamate receptors: Strategies for the development of novel antidepressants, Amino Acids, Jun. 17, 2002, pp. 153-159, vol. 23.

Vranken, et al., Neuropathological findings after continuous intrathecal administration of S(C)-ketamine for the management of neuropathic cancer pain, Pain, Jun. 13, 2005, pp. 231-235, vol. 117.

Vos, et al., Years lived with disability (YLDs) for 1160 sequelae of 289 diseases and injuries 1990-2010: a systematic analysis for the Global Burden of Disease Study 2010, Lancet, Dec. 29, 2012, pp. 2163-2196, vol. 380.

Voort, et al., Continuation phase intravenous ketamine in adults with treatment-resistant depression, Journal of Affective Disorders, Sep. 12, 2016, pp. 300-304, vol. 206.

Vitiello, et al., Depressive Symptoms and Clinical Status during the Treatment of Adolescent Suicide Attempters Study (TASA), Am Acad Child Adolesc Psychiatry, 2009, pp. 997-1004, vol. 48 Issue 10.

Venancio, et al., Impaired Spatial Memory after Ketamine Administration in Chronic Low Doses, Current Neuropharmacology, 2011, pp. 251-255, vol. 9 Issue 1.

Valois., Unit-Dose Nasal Sprays:, Valois., 2004, pp. 1-2.

VA Puget Sound Health Care System., Ketamine Anesthesia for Improvement of Depression in ECT (KAID), ClinicalTrials.gov, Apr. 27, 2016, Ketamine, NCT02752724.

VA Office of Research and Development., Ketamine for Treatment Resistant Late-Life Depression, ClinicalTrials.gov, Sep. 22, 2015, Ketamine, NCT02556606.

VA Office of Research and Development, Ketamine for the Rapid Treatment of Major Depressive Disorder and Alcohol Use Disorder, ClinicalTrials.gov, Jun. 3, 2015, Ketamine, NCT02461927.

(56) References Cited

OTHER PUBLICATIONS

VA Office of Research and Development, Efficacy of Repeated Ketamine Infusions for Treatment-resistant Depression, ClinicalTrials. gov, Feb. 10, 2015, Ketamine, NCT02360280.
VA Connecticut Healthcare System., Open Label Ketamine Treatment for Major Depressive Disorder in Veterans (Ket-MOD), ClinicalTrials.gov, Feb. 15, 2017, Ketamine, NCT03053830.
University of Utah., Endogenous Opioid Modulation by Ketamine, ClinicalTrials.gov, Feb. 14, 2017, Ketamine, NCT03051945.
University of Turku, The Neural Mechanisms of Anesthesia and Human Consciousness (Part 6), ClinicalTrials.gov, Dec. 8, 2015, S-ketamine, NCT02624401.
University of Tennessee Health Science Center., IN Ketamine Vs IN Midazolam and Fentanyl for Abscess I&D, ClinicalTrials.gov, Dec. 18, 2015, Ketamine, NCT02635282.
University of Saskatchewan., ECT With Ketamine Anesthesia vs High Intensity Ketamine With ECT Rescue for Treatment-Resistant Depression, ClinicalTrials gov, Sep. 5, 2017, Ketamine, NCT03272698.
University of Saskatchewan., Comparing Ketamine and Propofol Anesthesia for Electroconvulsive Therapy, ClinicalTrials.gov, Sep. 4, 2013, Ketamine, NCT01935115.
University of Saskatchewan., Efficacy of Opioid-free Anesthesia in Reducing Postoperative Respiratory Depression in Children Undergoing Tonsillectomy, ClinicalTrials.gov, Dec. 9, 2016, Ketamine, NCT02987985.
University of Pennsylvania., Alternative Sedation During Bronchoscopy (DEX), ClinicalTrials.gov, Jul. 8, 2010, ketamine, NCT01158820.
University of Padova., Ketamine in Bariatric Surgery, ClinicalTrials. gov, Nov. 12, 2012, Ketamine, NCT01724983.
University of Ottawa., Action of Ketamine in Treatment-Resistant Depression, ClinicalTrials.gov, Sep. 18, 2013, Ketamine, NCT01945047.
University of New Mexico., Spreading Depolarization and Ketamine Supp.ression (SAKS), ClinicalTrials.gov, Jul. 17, 2015, Ketamine, NCT02501941.
University of Monastir., Ketamine Intra Nasal Traumatology (Ket), ClinicalTrials.gov, Jul. 28, 2017, Ketamine, NCT03233035.
University of Mississippi Medical Center., Ketamine: Its Effects on Suicidal Ideations and Inpatient Hospital Length of Stay, ClinicalTrials. gov, Dec. 20, 2016, Ketamine, NCT02997722.
University of Minnesota, Ketamine in Adolescents With Treatment-Resistant Depression, ClinicalTrials.gov, Mar. 5, 2014, Ketamine, NCT02078817.
University of Michigan, Relationship Between Postpartum Mood Disordersand Delivery Experience, ClinicalTrials.gov, Dec. 29, 2016, Postpartum Period, NCT03004872.
University of Michigan, Anesthesia and Functional Connectivity: An Analysis of fMRI Changes, ClinicalTrials.gov, Jul. 22, 2014, Anesthetics, NCT02196259.
University of Massachusetts, Worcester., Memantine Augmentation of Antidepressants, ClinicalTrials.gov, Jun. 27, 2006, memantine, NCT00344682.
University of Manitoba, Hyperventilation Combined With Etomidate or Ketamine Anesthesia in ECT Treatment of Major Depression, ClinicalTrials.gov, Oct. 5, 2016, Ketamine, NCT02924090.
University of Iowa., Intranasal Ketamine Versus Intramuscular Ketamine for Procedural Sedation in Pediatric Patients, ClinicalTrials. gov, Jul. 27, 2010, Ketamine, NCT01170247.
University of Glasgow., Ketamine Hydrochloride and Best Pain Management in Treating Cancer Patients With Neuropathic Pain, ClinicalTrials.gov, Mar. 16, 2011, Ketamine, NCT01316744.
University of Cincinnati., Emergency Ketamine Treatment of Suicidal Ideation, ClinicalTrials.gov, Jul. 8, 2014, Ketamine, NCT02183272.
University of California, Los Angeles., Biomarkers of Fast Acting Therapies in Major Depression, ClinicalTrials.gov, Jun. 17, 2014, Ketamine, NCT02165449.
University of California, Davis, ED Treatment of Suicidal Patients With Ketamine Infusion, ClinicalTrials.gov, Apr. 18, 2018, Ketamine, NCT03502551.
University of Calgary., Pre-hospital Care With Intra-Nasal Ketamine for Transport (PRECINKT): A Pilot Study (PRECINKT), ClinicalTrials. gov, Jan. 10, 2014, Ketamine, NCT02033434.
University of British Columbia., Prehospital Analgesia With Intra-Nasal Ketamine (PAIN-K), ClinicalTrials.gov, Apr. 27, 2016, Ketamine, NCT02753114.
University of Arizona., Intranasal Ketamine for Pediatric Procedural Sedation: a Feasibility Study, ClinicalTrials.gov, Mar. 1, 2017, Ketamine, NCT03067974.
University of Alberta., Effects of Low-dose Ketamine as an Adjunct to Propofol-based Anesthesia for Electroconvulsive Therapy, ClinicalTrials.gov, Oct. 19, 2015, Ketamine, NCT02579642.
University of Alabama at Birmingham., miRNAs, Suicide, and Ketamine—Plasma Exosomal microRNAs as Novel Biomarkers for Suicidality and Treatment Outcome, ClinicalTrials.gov, Apr. 16, 2015, Ketamine, NCT02418195.
University of Alabama at Birmingham, Treatment of Suicidal Ideation With Intravenous Ketamine Infusion, ClinicalTrials.gov, Jun. 27, 2013, Ketamine, NCT01887990.
University of Aberdeen, The Use of Ketamine as an Anaesthetic During Electroconvulsive Therapy (KANECT), ClinicalTrials.gov, Mar. 2, 2011, Ketamine, NCT01306760.
University of Aarhus, Sensory Examination and Pharmacological Modulation of Oral Hyperexcitability in Patients With Atypical Odontalgia and Matched Healthy Controls, ClinicalTrials.gov, Jun. 21, 2005, S-ketamine, NCT00115102.
University Hospital, Montpellier., Intranasal Midazolam Versus Intranasal Ketamine to Sedate Newborns for Intubation in Delivery Room, ClinicalTrials.gov, Jan. 25, 2012, Ketamine, NCT01517828.
University Hospital, Lille., Evaluation of the Initial Prescription of Ketamine and Milnacipran for Depression in Palliative Care (KETAPAL), ClinicalTrials.gov, May 26, 2016, Ketamine, NCT02783430.
University Hospital, Grenoble, Estimate the Efficiency of the Association of an Injection of Ketamine and the Venlafaxine in the Severe Major Depressive Disorder for Six Weeks (KETADEP), ClinicalTrials.gov, Mar. 19, 2012, Ketamine, NCT01557712.
University Hospital, Clermont-Ferrand., Ketamine and Neuropathic Pain (KETAPAIN), ClinicalTrials.gov, Jun. 10, 2015, Ketamine, NCT02467517.
University Hospital, Basel, Switzerland., The Analgesic Effect of Combined Treatment With Intranasal S-ketamine and Intranasal Midazolam (NASKEMI), ClinicalTrials.gov, Jan. 12, 2011, S-ketamine, NCT01275547.
University Hospital, Basel, Switzerland., Pharmacokinetics and Pharmacodynamics of Nasally App.lied Esketamine, ClinicalTrials. gov, Feb. 19, 2009, Esketamine, NCT00847418.
University Hospital, Basel, Switzerland., Comparison of Oral Morphine Versus Nasal Ketamine Spray With Chitosan in Cancer Pain Outpatients (ONKEMI), ClinicalTrials.gov, Oct. 29, 2015, ketamine, NCT02591017.
University Health Network, Toronto., Study of Ketamine for Depression in Cancer Patients Receiving Palliative Care, ClinicalTrials. gov, Jan. 25, 2018, Ketamine, NCT03410446.
Universidade Federal De Goias., Intranasal Sedation With Dexmedetomidine and Ketamine in Pediatric Dentistry (NASO II), ClinicalTrials.gov, Sep. 25, 2017, Ketamine, NCT03290625.
Massachusetts General Hospital, Ketamine and Scopolamine Infusions for Treatment-resistant Major Depressive Disorder, ClinicalTrials. gov, Jun. 7, 2012, Ketamine, NCT01613820.
Massachusetts General Hospital, Intranasal Ketamine for Late-Life Depression and Suicidal Ideation, ClinicalTrials.gov, Nov. 20, 2014, Ketamine, NCT02295787.
Massachusetts General Hospital, Double-Blind, Placebo-Controlled Trial of Ketamine Therapy in Treatment-Resistant Depression (TRD), ClinicalTrials.gov, Aug. 12, 2013, Ketamine, NCT01920555.
Massachusetts General Hospital, A Study of Brexpiprazole Plus Ketamine in Treatment-Resistant Depression (TRD), ClinicalTrials. gov, May 11, 2017, Ketamine, NCT03149991.
Martin B. Keller, Issues in Treatment-Resistant Depression, J Clin Psychiatry, 2005, pp. 5-12, vol. 66 Supplementary 8.

(56) References Cited

OTHER PUBLICATIONS

Marlow, et al., Haemodynamic response to induction of anaesthesia with Ketamine/midazolam, Canadian Journal of Anaesthesia, May 28, 1991, pp. 844-848, vol. 38 Issue 7.
Markus Kosel, Study of Depression-Ketamine-Brain Function, ClinicalTrials.gov, Jun. 3, 2010, Ketamine, NCT01135758.
Marks. George., Is There Really Nothing New Under the Sun? Is Low-Dose Ketamine a Fast-Acting Antidepressant Simply Because it is an Opioid?, ajp.psychiatryonline.org, Jul. 10, 2018, pp. 1-2.
Maria Pacella, Single-dose Ketamine for the Reduction of Pain and Depression in the Emergency Department, ClinicalTrials.gov, Feb. 16, 2018, Ketamine, NCT03436121.
Marhofer et al, S( +)-Ketamine for caudal block in paediatric anaesthesia, British Journal of Anaesthesia, 2000, pp. 341-345, vol. 84 Issue 3.
Marangell, et al., Effects of Intrathecal Thyrotropin-Releasing Hormone (protirelin) in Refractory Depressed Patients, Arch Gen Psychiatry, 1997, pp. 214-222, vol. 54.
Manji, et al., Enhancing Neuronal Plasticity and Cellular Resilience to Develop Novel, Improved Therapeutics for Difficult-to-Treat Depression, Biol. Psychiatry, Jan. 23, 2003, pp. 707-742, vol. 53.
Maler, et al, Memantine inhibits ethanol-induced NMDA receptor up-regulation in rat hipp.ocampal neurons, Brain Research, Jul. 11, 2005, pp. 156-162, vol. 1052.
Malcolm, et al, Efficacy and Safety of Intravenous Low-Dose Ketamine for Treatment of Refractory Depression in a Naturalistic Cohort, Abstract of Malcolm., 2016, pp. 1-2, Poster.
Lund University., Racemic Ketamine Versus S-ketamine With Arterial Spin Labeling (ASL)-MRI in Healthy Volunteers, ClinicalTrials. gov, Jan. 10, 2012, S-ketamine, NCT01506921.
Luckenbaugh, et al, Do the dissociative side effects of ketamine mediate its antidepressant effects?, Journal of Affective Disorders, Feb. 18, 2014, pp. 56-61, vol. 159.
Lu, et al, Intravenous ketamine for treatment-refractory depression in medically complex geriatric patients, Am J Geriatr Psychiatry, 2013, pp. S130-S130, Poster No. NR 06.
Louon, et al, Sedation with nasal Ketamine and midazolam for cryotherapy in retinopathy of prematurity, British Journal of Ophthalmology, Mar. 17, 1993, pp. 529-530, vol. 77.
Lopez, et al., Use of repeated intravenous ketamine therapy in treatment-resistant bipolar depression with suicidal behaviour.a case report from Spain, Therapeutic Advances in Psychopharmacology, 2017, pp. 137-140, vol. 7 Issue 4.
Loo, et al., Placebo-controlled pilot trial testing dose titration and intravenous, intramuscular and subcutaneous routes for ketamine in depression, Acta Psychiatr Scand, Feb. 22, 2016, pp. 48-56, vol. 134.
Logan et al., Immobilizing wild mountain lions (felis concolor) with ketamine hydrochloride and xylazine hydrochloridem, Journal of Wildlife Diseases, 22(1):97-103, 1986.
Lodge, et al., Ketamine and phencyclidine: the good, the bad and the unexpected, British Journal of Pharmacology, Jun. 3, 2015, pp. 4254-4276, vol. 172.
Lions Gate Hospital, Intra-nasal Ketamine for Analgesia in the Emergency Department (INKA), ClinicalTrials.gov, Sep. 17, 2012, Ketamine, NCT01686009.
Lindefors, et al., Differential effects of single and repeated ketamine administration on dopamine, serotonin and GABA transmission in rat medial prefrontal cortex, Brain Research, Feb. 11, 1997, pp. 205-212, vol. 759.
Liebrenz, et al., Repeated intravenous ketamine therapy in a patient with treatment-resistant major depression, The World Journal of Biological Psychiatry, Dec. 8, 2009, pp. 640-643, vol. 10 Issue 4.
Liebrenz, et al., Intravenous ketamine therapy in a patient with a treatment-resistant major depression, Swiss Med Wkly, 2007, pp. 234-236, vol. 137.
Li, et al., The Effects of Low-Dose Ketamine on the Prefrontal Cortex and Amygdala in Treatment-Resistant Depression: A Randomized Controlled Study, Human Brain Mapp.ing, Jan. 29, 2016, pp. 1080-1090, vol. 37.
Levine, et al., Assessment of suicide risk by computer-delivered self-rating questionnaire: preliminary findings, Acta Psychiatr Scand, Feb. 25, 1981, pp. 216-220, vol. 80.
Lenze, et al., Ninety-six hour ketamine infusion with co-administered clonidine for treatment-resistant depression: a pilot randomized controlled trial, World J Biol Psychiatry, 2016, pp. 230-238, vol. 17 Issue 3.
Lee, et al., NMDA Receptors Offer More Than One Functionality, Anesth Analg, 2003, pp. 1533-1534, vol. 96.
Layer, et al., Anttidepressant-like Actions of the Polyamine Site NMDA Antagonist, Eliprodil (SL-82.0715), Pharmacology Biochemistry and Behavior, 1995, pp. 621-627, vol. 52 Issue 3.
Lawson Health Research Institute, Intranasal Ketamine for Procedural Sedation (INK), ClinicalTrials.gov, Jul. 11, 2016, Ketamine, NCT02828566.
Larkin, et al., A preliminary naturalistic study of low-dose ketamine for depression and suicide ideation in the emergency department, International Journal of Neuropsychopharmacology, May 5, 2011, pp. 1127-1131, vol. 14.
Lara, et al., Antidepressant, mood stabilizing and procognitive effects of very low dose sublingual ketamine in refractory unipolar and bipolar depression, International Journal of Neuropsychopharmacology, 2013, pp. 2111-2117, vol. 16.
Lapidus, et al., In Vivo Proton Magnetic Resonance Spectroscopy Study of the Relationships Between Lactate, Depression Severity, and Ketamine Treatment in Major Depressive Disorder, Neuropsychopharmacology, 2015, pp. 1-169, Poaste W113.
Lapidus, et al., A Randomized Controlled Trial of Intranasal Ketamine in Major Depressive Disorder, Biol Psychiatry, Dec. 15, 2014, pp. 970-976, vol. 76 Issue 12.
Lally, et al., Neural correlates of change in major depressive disorder anhedonia following open-label ketamine, J Psychopharmacol, 2015, pp. 596-607, vol. 29 Issue 5.
Lai, et al., Pilot dose—response trial of i.v. ketamine in treatment-resistant depression, The World Journal of Biological Psychiatry, Jun. 9, 2014, pp. 579-584, vol. 15.
Kudoh, et al., Small-Dose Ketamine Improves the Postoperative State of Depressed Patients, Anesth Analg, Mar. 12, 2002, pp. 114-118, vol. 95.
Krystal, et al., Subanesthetic Effects of the Noncompetitive NMDA Antagonist, Ketamine, in Humans, Arch Gen Psychiatry, 1994, pp. 199-214, vol. 51.
Krystal, et al., Preliminary evidence of attenuation of the disruptive effects of the NMDA glutamate receptor antagonist, ketamine, on working memory by pretreatment with the group II metabotropic glutamate receptor agonist, LY354740, in healthy human subjects, Psychopharmacology, 2005, pp. 303-309, vol. 179.
Krystal, et al., Interactive effects of subanesthetic ketamine and subhypnotic lorazepam in humans, Psychopharmacology, 1998, pp. 213-229, vol. 135.
Krystal, et al., Interactive effects of subanesthetic ketamine and haloperidol in healthy humans, Psychopharmacology, Feb. 23, 1999, pp. 193-204, vol. 145.
Krystal, et al., Glutamate and GABA systems as targets for novel antidepressant and mood-stabilizing treatments, Molecular Psychiatry, 2002, pp. S71-S80, vol. 7.
Krystal, et al., Comparative and Interactive Human Psychopharmacologic Effects of Ketamine and Amphetamine, Arch Gen Psychiatry, Mar. 18, 2005, pp. 985-995, vol. 62.
Kollmar, et al., Ketamine followed by memantine for the treatment of major depression, Correspondence, 2008, pp. 1-1.
KK Women's and Children's Hospital, Use of S+Ketamine During Target-Controlled Intravenous Anaesthesia After Abdominal Hysterectomy, ClinicalTrials.gov, Jul. 27, 2017, Esketamine, NCT03231683.
KK Women's and Children's Hospital, S Ketamine Use in Total Abdominal Hysterectomy (SKET), ClinicalTrials.gov, Sep. 7, 2015, S Ketamine, NCT02543385.
Ketamine Hydrochloride Injection, Ketamine Hydrochloride—ketamine hydrochloride injection JHP Pharmaceuticals, LLC, Ketamine Hydrochloride Injection, 2013, pp. 1-17.
Kessler, et al., Lifetime Prevalence and Age-of-Onset Distributions of DSM-IV Disorders in the National Comorbidity Survey Replication, Arch Gen Psychiatry, 2005, pp. 593-602, vol. 62.

(56) References Cited

OTHER PUBLICATIONS

Ahlander, Neuropsychopharmacol, 1999, 21, 414-426.
Andine, J. Pharmacol. Exp. Ther., 1999, 290(3), 1393-1408.
Bender, Neuroscience, 2010a, 169, 720-732.
Berge, "Pharmaceutical Salts", J. Pharm. Sci., 1977, 66, 1-19.
Bolon, Toxicol. Pathol., 2013, 41(7), 1028-1048.
Bremner et al., "Measurement of dissociative states with the clinician-administered dissociative states scale (CADSS)", J. Traumatic Stress, 1998, 11(1), 125-136.
Bretz, "Combining multiple comparisons and modeling techniques in dose-response studies", Biometrics, 2005, 61, 738-748.
Canuso, "Efficacy and Safety of intranasal Esketamine for the Rapid Reduction of Symptoms of Depression and Suicidality in Patients at Imminent Risk for Suicide: Results of a Double-Blind, Randomized Placebo-Controlled Study", Am. J. Psych., 2018, 1-11.
Chen, "A sequential enriched design for target patient population in psychiatric clinical trails", Stat. Med., 2014, 33(17), 2953-2967.
Chen, "Evaluation of performance of some enrichment designs dealing with high placebo response in psychiatric clinical trials", Contemp, Clin. Trials, 2011, 32(4), 592-604.
Cohen, Anesthesiol., 1973, 39, 370-376.
Compton et al., International Journal of Life Science and Medical Research, 2013, vol. 3, issue 5, 179-192.
Daly Ella et al: "I ntranasa 1 Esketamine, in Treatment-resistant Depression, a Dose Response Study—Double Blind and Open Label Extension Data", Neuropsychopharmacology, Elsevier Science Publishing, New York, NY, US, vol. 40, No. Suppl. 1, Dec. 1, 2015 (Dec. 1, 2015), S340-S341, XP009509885, pp. ISSN: 0893-133X *abstract*.
Daly Ella J; Singh Jaskaran: "Intranasal, Esketamine in Treatment Resistant Depression—A Double-blind, Randomized, Efficacy and Dose Response Study", Biological Psychiatry, vol. 79, No. 9, Suppl. s, May 1, 2016 (May 1, 2016), pp. 206S-207S, XP009511637, 71st Annual Scientific Convention and Meeting of the Society-of-Biological-Psychiatry (SOBP); Atlanta, GA, USA; May 12-14, 2016 *abstract*.
DeOlmos, Neuroscience, 2009, 164(3), 1347-1359.
Doros, "A repeated measures model for analysis of continuous outcomes in sequential parallel comparison design studies", Stat. Med., 2013, 32(16), 2767-2789.
Ella J Daly: "Efficacy and Safety of Intranasal Esketamine Adjunctive to Oral Antidepressant Therapy in Treatment-Resistant Depression", JAMA, vol. 75, No. 2, Feb. 1, 2018 (Feb. 1, 2018), pp. 139-148.
Fava, "A double-blind, placebo-controlled study of aripiprazole adjunctive to antidepressant therapy among depressed outpatients with inadequate response to prior antidepressant therapy (Adapt-a-Study", Psychother. Psychosom, 2012, 81(2), 87-97.
Fava, "The problem of the placebo response in clinical trials for psychiatric disorders: culprits, possible remedies, and a novel study design approach", Psychother. Psychosom, 2003, 72(3), 115-127.
Gizurarson, Acta Pharm. Nord., 1990, 2(2), 105-122.
Gocmen et al., In Vitro Investigation of the Antibacterial Effect of Ketamine; Upsala J Med Sci 113 (1) 2008: pp. 39-46.
Green, Lab. Anim, 1981, 15, 163-170.
Hoffman, J. Anesthesiology, 1992, 76(5), 755-762.
http://www.pfizer.com/files/products/material_safety_data/PZ00892.pdf; 2008.
https://en.wikipedia.org/wiki/Esketamine; 2015.
Huang, "Comparison of test statistics for the sequential parallel design", Statistics in Biopharmaceutical Research, 2010, 2(1), 42-50.
Hudetz, J. Cardiothor. Vase. Anesth., 2010, 24, 131-142.
International Preliminary Report on Patentability received for PCT Patent Application No. PCT/US13/30476, dated Sep. 25, 2014, 11 pages.
International Preliminary Report on Patentability received for PCT Patent Application No. PCT/US14/27074, dated Sep. 24, 2015, 7 pages.
International Preliminary Report on Patentability received for PCT Patent Application No. PCT/US2016/033404, dated Nov. 30, 2017, 8 pages.
International Search Report and Written Opinion received for PCT Patent Application No. PCT/US2016/033404, dated Aug. 16, 2016, 9 pages.
Ionescu, et al., Rapid and Sustained Reductions in Current Suicidal Ideation Following Repeated Doces of Intravenous Ketamine:, J Clin Psychiatry, 2016, pp. e1-e7, page number.
Ivanova, "Optimality, sample size, and power calculations for the sequential parallel comparison design", Stat. Med., 2011, 30(23), 2793-2803.
James W. Murrough et al: "Dose- and Exposure-Response to Ketamine in Depression", Biological Psychiatry, vol. 70, No. 4, Aug. 1, 2011 (Aug. 1, 2011), pp. e11-e12, XP055610008, New York, NY; US ISSN: 0006-3223, DOI: 10.1016/j.biopsych.2011.02.018.
Jevtovic-Todorovic, Journal of Cerebral Blood Flow and Metabolism, 1997, 17, 168-174.
Joakim Johansson et al: "Prehospital analgesia using nasal administration of S-ketamine—a case se", Scandinavian Journal of Trauma, Resuscitation and Emergency Medicine, Biomed Central Ltd, London UK, vol. 21, No. 1, May 14, 2013 (May 14, 2013), p. 38, XP021151671, ISSN: 1757-7241, DOI: 10.1186/1757-7241-21-38 see materials.
Khan, "Has the rising placebo response impacted antidepressant clinical trail outcome? Data from the US Food and Drug Administration 1987-2013", World Psychiatry, 2017, 16(2), 181-192.
Liu, "Doubly-randomized delayed-start design for enrichment studies with responders or non-responders", J. Biopharm. Stat, 2012, 22(4), 737-757.
Loss, Brain Research, 2012, 1474, 110-117.
Montgomery, "A new depression scale designed to be sensitive to change", Br. J. Psychiatry, 1979, 134, 382-389.
Opposition filed during prosecution of corresponding CL Appl No. 2014-2406.
Papakostas, "L-methylfolate as adjunctive therapy for SSRI-resistant major depression: results of two randomized, double-blind, parallel-sequential trials", Am. J. Psychiatry, 2012, 169(12), 1267-1274.
Paulekuhn, "Trends in Active Pharmaceutical Ingredient Salt Selection based on Analysis of the Orange Book Database", J. Med. Chem., 2007, 50, 6665-6672.
Proescholdt, Brain Res., 2001, 904, 245-251.
Rush et al., "The 16-item quick inventory of depressive symptomatology (QIDS), Clinician Rating (QIDS-C) and Self-Report (QIDS-SR): A psychometric evaluation in patients with chronic major depression", Biol. Psychiatry, 2003, 54(5), 573-583.
Rush, American Journal of Psychiatry, 2006, 163(11), 1905-1917.
Rush, et al., Massachusetts General Hospital Antidepressant Treatment Response Questionnaire; Rush, "The Inventory of Depressive Symptomatology (IDS): Psychometric Properties", Psychol. Med., 1996, 26(3), 477-486.
Rybin, "Placebo non-response measure in sequential parallel comparison design studies", Stat. Med., 2015, 34(15), 2281-2293.
Cavanagh, et al, Psychological autopsy studies of suicide: a systematic review, Psychological Medicine, 2003, pp. 395-405, vol. 33.
Caspi, et al., Influence of Life Stress on Depression: Moderation by a Polymorphism in the 5-HTT Gene, Science, Jul. 18, 2013, pp. 986-689, vol. 301.
Carr, et al., Safety and efficacy of intranasal ketamine for the treatment of breakthrough pain in patients with chronic pain: a randomized, double-blind, placebo-controlled, crossover study, Pain, 2004, pp. 17-27, vol. 108.
Carolinas Healthcare System, IN Sub-Dissociative Ketamine vs IN Fentanyl, ClinicalTrials.gov, Aug. 13, 2015, Ketamine. NCT02521415.
Carlson, et al., Neural Correlates of Rapid Antidepressant Response to Ketamine in Treatment-Resistant Unipolar Depression: A Preliminary Positron Emission Tomography Study, Biol Psychiatry, Feb. 1, 2013, pp. 1213-1221, vol. 73.

(56) References Cited

OTHER PUBLICATIONS

Canuso, et al., Design of Phase 3 Randomized Studies of Intranasal Esketamine to Treat Major Depressive Disorder Symptoms . . . , European Symposium on Suicide & Suicidal Behavior (ESSSB), 2018, pp. 1-1.
Cameroon Baptist Convention Health., Sub-dissociative Intranasal Ketamine for Pediatric Sickle Cell Pain Crises, ClinicalTrials.gov, Oct. 12, 2015, Ketamine, NCT02573714.
Callahan, et al., EvidenceMap of Prevention and Treatment Interventions for Depression in Young People, Hindawi Publishing Corporation Depression Research and Treatment Volume, Dec. 30, 2011, pp. 1-12, Article ID 820735.
Calabrese, et al., A Double-Blind Placebo-Controlled Study of Lamotrigine Monotherapy in Outpatients With Bipolar I Depression, J Clin Psychiatry, 1999, pp. 79-88, vol. 60 Issue 2.
Byrd, et al., Behavioral effects of phencyclidine and ketamine alone and in combination with other drugs, European Journal of Pharmacology, Sep. 29, 1987, pp. 331-341, vol. 144.
Busch, et al., Clinical Correlates of Inpatient Sucide, J Clin Psychiatry, 2003, pp. 14-19, vol. 64.
Brown, et al., The role of randomized trials in testing interventions for the prevention of youth suicide, International Review of Psychiatry, 2007, pp. 1-15, vol. 19 Issue 6.
Brown, et al., Cognitive Therapy for the Prevention of Suicide Attempts, JAMA, Aug. 3, 2005, pp. 563-570, vol. 294 Issue 5.
Brooke Army Medical Center., Ketamine for Acute Suicidal Ideation in the Emergency Department: Randomized Controlled Trial (LOK-SI), ClinicalTrials.gov, Jul. 8, 2013, Ketamine, NCT01892995.
Brooke Army Medical Center, Intranasal Ketamine for Anxiolysis in Pediatric Emergency Department Patients, ClinicalTrials.gov, Feb. 6, 2017, Ketamine, NCT03043430.
Brooke Army Medical Center, "Think Trial: Treatment of Headache With IntraNasal Ketamine: A Randomized Controlled Trial Evaluating the Efficacy of Intranasal Ketamine Versus Standard Therapy in the Management of Primary Headache Syndromes in the Emergency Department" (THINK), ClinicalTrials.gov, Mar. 16, 2017, Ketamine, NCT03081416.
Bromet, et al., Cross-national epidemiology of DSM-IV major depressive episode, BMC Medicine, 2011, pp. 1-16, vol. 9 Issue 90.
Bridge, et al., Placebo Response in Randomized Controlled Trials of Antidepressants for Pediatric Major Depressive Disorder, Am J Psychiatry, 2009, pp. 42-49, vol. 166.
Bridge, et al., Clinical Response and Risk for Reported Suicidal Ideation and Suicide Attempts in Pediatric Antidepressant Treatment A Meta-analysis of Randomized Controlled Trials, (Reprinted) JAMA, Apr. 18, 2007, pp. 1683-1696, vol. 297 Issue 15.
Brent, et al., Treatment-Resistant Depression in Adolescents: Recognition and Management, Child Adolesc Psychiatric Clin N Am, 2006, pp. 1015-1034, vol. 15.
Brent, et al., The Treatment of Adolescent Suicide Attempters Study (TASA): Predictors of Suicidal Events in an Open Treatment Trial, J. Am. Acad. Child Adolesc. Psychiatry, 2009, pp. 987-996, vol. 48 Issue 10.
Brent, et al., Switching to Another SSRI or to Venlafaxine With or Without Cognitive Behavioral Therapy for Adolescents With SSRI-Resistant Depression The TORDIA Randomized Controlled Trial, (Reprinted) JAMA, Feb. 17, 2008, pp. 901-913, vol. 299 Issue 8.
Brent, et al., Association of FKBP5 Polymorphisms With Suicidal Events in the Treatment of Resistant Depression in Adolescents (TORDIA) Study, Am J Psychiatry, 2010, pp. 190-197, vol. 167 Issue 2.
Bremner, et al, Measurement of Dissociative Staeswith the Clinician-Administered Dissociative states scale (CADSS), Journal of Traumatic Stress, 1998, pp. 125-136, vol. 11 Issue 1.
Breakthrough Therapy Design, One Hundred Twelfth Congress of the United States of America at the second session, Breakthrough Therapy Design, 2012, pp. S.3187-2-S.3187-140.
Braun, et al, Ketamine induces apoptosis via the mitochondrial pathway in human lymphocytes and neuronal cells, British Journal of Anaesthesia, Apr. 26, 2010, pp. 347-354, vol. 3.

Braincells Inc., A Study of BCI-838 and Several BCI-632 Prodrugs in Healthy Volunteers, ClinicalTrials.gov, Mar. 7, 2012, BCI-838, NCT01546051.
Braincells Inc., A Multiple Ascending Dose Study of BCI-838 in Healthy Volunteers, ClinicalTrials.gov, Mar. 2, 2012, BCI-838, NCT01548703.
Boyer, et al, Chronic Administration of Imipramine and citalopram Alters the Expression of NMDA Receptor Subunit mRNAs in Mouse Brain, Journal of Molecular Neuroscience, Apr. 9, 1988, pp. 219-233, vol. 10.
Bowdle, et al, Psychedelic Effects of Ketamine in Healthy Volunteers Relationship to Steady-State Plasma Concentrations, Anesthesiology, 1998, pp. 82-88, vol. 88 Issue 1.
Bovill, et al, Alterations in response to somatic pain associated with Anaesthesia, British Journal of Anaesthesia, 1971, pp. 496-499, vol. 43.
Botieron, et al, Refractory Depression in Children and Adolescents, Depression and Anxiety, Jul. 28, 1997, pp. 212-223, vol. 5.
Borges, et al, Twelve-Month Prevalence of and Risk Factors for Suicide Attempts in the World Health Organization World Mental Health Surveys, J Clin Psychiatry, Jul. 10, 2009, pp. 1617-1628, vol. 71 Issue 12.
Borges, et al, Risk factors for twelve-month suicide attempts in the National Comorbidity Survey Replication (NCS-R), Psychol Med, 2006, pp. 1747-1757, vol. 36 Issue 12.
Bongiovi-Garcia, et al., Comparison of clinical and research assessments of diagnosis, suicide attempt history and suicidal ideation in major depression, Journal of Affective Disorders, Sep. 23, 2008, pp. 183-188, vol. 115.
Bonanno, et al., Ketamine in war/tropical surgery (a final tribute to the racemic mixture), Injury International Journal of the Care of the Injured, 2002, pp. 323-327, vol. 33.
Bolze, et al., HPLC determination of ketamine, norketamine, and dehydronorketamine in plasma with a high-purity reversed-phase sorbent, Clinical Chemistry, Nov. 13, 19997, pp. 560-564, vol. 44 Issue 3.
Bolshakov, et al., Determinants of trapp.ing block of N-methyl-D-aspartate receptor channels, Journal of Neurochemistry, Jun. 6, 2003, pp. 56-65, vol. 87.
Bodin, et al., Antiepileptic Drugs Increase Plasma Levels of 4-Hydroxycholesterol in Humans, J. Biol. Chem., Oct. 19, 2001, pp. 38685-38689, vol. 276 Issue 42.
Blier, et al., On the Safety and Benefits of Repeated Intravenous Injections of Ketamine for Depression, Biol Psychiatry , 2012, pp. e11-e12, vol. 72.
Blier Pierre, Aripiprazole in the Treatment of Delusional Parasitosis With Ocular and Dermatologic Presentations, Journal of Clinical Psychopharmacology, 2013, pp. 271-272, vol. 33 Issue 2.
Bjorkhem-Bergman, et al., Comparison of Endogenous 4b-Hydroxycholesterol with Midazolam as Markers for CYP3A4 Induction by Rifampicin, Drug Metabolism and Disposition, May 14, 2013, pp. 1488-1493, vol. 41.
Bjorkhem, et al., Clearance of Fentanyl, Alfentanil, Methohexitone, Thiopentone and Ketamine in Relation to Estimated Hepatic Blood Flow in Several Animal Species: Application to Prediction of Clearance in Man, J. Pharm. Pharmacol., Apr. 20, 2000, pp. 1065-1074, vol. 52.
Birmaher, et al., Summary of the Practice Parameters for the Assessment and Treatment of Children and Adolescents With Depressive Disorders, J. Am. Acad. Child ADolesc. Psychiatry, 1998, pp. 1234-1238, vol. 37 Issue 11.
Birmaher, et al., Randomized, Controlled Trail of Amitriptyline Versus Placebo for Adolescents With "Treatment-Resistant" Major Depression, J. Am. Acad. Child Adolesc. Psychiatry, Nov. 26, 1997, pp. 527-535, vol. 37 Issue 5.
Birmaher, et al., Practice Parameter for the Assessment and Treatment of Children and Adolescents With Depressive Disorders, J. Am. Acad. Child Adolesc. Psychiatry, 2007, pp. 1503-1526, vol. 46 Issue 11.
Birmaher, et al., Course and outcome of child and adolescent major depressive disorder, Child Adolesc Psychiatric Clin N Am, 2002, pp. 619-637, vol. 11.

(56) References Cited

OTHER PUBLICATIONS

Birmaher, et al., Clinical Presentation and Course of Depression in Youth: Does Onset in Childhood Differ From Onset in Adolescence?, Am. Acad. Child Adolesc Psychiatry, Aug. 23, 2003, pp. 63-70, vol. 43 Issue 1.

Birmaher, et al., Childhood and Adolescent Depression: A Review of the Past 10 Years. Part I, J. Am. Acad. Child Adolesc. Psychiatry, Jan. 4, 1996, pp. 1427-1439, vol. 35 Issue 11.

Bickley, et al., Suicide Within Two Weeks of Discharge From Psychiatric Inpatient Care: A Case-Control Study, Psychiatric Services in Advance, Apr. 1, 2013, pp. 1-7.

National Institute of Mental Health (NIMH), Neurobiology of Suicide, ClinicalTrials.gov, Sep. 9, 2015, ketamine, NCT02543983.

National Institute of Mental Health (NIMH), Antidepressant Effects of the Glycine Receptor Antagonist AV-101 (4-chlorokynurenine) in Major Depressive Disorder, ClinicalTrials.gov, Jun. 29, 2015, AV 101 (4-Chlorokynurenine), NCT02484456.

Nasal Powder, Package leaflet: Information for the User, Nasal Powder, 2017, pp. 1-6.

Narita, et al., Role of the NMDA receptor subunit in the expression of the discriminative stimulus effect induced by ketamine, European Journal of Pharmacology, May 29, 2001, pp. 41-46, vol. 423.

Murrough, et al., Rapid and Longer-Term Antidepressant Effects of Repeated. Ketamine Infusions in Treatment-Resistant Major Depression, Biol Psychiatry, Aug. 15, 2015, pp. 250-256, vol. 74 Issue 4.

Murrough, et al., Neurocognitive Effects of Ketamine and Association with Antidepressant Response in Individuals with Treatment-Resistant Depression: A Randomized Controlled Trial, Neuropsychopharmacology, Oct. 18, 2014, pp. 1084-1090, vol. 40.

Murrough, et al., Ketamine for rapid reduction of suicidal ideation: a randomized controlled trial, Psychological Medicine, Jul. 14, 2015, pp. 1-10.

Murray, et al., Global mortality, disability, and the contribution of risk factors:Global Burden of Disease Study, The Lancet, May 17, 1997, pp. 1436-1442, vol. 349.

Mundt, et al., Risk of Prospective Suicidal Behavior Reports among Psychiatric and non-Psychiatric Patients using Lifetime Reports at Baseline, Healthcare Technology Systems, Feb. 19, 2013, pp. 1-1, Poster.

Moryl, et al., Potential Antidepressive Properties of Amantadine, Memantine and Bifemelane, Pharmacology & Toxicology, Feb. 3, 1993, pp. 394-397, vol. 72.

Morrison, Effect of intranasal esketamine on cognitive functioning in healthy participants: a randomized, double-blind, placebo-controlled study, Psychopharmacology, Feb. 1, 2018, pp. 1107-1119, vol. 235.

Moran, et al., The natural history of self-harm from adolescence to young adulthood: a population-based cohort study, Lancet, Nov. 17, 2011, pp. 236-243, vol. 379.

Moore, et al., A comparsion between propofol and thiopentone as induction agents in obstetric anaesthesia, Anaesthesia, Feb. 27, 1989, pp. 753-757, vol. 44.

Molero, et al., Antidepressant Efficacy and Tolerability of Ketamine and Esketamine: A Critical Review, CNS Drugs, May 7, 2018, pp. 411-420, vol. 32.

Moharil, et al., Nasal Dosage Forms and Devices for Intranasal Drug Delivery, World Journal of Pharmacy and Pharmaceutical Sciences, Apr. 5, 2014, pp. 554-571, vol. 3 Issue 4.

Moaddel, et al., D-serine plasma concentration is a potential biomarker of (R,S)-ketamine antidepressant response in subjects with treatment-resistant depression, Psychopharmacology, Jul. 24, 2014, pp. 399-409, vol. 232.

Minneapolis Veterans Affairs Medical Center., Ketamine Infusions for PTSD and Treatment-Resistant Depression, ClinicalTrials.gov, Oct. 16, 2015, Ketamine, NCT02577250.

Millennium Pharmaceuticals, Inc., Efficacy and Safety of TAK-653 in Treatment-Resistant Depression, ClinicalTrials.gov, Oct. 18, 2017, TAK-653, NCT03312894.

Meyer, et al., Suicidality and Risk of Suicide-Definition, Drug Safety Concerns, and a Necessary Target for Drug Development: A brief Report, J Clin Psychiatry, Jul. 13, 2010, pp. e1-e7.

Messer, et al., The Use of a Series of Ketamine Infusions in Two Patients With Treatment-Resistant Depression, J Neuropsychiatry Clin Neurosci, 2010, pp. 442-444, vol. 22 Issue 4.

Mental Health Serv Admin., Results From the 2013 National Survey on Drug Use and Health: Mental Health Detailed Tables, Mental Health Serv Admin, Nov. 14, 2014, pp. 1-577.

Mellon, et al., Use of Anesthetic Agents in Neonates and Young Children, Anesth Analg, 2007, pp. 509-520, vol. 104.

Mellon, et al., Blockade of NMDA Receptors and Apoptotic Neurodegeneratin in the Developing Brain, Science, Mar. 10, 2011, pp. 70-74, vol. 283.

Medical University of Vienna., Positron Emission Tomography Assessment of Ketamine Binding of the Serotonin Transporter, ClinicalTrials.gov, Mar. 23, 2016, Ketamine, NCT02717052.

Medical University of Vienna., Network Dysfunction, Schizophrenia and Pharmacological Magnetic Resonance Imaging (phMRI), ClinicalTrials.gov, Jul. 14, 2011, Esketamine, NCT01394757.

Medical University of Vienna., Investigation of Antidepressant Efficacy of Oral Ketamine Treatment, ClinicalTrials.gov, Dec. 14, 2016, Ketamine, NCT02992496.

Medical University of Graz., The Preemptive Analgetic Potency of Low Dose S-Ketamine (Miniket), ClinicalTrials.gov, Dec. 1, 2009, S-Ketamine, NCT01022840.

McLean Hospital., A Trial of Intranasal Ketamine for the Treatment of Obsessive-Compulsive Disorder, ClinicalTrials.gov, Sep. 9, 2014, Ketamine, NCT02234011.

McGirr, et al., A systematic review and meta-analysis of randomized, double-blind, placebo-controlled trails of ketamine in the rapid treatment of major depressive episodes, Psychological Medicine, 2015, pp. 693-704, vol. 42.

McGhee, et al., The Correlation Between Ketamine and Post-traumatic Stress Disorder in Burned Service Members, The Journal of Trauma, Oct. 31, 2007, pp. S195-S199, vol. 64 Issue 2.

McClean, et al., Ketamine concentrations during cardio-pulmonary bypass, Canadian Journal of Anaesthesia, Jan. 31, 1996, pp. 580-584, vol. 43 Issue 6.

Mayo Clinic., Oral Ketamine in the Treatment of Depression and Anxiety in Patients With Cancer, ClinicalTrials.gov, Sep. 7, 2012, Ketamine, NCT01680172.

Mayo Clinic., Ketamine for Depression and Suicide Risk (Ketamine), ClinicalTrials.gov, Mar. 24, 2014, Ketamine, NCT02094898.

Mayo Clinic., Ketamine Anesthesia in Electroconvulsive Therapy, ClinicalTrials.gov, Jun. 6, 2011, Ketamine, NCT01367119.

Mayo Clinic., Glutamate MRS During Ketamine Infusion, ClinicalTrials.gov, Jun. 29, 2018, Ketamine, NCT03573349.

Mayo Clinic, The Bio-K Study: A Single-Arm, Open-Label, Biomarker Development Clinical Trial of Ketamine for Non-Psychotic Unipolar Major Depression and Bipolar I or II Depression. (Bio-K), ClinicalTrials.gov, May 17, 2017, Ketamine, NCT03156504.

May, et al., Predicting future suicide attempts among depressed suicide ideators: A 10-year longitudinal study, Journal of Psychiatric Research, Apr. 5, 2012, pp. 1-7.

Maurizio Fava., Diagnosis and Definition of Treatment-Resistant Depression, Biol Psychiatry, Feb. 21, 2003, pp. 649-659, vol. 53.

Mati Simon, What If Ketamine Actually Works Like an Opioid?, Wired, Aug. 29, 2018, pp. 1-10, NA.

Mathew_et_al, Ketamine for Treatment-Resistant Unipolar Depression, CNS Drugs, 2012, pp. 189-204, vol. 26 Issue 3, Adis Data Information BV.

Mathew, et al., Riluzole for relapse prevention following intravenous ketamine in treatment-resistant depression: a pilot randomized, placebocontrolled continuation trial, Int J Neuropsychopharmacol, 2010, pp. 1-19, vol. 13 Issue 1.

Mathew, et al., Glutamate modulators as novel interventions for mood disorders Moduladores de glutamato como novas interven9oes em transtofnos do humor, Rev Bras Psiquiatr, Jul. 15, 2005, pp. 243-248, vol. 27 Issue 3.

Massachusetis General Hospital., Physiological and Cognitive Biomarkers for Ketamine's Antidepressant Effects, ClinicalTrials.gov, Jan. 29, 2016, Ketamine's, NCT02669043.

(56) References Cited

OTHER PUBLICATIONS

Massachusetis General Hospital., Neurocognitive Features of Patients With Treatment-Resistant Depression, ClinicalTrials.gov, Apr. 28, 2017, Depression, NCT03134066.
Massachusetis General Hospital., Ketamine Versus Placebo for Treatment Resistant Major Depressive Disorder, ClinicalTrials.gov, Aug. 17, 2012, Ketamine, NCT01667926.
Massachusetis General Hospital., Ketamine for Depression: An MRI Study, ClinicalTrials.gov, Sep. 9, 2015, Ketamine, NCT02544607.
Massachusetis General Hospital, The Impact of Ketamine on the Reward Circuitry of Suicidal Patients, ClinicalTrials.gov, Aug. 25, 2015, Ketamine, NCT02532153.
Massachusetis General Hospital, N-methyl-D-aspartate Antagonist (Ketamine) Augmentation of Electroconvulsive Treatment for Severe Major Depression, ClinicalTrials.gov, Dec. 15, 2010, Ketamine, NCT01260649.
Massachusetis General Hospital, Ketamine Infusion for Treatment-resistant Major Depressive Disorder, ClinicalTrials.gov, Apr. 23, 2012, Ketamine, NCT01582945.
Auer, R.N, Coulter, K.C., 1994. The nature and time course of neuronal vacuolation induced by the N-methyl-D-aspartate antagonist MK-801. Acta Neuropathol. 87, 1-7.
Auer, R.N., 1996. Effect of age and sex on N-methyl-D-aspartate antagonist-induced neuronal necrosis in rats. Stroke 27, 743-746.
Aulton M E: Pharmaceutics, The Science of Dosage Form Design, 254-258; 262-268; 1988, 485-490, 34 pages.
Aulton, Michael: Aulton's Pharmaceutics; Dosage Form Design and Manufacture, 3rd Edition; 2008, (368-369) 4 pages.
Begec et al: Rev Bras Anestesiol, The antimicrobial effects of ketamine combined with propofol: An in vitro study, 2013, 63(6): 461-465.
Bender, Neurotoxicology and Teratology, 2010b, 32, 542-550.
Bentley, William E.: Ketamine: an update for its use in complex regional pain syndrome and major depressive disorder; Clinical & Experimental Pharmacology (2015), 5(2), 1000169/1-1000169/3.
Bently et al. Med. Clin N Am. 98, 981-1005 (2014).
Bitter, Christoph: Transmucosal Nasal Drug Delivery: Pharmacokinetics and Pharmacodynamics of Nasally Applied Esketamine, Inauguraldissertation, zurErlangung der Würde eines Doktors der Philosophie vorgelegt der Philosophisch-Naturwissenschaftlichen Fakultät der Universitat Basel Basel 2011, 1-208.
Bloch, Michael H: Effects of Ketamine in Treatment-Refractory Obsessive-Compulsive Disorder; Biological Psychiatry (2012), 72(11), 964-970.
Bueno, Experimental and Toxicologic Pathology, 2003, 54, 319-334.
Chang, "Biotransformation and Disposition of Ketamine", Int. Anesthesiol. Clin. Summer 1974;12(2):157-177.
Chi, "On clinical trials with a high placebo rate. Contemporary Clinical Trials Communications", 2016, 2, 34-53.
Clinical Trials.gov Identifier: NCT02133001, May 7, 2014, URL:https://clinicaltrials.gov/ct2/show/NCT02133001.
ClinicalTrials.gov NCT02497287 (Sep. 30, 2015).
Colbourne, F., Rakic, D., Auer, R.N., 1999. The effects of temperature and scopolamine on N-methyl-D-aspartate antagonist-induced neuronal necrosis in the rat. Neurosc. 90(1), 87-94.
Corya et al., Journal of Clinical Psychiatry, 2003, 64(11), 1349-1356.
De Olmos, S., Bueno, A., Bender, C., Lorenzo, A., de Olmos, J., 2008. Sex differences and influence of gonadal homones on MK801-induced neuronal degeneration in the granular retrosplenial cortex of the rat. Brain Struct. Funct. 213, 229-238.
European Medicines Agency Inspections (EMEA); Guideline on Excipients in the Dossier for Application for Marketing Authorisation of a Medicinal Product; London, Jun. 19, 2007, Doc. Ref. EMEA/CHMP/QWP/396951/2006; 12 pages.
European Pharmacopoeia—7th Edition; Published Jul. 15, 2010; 11 pages.
Farber, N.B., Wozniak, D.F., Price, M.T., Labruyere, J., Huss, J., St Peter, H., Olney, J.W., 1995. Age-specific neurotoxicity in the rat associated with NMDA receptor blockade: potential relevance to schizophrenia? Biol. Psychiatry 38, 788-796.
FDA Anesthetic and Life Support Drugs Advisory Committee (ALSDAC), Center for Drug Evaluation and Research, Silver Springs, MD, Mar. 10, 2011. "Ketamine and the Neonatal Brain: Rat Pups vs. Babies." On FDA website in archives Guest Presentation Mar. 10, 2011 pp. 1-76.
Feder, et al: Efficacy of intravenous ketamine for treatment of chronic posttraumatic stress disorder a randomized clinical trial; JAMA Psychiatry (2014), 71(6), 681-688.
Fix, A.S., Horn, J.W., Wightman, K.A., Johnson, C.A., Long, G.G., Storts, R.W., Farber, N., Wozniak, D.F., Olney, J.W., 1993. Neuronal vacuolation and necrosis induced by the noncompetitive N-methyl-D-aspartate (NMDA) antagonist MK(+)801 (dizocilpine maleate): a light and electron microscopic evaluation of the rat retrosplenial cortex. Exp. Neurol. 123, 204-215.
Fix, A.S., Long, G.G., Wozniak, D.F., Olney, J.W., 1994. Pathomorphologic effects of N-methyl-D-aspartate antagonists in the rat posterior cingulate/retrosplenial cerebral cortex: a review. Drug Development Res. 32, 147-152.
Fix, A.S., Ross, J.F., Stitzel, S.R., Switzer, R.C., 1996. Integrated evaluation of central nervous system lesions: stains for neurons, astrocytes, and microglia reveal the spatial and temporal features of MK-801-induced neuronal necrosis in the rat cerebral cortex. Toxicol. Pathol. 24(3), 291-304.
Fix, A.S., Stitzel, S.R., Ridder, G.M., Switzer, R.C., 2000. MK-801 neurotoxicity in cupric silver-stained sections: lesion reconstruction by 3-dimensional computer image analysis. Toxicol. Pathol. 28(1), 84 90.
Fix, A.S., Wozniak, D.F., Truex, J.L., McEwen, M., Miller, J.P., Olney, J.W., 1995. Quantitative analysis of factors influencing neuronal necrosis induced by MK-801 in the rat posterior cingulate/retrospenial cortex. Brain Res. 696, 194-204.
Gennaro, Alfonso: Remington: The Science and Practice of Pharmacy, 20th ed., 2000, pp. 1042-1047.
Gingerich HCP Live, https://www.mdmag.com/medical-news, Sep. 4, 2018.
Gonzalo Laje, Brain-Derived Neurotrophic Factor VAL66MET Polymorphism and Antidepressant Efficacy of Ketamine in Depressed Patients; Biol Psychiatry, Dec. 1, 2012,vol. 72, NR:11, pp. 1-4 (E27-E28), URL, https://www.ncbi.nlm.nih.gov/pmc/articles/PMC3786174/.
Gregory K. Brown, Ph.D., "A review of suicide assessment measures for intervention research with adults and older adults", National Institute of Mental Health, 2000, pp. 1-57.
Guy, "ECDEU Assessment Manual for Psychopharmacology—Revised (DHEW Publ No. Adm 76-338)" Rockville, MD: U.S. Department of Health, Education and Welfare, Public Health Service, Alcohol, Drug Abuse and Mental Health Administration, NIMH Psychopharmacology Research Branch, Division of Extramural Research Programs; 1976, pp. 218-222.
Hoffman, Pharmacology, Biochemistry and Behavior, 2003, 74, 933-941.
Horvath, Brain Res., 1997, 753(2), 181-195.
Howland R.H., Journal of Psychosocial Nursing and Mental Health Services, 2008, 46(10), 21-24.
Hur, Environmental Toxicology and Pharmacology, 1999, 7, 143-146.
Ito, Wataru: Observation of Distressed Conspecific as a Model of Emotional Trauma Generates Silent Synapses in the Prefrontal-Amygdala Pathway and Enhances Fear Learning, but Ketamine Abolishes those Effects; Neuropsychopharmacology (2015), 40(11), 2536-2545 Apr. 13, 2015.
Jevtovic-Todorovic, V., Benshoff, N., Olney, J.W., 2000. Ketamine potentiates cerebrocortical damage induced by the common anesthetic agent nitrous oxide in adults rats. Br. J. Pharmacol. 130, 1692-1698.
Jevtovic-Todorovic, V., Carter, L.B., 2005. The anesthetics nitrous oxide and ketamine are more neurotoxic to old than to young rat brain. Neurobiology of Aging. 26, 947-956.
Jevtovic-Todorovic, V., Kirby, C.O., Olney, J., 1997. Isoflurane and Propofol Block Neurotoxicity Caused by MK-801 in the Rat

(56) References Cited

OTHER PUBLICATIONS

Posterior Cingulate/Retrosplenial Cortex. Journal of Cerebral Blood Flow and Metabolism 17,168-174.
Jevtovic-Todorovic, V., Wozniak, D.F., Benshoff, N.D., Olney, J.W., 2001. A comparative evaluation of the neurotoxic properties of ketamine and nitrous oxide. Brain Res. 895, 264-267.
Journal of Clinical and Experimental Medicine (Igaku No Ayumi), 2006, vol. 219, No. 13, p. 949-953.
Juven-Wetzler, Alzbeta: Immediate ketamine treatment does not prevent posttraumatic stress responses in an animal model for PTSD; European Neuropsychopharmacology (2014), 24(3), 469-479.
Ketalar 10mg/ml Injection; Summary of Product Characteristics (SmPC), Mar. 17, 2020, 8 pages.
Ketanest S, Pfizer, Fachinformation, Jan. 2019, 5 pages.
Khalili-Mahani, N: Effect of subanaesthetic ketamine on plasma and saliva cortisol secretion; British Journal of Anaesthesia (2015), 115(1), 68-75 Published: May 16, 2015.
Kron, Miriam: Brain activity mapping in Mecp2 mutant mice reveals functional deficits in forebrain circuits, including key nodes in the default mode network, that are reversed with ketamine treatment; Journal of Neuroscience (2012), 32(40), 13860-13872.
Liman, Suryamin: Preventive treatment with ketamine attenuates the ischaemia-reperfusion response in a chronic postischaemia pain model; Oxidative Medicine and Cellular Longevity (2015) 380403/1-380403/9 Jun. 16, 2015 Published online Jun. 16, 2015.
Liu, Xing-qing; Hu, Xu-dong; Zhang, Wen-li; Ling, Chen; Lin, Jin-bing; Du, Shun-yan, Influence of preinjection of small dose ketamine on Edinburgh postnatal depression scale of cesarean section women, Guangdong Yixue (2013), 34(12), 1917-1919 (Abstract).
Lu, Li-ling, Effect of maternal pre-injection of low dose amphetamine on postpartum depression score in cesarean section, Yixue Zongshu (2015), 21 (24), 4570-4572 (Abstract).
Ma, Jingyi: Deep brain stimulation of the medial septum or nucleus accumbens alleviates psychosis-relevant behavior in ketamine-treated rats; Behavioural Brain Research (2014), 266, 174-182.
Maruff P, Werth J, Giordani B, Caveney, AF, Feltner D, Snyder PJ. A statistical approach for classifying change in cognitive function in individuals following pharmacologic challenge: an example with alprazolam Psychopharmacology 2006; 186: 7-17.
Murrough, et al., Antidepressant Efficacy of Ketamine in Treatment-Resistant Major Depression: A Two-Site Randomized Controlled Trial, Am J Psychiatry, Oct. 1, 2013, pp. 1134-1142, vol. 170 Issue 10.
Nakako, Tomokazu: Effects of lurasidone on ketamine-induced joint visual attention dysfunction as a possible disease model of autism spectrum disorders in common marmosets; Behavioural Brain Research (2014), 274, 349-354.
Niciu, Mark J: Two cases of delayed-onset suicidal ideation, dysphoria and anxiety after ketamine infusion in patients with obsessive-compulsive disorder and a history of major depressive disorder; Journal of Psychopharmacology (London, United Kingdom) (2013), 27 (7), 651-654.
Okayama Igakkai Zasshi (Journal of Okayama Medical Association), 2008, vol. 119, p. 315-317.
Olney, J.W., Labruyere, J., Price, M.T., 1989. Pathological changes induced in cerebrocortical neurons by phencyclidine and related drugs. Science 240, 1360-1362.
Olney, J.W., Labruyere. J., Wang, G., Wozniak, D.F., Price, M.T., Sesma, M.A., 1991. NMDA antagonist neurotoxicity: mechanism and prevention. Science 254, 1515-1518.
PRD3253CLPCT_Opposition BriefTranslation, 2014.
Remington: The Science and Practice of Pharmacy; 20th Edition; Chapter 78, p. 1398, 2000, (3pp).
Rodriquez, et al: Randomized Controlled Crossover Trial of Ketamine in Obsessive-Compulsive Disorder: Proof-of-Concept Rodriguez; Neuropsychopharmacology (2013), 38(12), 2475-2483.
Rowe et al: Handbook of Pharmaceutical Excipients, Sixth Edition, 2009, pp. 181-183; 247-250.
Rush, CNS Drugs, 2009, 23(8), 627-647.
Sanli, et al: The effect of addition of ketamine to lidocaine on postoperative pain in rhinoplasties; Turkish Journal of Medical Sciences (2016), 46(3), Aug. 9, 2015, pp. 789-794.
Schoenenberg, Michael: Effects of peritraumatic ketamine medication on early and sustained posttraumatic stress symptoms in moderately injured accident victims; Germany Psychopharmacology (Berlin, Germany) (2005), 182 (3), 420-425.
Slomski, Anita; Ketamine effective in treating PTSD; The Journal of the American Medical Association (2014), 312 (4), 327.
Study NCT01998958; A Double-Blind, Doubly-Randomized, Placebo-Controlled Study of Intranasal Esketamine in an Adaptive Treatment Protocol to Assess Safety and Efficacy in Treatment-Resistant Depression (SYNAPSE); Submitted Date: Feb. 14, 2014 (v2).
Study NCT01998958; A Double-Blind, Doubly-Randomized, Placebo-Controlled Study of Intranasal Esketamine in an Adaptive Treatment Protocol to Assess Safety and Efficacy in Treatment-Resistant Depression (SYNAPSE); Submitted Date: Mar. 18, 2014 (v3).
Study NCT01998958; A Double-Blind, Doubly-Randomized, Placebo-Controlled Study of Intranasal Esketamine in an Adaptive Treatment Protocol to Assess Safety and Efficacy in Treatment-Resistant Depression (SYNAPSE); Submitted Date: Nov. 25, 2013 (v1).
Study NCT02133001; A Double-blind, Randomized, Placebo Controlled Study to Evaluate the Efficacy and Safety of Intranasal Esketamine for the Rapid Reduction of the Symptoms of Major Depressive Disorder, Including Suicidal Ideation, in Subjects Who Are Assessed to be at Imminent Risk for Suicide; Submitted Date: May 6, 2014 (v1).
Vann et al. Everyday Health Dec. 2, 2011 (8 pgs).
Wilcock, et al: Therapeutic Reviews, Journal of Pain and Symptom Management, vol. 41, No. 3, Mar. 3, 2011, 640-649.
Willis, C.L., Ray, D.E., 2007. Antioxidants attenuate MK-801-induced cortical neurotoxicity in the rat. NeuroToxicology 28, 161-167.
Wilson, Pharmacology, Biochemistry and Behavior 81, 2005, 530-534.
Wozniak, Neurobiology of Disease, 1998, 5(5), 305-322.
Wozniak, Psychopharmacology, 1990, 101(1), 47-56.
Wu, et al., Transgenerational impairment of hippocampal Akt-mTOR signaling and behavioral deficits in the offspring of mice that experience postpartum depression-like illness. Progress in Neuro-Psychopharmacology & biological Psychiatry (2017), 73, 11-18.
Xia, et al., Chronic stress prior to pregnancy potentiated regulated by Akt-mTOR signaling in the hippocampus. Scientific Reports (2016), 6, 35042.
Xu, et al., Single bolus low-dose of ketamine does not prevent postpartum depression: a randomized, double-blind, placebo-controlled, prospective clinical trial. Archives of Gynecology and Obstetrics (2017), 295, 1167-1174.
Yang et al., "Serum lnterleukin-6 is a predictive biomarker for ketamine's antidepressant effect in treatment-resistant patients with major depression", Biological Psychiatry 77, 2015, pp. e19-e20.
Yazdi, Bijan; Comparison of additive oral Clonidine with Ketamine, on post-operative pain and hemodynamic in cataract extraction under topical anesthesia and sedation; Pharmaceutical and Biomedical Sciences (2015), 4(5), 37-42.
Zajackowski, Neurotox. Res., 2000, 1(4), 299-310.
Zhang, Li-Ming: Anxiolytic effects of ketamine in animal models of posttraumatic stress disorder; Psychopharmacology (Heidelberg, Germany) (2015), 232 (4), 663-672 Sep. 18, 2014.
Zhang, X., Boulton, A.A., Zuo, D.M., Yu, P.H., 1996. MK-801 induces apoptotic neuronal death in the rat retrosplenial cortex: prevention by cycloheximide and R(-)-2-hexyl-methylpropargylamine. J. Neurosc. Res. 46, 82-89.
Glue, et al: Dose- and Exposure-Response to Ketamine in Depression, Biol Psychiatry 2011; 70: e9-e10.
Lim, Y.Y. et al., (Australian Imaging, Biomarkers and Lifestyle (AIBL) Research Group), "BDNF Val66Met, AB Amyloid and cognitive decline in preclinical Alzheimer's disease", Neurobiol. Aging, Nov. 2013, vol. 34(11), pp. 2457-2464.
Liu, R.Y., Biol. Psychiatry, BDNF Val66Met allele impairs basal and ketamine-stimulated synaptogenesis in prefrontal cortex, 2012, vol. 71 (11), pp. 996-1005.

(56) References Cited

OTHER PUBLICATIONS

Pecina M. et al., "Valence-specific effects of BDNF Val66Met polymorphism on dopaminergic stress and reward processing in humans", J. Neurosci., Apr. 23, 2014, vol. 34(17), pp. 5874-5881.

U.S. Appl. No. 16/727,594, Entitled "VAL66MET (SNP rs6265) Methods for the Treatment of Depression"; filed Dec. 26, 2019.

Carr et al. "Intranasal Ketamine The Essence of Analgesia and Analgesics". Publisher: Cambridge University Press. 2010. pp. 440-443.

Dhakar RC. et al., "A review on factors affecting the design of nasal drug delivery system," International Journal of Drug Delivery, vol. 3, 2011, pp. 194-208.

Duffy, S., "Esleta,ome Masa; Spray NDA Submitted to FDA for Treatment-Resistant Depression," Psychiatry Advisor, Retrieved at https://www.psychiatryadvisor.com/home/topics/mood-disorders/depressive-disorder/esketamine-nasal-spray-nda-submitted-to-fda-for-treatment-resistant-depression, Sep. 5, 2018.

FDA., "Drugs@FDA Glossary of Terms." fda.gov, Retrieved at https://www.fda.gov/drugs/drug-approvals-and-databases/drugsfda-glossary-terms#:~: text=A%20Reference%20Listed%20Drug%20(RLD,New%20Drug%20Application%20(ANDA), Nov. 14, 2017, p. 8.

FDA., "What's in a REMS?."fda.gov, retrieved at https://www.fda/gov/drugs/risk-evaluation-and-mitigation-strategies-rems/whats-rems, Jan. 26, 2018, p. 4.

\* cited by examiner

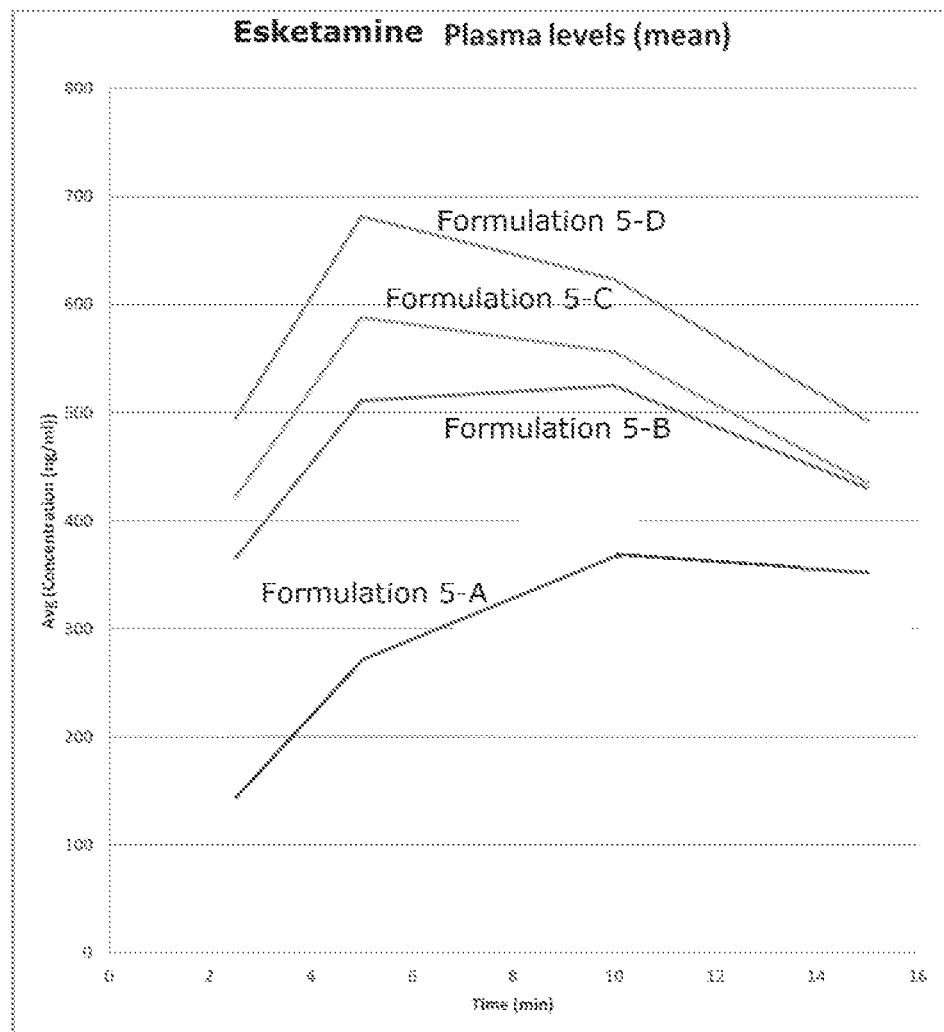
Figure 1: Esketamine Plasma Levels, rat pK Study Dosing Formulations 5-A through 5-D @ 10 µL/rat

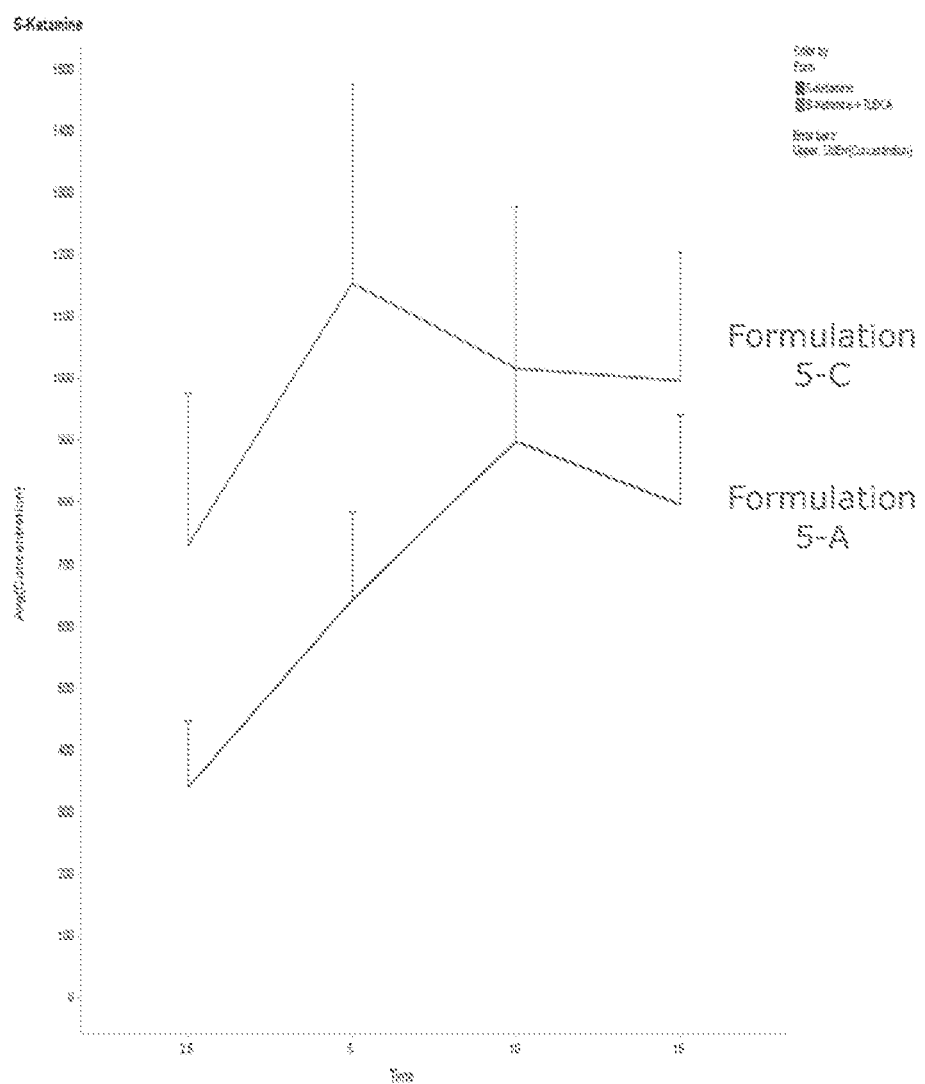
Figure 2: Esketamine Plasma Levels, rat pK Study Dosing Formulations 5-A and 5-C @ 25 µL/rat

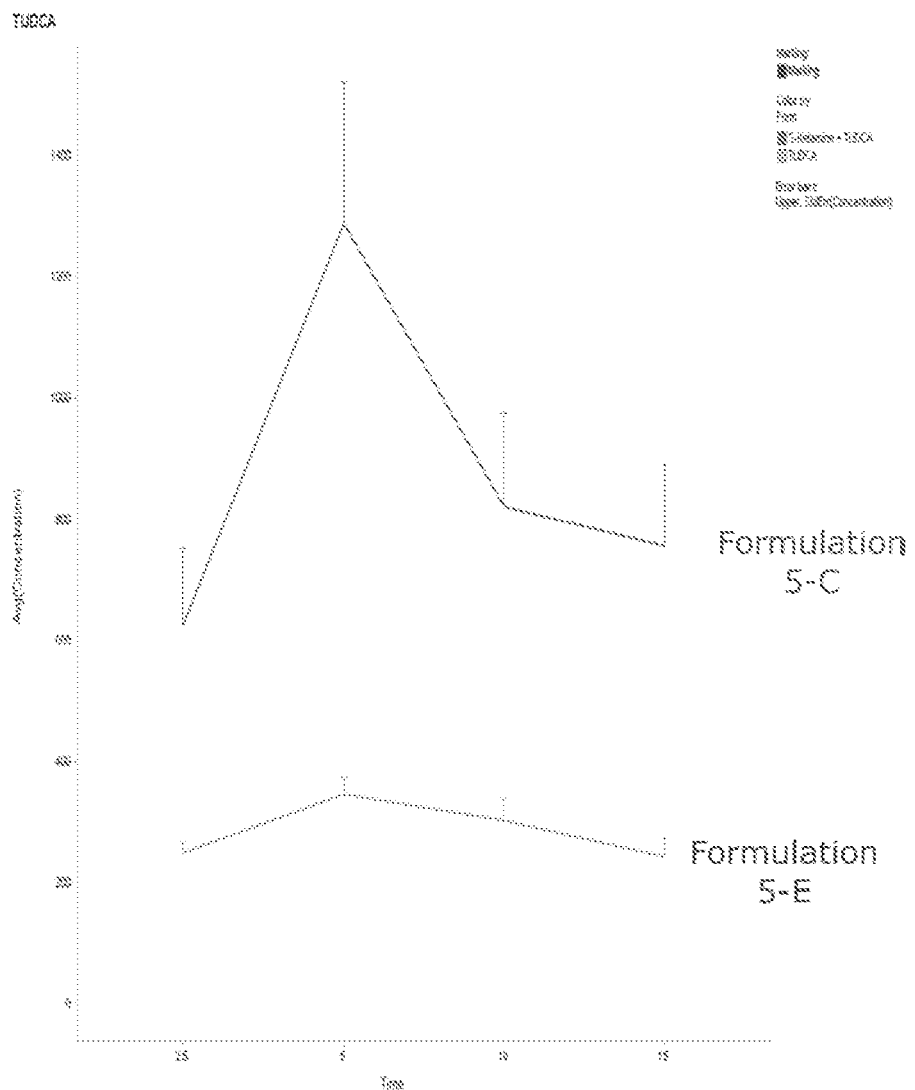
Figure 3: Esketamine Plasma Levels, rat pK Study Dosing Formulation 5C and Reference Formula 5-E @ 25 µL/rat

PHARMACEUTICAL COMPOSITION OF S-KETAMINE HYDROCHLORIDE

CROSS REFERENCE TO RELATED APPLICATIONS

This application is a continuation of U.S. patent application Ser. No. 14/211,874, filed on Mar. 14, 2014 which claims the benefit of U.S. Provisional Application 61/791,237, filed on Mar. 15, 2013, which is incorporated by reference herein in its entirety.

FIELD OF THE INVENTION

The present invention is directed to an aqueous formulation of S-ketamine hydrochloride, preferably for nasal administration, wherein the formulation does not contain an antimicrobial preservative.

BACKGROUND OF THE INVENTION

Ketamine (a racemic mixture of the corresponding S- and R-enantiomers) is an NMDA receptor antagonist, with a wide range of effects in humans, including analgesia, anesthesia, hallucinations, dissociative effects, elevated blood pressure and bronchodilation. Ketamine is primarily used for the induction and maintenance of general anesthesia. Other uses include sedation in intensive care, analgesia (particularly in emergency medicine and treatment of bronchospasms. Ketamine has also been shown to be efficacious in the treatment of depression (particularly in those who have not responded to current anti-depressant treatment). In patients with major depressive disorders, ketamine has additionally been shown to produce a rapid antidepressant effect, acting within hours.

The S-ketamine enantiomer (or S-(+)-ketamine or esketamine) has higher potency or affinity for the NMDA receptor and thus potentially allowing for lower effective dosages; and is available for medical use, administered either IV (intravenously) or IM (intramuscularly), under the brand name KETANEST S.

In the formulation of a pharmaceutical compositing, the stability of the active ingredient is a primary concern. In general, drug substances are less stable in aqueous media than solid dosage forms, and it is important to properly stabilize and preserve liquid aqueous formulations such as solutions, suspensions, and emulsions. Acid-base reactions, acid or base catalysis, oxidation, and reduction can occur in these products. These reactions can arise from drug substance-excipient interactions, excipient-excipient interactions or container-product interactions. Particularly for pH sensitive compounds, these interactions may alter the pH and may decrease solubility and potentially cause precipitation.

Oxidative labile drug substances or vitamins, essential oils, and almost all fats and oils can be oxidized by autoxidation. Such reactions can be initiated by heat, light, peroxides, or other labile compounds or heavy metals such as copper or iron.

The effect of trace metals can be minimized by using chelating agents such as EDTA. Antioxidants may retard or delay oxidation by rapidly reacting with free radicals as they are formed (quenching). Common antioxidants include propyl, octyl and dodecylesters of gallic acid, butylated hydroxyanisole (BHA), butylated hydroxytoluene (BHT), ascorbic acid, sodium ascorbate, monothioglycerol, potassium or sodium metabisulfite, propionic acid, propyl gallate, sodium bisulfite, sodium sulfite, and the tocopherols or vitamin E.

In addition to stabilization of pharmaceutical preparations against chemical and physical degradation, liquid and semi-solid preparations, particularly multiple dosed preparations, must usually be protected against microbial contamination. In contrast to solid preparations, aqueous solutions, syrups, emulsions, and suspensions often provide excellent growth media for microorganisms such as molds, yeast, and bacteria (e.g. *Pseudomonas Aeruginosa, E. Coli, Salmonella* spp., *Staphylococcus aureus, Candida albicans, Aspergillus niger*). Contamination by these microorganisms may occur during manufacturing or when a dose is taken from a multiple dosed formulation. Growth of the microorganisms occurs when a sufficient amount of water is present in the formulation.

Ophthalmic and injectable preparations are typically sterilized by autoclaving or filtration. However, many of them require the presence of an antimicrobial preservative to maintain aseptic conditions throughout their stated shelf life, specifically for multiple dosed preparations.

When a preservative is required, its selection is based upon several considerations, in particular the site of use whether internal, external or ophthalmic (for further details it can be referred to e.g. Remington, The Science and Practice of Pharmacy, 21st edition, Lippincott Williams & Wilkins, 2005).

Many liquid formulations for oral administration, particularly multiple dosed formulations, contain parabens as preservatives, e.g. methyl paraben (methyl-4-hydroxybenzoate) and propyl paraben (propyl-4-hydroxybenzoate). For example, in the Federal Republic of Germany liquid oral formulations containing parabens are commercialized under the trademarks: ben-u-ron®; Cetirizin-ratiopharm®; Pipamperon HEXAL®; Sedotussin®; TALOXA®; Truxal®; XUSAL®; talvosilen®; and Timonil®. Other commercialized liquid formulations contain sorbic acid or its potassium salt as preservative, e.g. ibuprofen liquid formulations and morphine liquid formulations.

Because of the number of excipients and additives in these preparations, it is recommended all the ingredients be listed on the container to reduce the risks that confront hypersensitive patients when these products are administered.

The preservatives benzalkonium chloride and potassium sorbate are also widely used e.g. in nasal drops and sprays. Recently, side effects resulting from mucosal damage caused by benzalkonium chloride and potassium sorbate were reported (cf. C. Y. Ho et al., Am J Rhinol. 2008, 22(2), 125-9). As far as hypersensitivity reactions of preservatives in topical ophthalmic therapies are concerned, quaternary ammoniums (benzalkonium chloride) are commonly associated with irritant toxic reactions whereas the organomercurials (thimerosal) and the alcohols (chlorobutanol) have high associations, respectively, with allergic responses (cf. J. Hong et al., Curr Opin Allergy Clin Immunol. 2009, 9(5), 447-53). Parabens have been implicated in numerous cases of contact sensitivity associated with cutaneous exposure (cf. M. G. Soni et al., Food Chem Toxicol. 2001, 39(6), 513-32) and have been reported to exert a weak estrogenic activity (cf. S. Oishi, Food Chem Toxicol. 2002, 40(12), 1807-13 and M. G. Soni et al., Food Chem Toxicol. 2005, 43(7), 985-015).

Due to these undesired side effects of known preservatives, it is desirable to provide aqueous pharmaceutical compositions (for example, for nasal administration) that exhibit a sufficient shelf life and in use stability in the absence of preservatives or at least in the presence of comparatively low quantities thereof.

SUMMARY OF THE INVENTION

The present invention is directed to a pharmaceutical composition of S-ketamine hydrochloride, comprising S-ketamine hydrochloride and water; wherein the pharmaceutical composition does not contain an antimicrobial preservative.

In an embodiment, the present invention is directed to a pharmaceutical composition of S-ketamine hydrochloride; wherein the formulation does not contain an antimicrobial preservative; and wherein the pharmaceutical composition is formulated for nasal administration.

The present invention is further directed to a pharmaceutical composition of S-ketamine hydrochloride; wherein the formulation does not contain an antimicrobial preservative; and wherein the pharmaceutical composition further comprises a penetration enhancer, preferably TUDCA.

In another embodiment, the present invention is directed to a pharmaceutical composition of S-ketamine hydrochloride; wherein the formulation does not contain an antimicrobial preservative; and wherein the pharmaceutical composition further comprises TUDCA; wherein the TUDCA is present in a concentration in the range of from about 1.0 mg/mL to about 25 mg/m L.

BRIEF DESCRIPTION OF THE FIGURES

FIG. 1 illustrated Esketamine Plasma Levels dosing Formulations 5-A through 5-D at 10 µL/rat.

FIG. 2 illustrated Esketamine Plasma Levels dosing Formulations 5-A and 5-C at 25 µL/rat.

FIG. 3 illustrated Esketamine Plasma Levels dosing Formulations 5-A and Reference Formulation 5-E at 25 µL/rat.

DETAILED DESCRIPTION OF THE INVENTION

The present invention is directed to pharmaceutical composition of S-ketamine, wherein the pharmaceutical composition does not contain an antimicrobial preservative.

The pharmaceutical compositions of the present invention are based on the unexpected finding that S-ketamine hydrochloride exhibits preservative properties. Thus, when formulating pharmaceutical compositions of S-ketamine hydrochloride, particularly aqueous liquid compositions, preservatives can be completely omitted while still achieving desired shelf life. Further, although the pharmaceutical compositions of S-ketamine hydrochloride of the present invention do not contain an antibacterial preservative, said compositions do not need to manufactured under aseptic conditions and/or do not need to be sterilized after production.

Additionally, wherein the pharmaceutical compositions of the present invention are formulated for nasal administration, the absence of preservatives results in the elimination of adverse effects associated with said preservatives, including for example, irritation or damage of the mucosal membrane.

As used herein, unless otherwise noted, the terms "S-ketamine", "S-ketamine hydrochloride" and "esketamine" shall mean the (S)-enantiomer of ketamine, as its corresponding hydrochloride salt, a compound of formula (I)

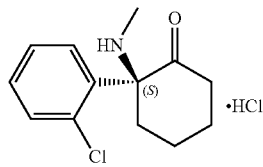

also known as (S)-2-(2-chlorophenyl)-2-(methylamino) cyclohexanone hydrochloride.

As used herein, the term "composition" is intended to encompass a product comprising the specified ingredients in the specified amounts, as well as any product which results, directly or indirectly, from combinations of the specified ingredients in the specified amounts.

The term "pharmaceutical composition" includes any pharmaceutical preparation or formulation that is customized for being administered to a human being or animal. Preferably, the composition contains one or more physiologically acceptable carriers and/or excipients. Preferably, the pharmaceutical compositions of the present invention contain water.

To prepare a pharmaceutical composition of the present invention, 5-ketamine hydrochloride as the active ingredient is intimately admixed with a pharmaceutical carrier, preferably water, according to conventional pharmaceutical compounding techniques, which carrier may take a wide variety of forms depending of the form of preparation desired for administration. Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

In an embodiment, the present invention is directed to an aqueous formulation of S-ketamine, comprising water and S-ketamine; wherein the S-ketamine is present in an amount in the range of from about 100 mg/mL to about 250 mg/mL, or any amount or range therein, based on the total volume of the pharmaceutical composition. Preferably, the S-ketamine is present in an amount in the range of from about 150 mg/ml to about 200 mg/mL, or any amount or range therein. More preferably, the S-ketamine is present in an amount in the range of from about 150 mg/mL to about 175 mg/mL, or any amount or range therein. More preferably, the S-Ketamine is present in an amount in the range of from about 160 mg/mL to about 163 mg/mL, for example, in an amount of about 161.4 mg/mL.

In an embodiment, the present invention is directed to an aqueous formulation of S-ketamine, comprising water and S-ketamine; wherein the S-ketamine is present in an amount in the range of from about eq. 100 mg/mL to about eq. 250 mg/mL, or any amount or range therein, based on the total volume of the pharmaceutical composition. Preferably, the S-ketamine is present in an amount in the range of from about eq. 125 mg/ml to about eq. 180 mg/mL, or any amount or range therein. More preferably, the S-ketamine is present in an amount in the range of from about eq. 140 mg/mL to about eq. 160 mg/mL, or any amount or range therein, for example, in an amount of about eq. 140 mg/m L.

The pharmaceutical compositions according to the invention are preferably an aqueous formulation. As used herein, unless otherwise noted, the term "aqueous" shall mean that the primary liquid component of the formulation is water. Preferably, water constitutes greater than about 80 wt % of the liquid component of the pharmaceutical composition, more preferably greater than about 90 wt %, more preferably greater than about 95 wt %, more preferably about 98 wt %.

In an embodiment of the present invention, the water content of the composition is within the range of 85±14 wt.-%, more preferably 85±12 wt.-%, still more preferably 85±10 wt.-%, most preferably 85±7.5 wt.-% and in particular 85±5 wt.-%, based on the total weight of the composition.

In another embodiment of the present invention, the water content of the composition is within the range of 90±14 wt.-%, more preferably 90±12 wt.-%, still more preferably 90±10 wt.-%, most preferably 80±7.5 wt.-% and in particular 90±5 wt.-%, based on the total weight of the composition.

In another embodiment of the present invention, the water content of the composition is within the range of 95±4.75 wt.-%, more preferably 95±4.5 wt.-%, still more preferably 95±4 wt.-%, yet more preferably 95±3.5 wt.-%, most preferably 95±3 wt.-% and in particular 95±2.5 wt.-%, based on the total weight of the composition.

In another embodiment of the present invention, the water content of the composition is within the range of from 75 to 99.99 wt.-%, more preferably 80 to 99.98 wt.-%, still more preferably 85 to 99.95 wt.-%, yet more preferably 90 to 99.9 wt.-%, most preferably 95 to 99.7 wt.-% and in particular 96.5 to 99.5 wt.-%, based on the total weight of the composition.

In another embodiment, the pharmaceutical compositions of the present invention further comprises one or more buffers and/or buffer systems (i.e. conjugate acid-base-pairs).

As used herein, the term "buffer" shall mean any solid or liquid composition (preferably an aqueous, liquid composition) which when added to an aqueous formulation adjusts the pH of said formulation. One skilled in the art will recognize that a buffer may adjust the pH of the aqueous formulation in any direction (toward more acidic, more basic or more neutral pH). Preferably, the buffer is pharmaceutically acceptable.

Suitably examples of buffers which may be used in the aqueous formulations of the present invention include, but are not limited to citric acid, sodium dihydrogen phosphate, disodium hydrogen phosphate, acetic acid, boric acid, sodium borate, succinic acid, tartaric acid, malic acid, lactic acid, furmaric acid, and the like. Preferably, the buffer or buffer system is selected from the group consisting of NaOH, citric acid, sodium dihydrogen phosphate and disodium hydrogen phosphate.

In an embodiment, the buffer is selected to adjust the pH of the S-ketamine hydrochloride pharmaceutical compositions of the present invention (e.g. the aqueous formulations described herein) into a pH in the range of from about pH 3.5 to about pH 6.5, or any amount or range therein. Preferably, the buffer is selected to adjust the pH of the S-ketamine hydrochloride compositions of the present invention to about in the range of from about pH 4.0 to about pH 5.5, or any amount or range therein, more preferably, in the range of from about pH 4.5 to about pH 5.0, or any amount or range therein.

Preferably, the concentration of the buffer and buffer system, respectively, preferably NaOH, is adjusted to provide a sufficient buffer capacity.

In an embodiment, the present invention is directed to a pharmaceutical composition comprising S-ketamine hydrochloride, water, and a buffer or buffer system, preferably NaOH; wherein the buffer or buffer system is present in an amount sufficient to yield a formulation with a pH in the range of from about pH 4.0 to about pH 6.0, or any amount or range therein.

The pharmaceutical compositions of the present invention do not contain a preservative.

As used herein, unless otherwise noted, the terms "antimicrobial preservative" and "preservative" preferably refer to any substance that is usually added to pharmaceutical compositions in order to preserve them against microbial degradation or microbial growth. In this regard, microbial growth typically plays an essential role, i.e. the preservative serves the main purpose of avoiding microbial contamination. As a side aspect, it may also be desirable to avoid any effect of the microbes on the active ingredients and excipients, respectively, i.e. to avoid microbial degradation.

Representative examples of preservatives include, but are not limited to, benzalkonium chloride, benzethonium chloride, benzoic acid, sodium benzoate, benzyl alcohol, bronopol, cetrimide, cetylpyridinium chloride, chlorhexidine, chlorbutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, sodium propionate, thimerosal, methyl paraben, ethyl paraben, propyl paraben, butyl paraben, isobutyl paraben, benzyl paraben, sorbic acid, and potassium sorbate.

The complete absence of preservatives in the pharmaceutical compositions of the present invention is preferred when the content of S-ketamine hydrochloride is sufficiently high so that due to its preservative property the desired shelf life or in use stability can be achieved by the presence of the drug itself. Preferably, under these circumstances the concentration of S-ketamine hydrochloride is at least eq. 120 mg/mL, preferably in the range of from about eq. 120 mg/mL to about eq. 175 mg/ml, or any amount or range therein, more preferably in an amount in the range of from about eq. 125 mg/mL to about eq. 150 mg/m L, or any amount or range therein, for example at about eq. 126 mg/mL or at about eq. 140 mg/mL.

As used herein, the terms "penetration agent", "penetration enhancer", and "penetrant" refer to any substance that increases or facilitates absorption and/or bioavailability of the active ingredient (e.g. S-ketamine hydrochloride) of a pharmaceutical composition. Preferably, the penetration agents increases or facilitates absorption and/or bioavailability of the active ingredient (e.g. S-ketamine hydrochloride) of a pharmaceutical composition, following nasal administration (i.e. increases or facilitates absorption and/or bioavailability of the active ingredient through the mucosal membrane).

Suitable examples include, but are not limited to tetradecyl maltoside, sodium glycocholate, tauroursodeoxycholic acid (TUDCA), lecithines, and the like; and chitosan (and salts), and surface active ingredients such as benzalkonium chloride, sodium dodecyl sulfate, sodium docusate, polysorbates, laureth-9, oxtoxynol, sodium deoxycholate, polyarginine, and the like. Preferably, the penetration agent is tauroursodeoxycholic acid (TUDCA).

The penetration agent may work via any mechanism, including for example by increasing the membrane fluidity, creating transient hydrophilic pores in the epithelial cells, decreasing the viscosity of the mucus layer or opening up tight junctions. Some penetration agents (for example bile salts and fusidic acid derivatives) may also inhibit the enzymatic activity in the membrane, thereby improving bioavailability of the active ingredient.

Preferably, the penetration agent is selected to meet one or more, more preferably all, of the following general requirements:

(a) It is effective at increasing absorption (preferably nasal absorption) of the active ingredient, preferably in a temporary and/or reversible manner;
(b) It is pharmacologically inert;
(c) It is non-allergic, non-toxic and/or non-irritating;
(d) It is highly potent (effective in small amounts);
(e) It is compatible with the other components of the pharmaceutical composition;
(f) It is odorless, colorless and/or tasteless;
(g) It is accepted by regulatory agencies; and
(h) It is inexpensive and available in high purity.

In an embodiment of the present invention, the penetration agent is selected to increase penetration (absorption and/or bioavailability of the S-ketamine hydrochloride) without nasal irritation. In another embodiment of the present invention, the penetration agent is selected to improve absorption and/or bioavailability of the S-ketamine hydrochloride; and further selected to enhance uniform dosing efficacy.

In an embodiment, the present invention is directed to a pharmaceutical composition comprising S-ketamine and water; herein the pharmaceutical composition does not contain an antimicrobial preservative; and wherein the pharmaceutical compositions further contains a penetration enhancer, preferably TUDCA.

In another embodiment, the present invention is directed to a pharmaceutical composition comprising S-ketamine and water; herein the pharmaceutical composition does not contain an antimicrobial preservative; and wherein the pharmaceutical compositions further contains tauroursodeoxycholic acid (TUDCA); wherein the TUDCA is present in a concentration in the range of from about 1.0 mg/mL to about 25.0 mg/mL, or any amount or range therein, preferably in a concentration in the range of from about 2.5 mg/mL to about 15 mg/mL, or any amount or range therein, preferably in a concentration in the range of from about 5 mg/mL to about 10 mg/mL, or any amount or range therein. In another embodiment, the present invention is directed to pharmaceutical composition wherein the TUDCA is present at a concentration of about 5 mg/mL. In another embodiment, the present invention is directed to pharmaceutical composition wherein the TUDCA is present at a concentration of about 10 mg/mL.

The pharmaceutical compositions of the present invention may further contain one or more additional excipients for example, wetting agents, surfactant components, solubilizing agents, thickening agents, colorant agents, antioxidant components, and the like.

Examples of a suitable antioxidant component, if used, include, but are not limited to one or more of the following: sulfites; ascorbic acid; ascorbates, such as sodium ascorbate, calcium ascorbate, or potassium ascorbate; ascorbyl palmitate; fumaric acid; ethylene diamine tetraacetic acid (EDTA) or its sodium or calcium salts; tocopherol; gallates, such as propyl gallate, octyl gallate, or dodecyl gallate; vitamin E; and mixtures thereof. The antioxidant component provides long term stability to the liquid compositions. Addition of the antioxidant component can help enhance and ensure the stability of the compositions and renders the compositions stable even after six months at 40° C. A suitable amount of the antioxidant component, if present, is about 0.01 wt.-% to about 3 wt.-%, preferably about 0.05 wt.-% to about 2 wt.-%, of the total weight of the composition.

Solubilizing and emulsifying agents can be included to facilitate more uniform dispersion of the active ingredient or other excipient that is not generally soluble in the liquid carrier. Examples of a suitable emulsifying agent, if used, include, but are not limited to, for example, gelatin, cholesterol, acacia, tragacanth, pectin, methyl cellulose, carbomer, and mixtures thereof. Examples of a suitable solubilizing agent include polyethylene glycol, glycerin, D-mannitol, trehalose, benzyl benzoate, ethanol, trisaminomethane, cholesterol, triethanolamine, sodium carbonate, sodium citrate, sodium salicylate, sodium acetate, and mixtures thereof.

Preferably, the solubilizing agent includes glycerin. The solubilizing or emulsifying agent is/are generally present in an amount sufficient to dissolve or disperse the active ingredient, i.e. S-ketamine, in the carrier. Typical amounts when a solubilizing or an emulsifier are included are from about 1 wt.-% to about 80 wt.-%, preferably about 20 wt.-% to about 65 wt.-%, and more preferably about 25 wt.-% to about 55 wt.-%, of the total weight of the composition.

A suitable isotonizing agent, if used, includes sodium chloride, glycerin, D-mannitol, D-sorbitol, glucose, and mixtures thereof. A suitable amount of the isotonizing agent, when included, is typically about 0.01 wt.-% to about 15 wt.-%, more preferably about 0.3 wt.-% to about 4 wt.-%, and more preferably about 0.5 wt.-% to about 3 wt.-%, of the total weight of the composition.

A Suspending agent or viscosity increasing agent can be added to to the pharmaceutical compositions of the present invention, to for example, increase the residence time in the nose. Suitably examples include, but are not limited to, hydroxypropyl methylcellulose, sodium carmellose, microcrystalline cellulose, carbomer, pectin, sodium alginate, chitosan salts, gellan gum, poloxamer, polyvinyl pyrrolidone, xanthan gum, and the like.

As used herein the term "shelf life" refers to the storage stability of a closed container of the pharmaceutical composition.

Preferably, the pharmaceutical compositions according to the present invention exhibit antimicrobial robustness that complies with the requirements for nasal pharmaceutical compositions (for example, the Ph. Eur. requirements). Requirements for the following organisms: *Staphylococcus aureus, Escherichia coli, Pseudomonas aeruginosa, Candida albicans, Aspergillus niger* (for example, *A. Brasiliensis*, a niger variety), and *Micrococcus luteus* (an in-house, J&J organism) are as listed in Table 1, below.

TABLE 1

Bacterial & Fungal Requirements for Nasal Compositions

| Requirement Std. | 6 hrs | 24 hrs | 48 hrs | 7 days | 14 days | 28 days |
|---|---|---|---|---|---|---|
| Bacteria | | | | | | |
| Eur. A | — | — | log 2 | log 3 | — | NI/7 d |
| Eur. B | — | — | — | — | log 3 | NI/14 d |
| J&J | — | — | — | — | log 3 | NI/14 d |
| U.S.P. | — | — | — | — | >=2.0 | NI/14 d |
| J.P. | — | — | — | — | >=2.0 | NI/14 d |

TABLE 1-continued

Bacterial & Fungal Requirements for Nasal Compositions

| Requirement Std. | 6 hrs | 24 hrs | 48 hrs | 7 days | 14 days | 28 days |
|---|---|---|---|---|---|---|
| Fungi | | | | | | |
| Eur. A | — | — | — | — | log 2 | NI/14 d |
| Eur. B | — | — | — | — | log 1 | NI/14 d |
| J.&J. | — | — | — | — | log 2.0 | NI/14 d |
| U.S.P. | — | — | — | — | NI/Init. | NI/Init. |
| J.P. | — | — | — | — | NI/Init. | NI/Init. |

Preferably, antimicrobial robustness is achieved against one or more of *E. coli, S. aureus, Ps. Aeruginosa, S.* spp., *M. luteus* and/or *C. albicans*.

Preferably, the pharmaceutical compositions of the present invention exhibit a shelf-life under accelerated storage conditions of at least 1 month, more preferably at least 2 months, still more preferably at least 3 months, yet more preferably at least 4 months, most preferably at least 5 months and in particular at least 6 months. Preferably, the shelf life is determined according to Ph. Eur., particularly as described in the experimental section. Accelerated storage conditions preferably mean 40° C./75% Relative Humidity (% RH).

Preferably, the pharmaceutical compositions of the present invention exhibit a shelf-life under ambient conditions of at least 6 months, more preferably at least 12 months, still more preferably at least 15 months, yet more preferably at least 18 months, most preferably at least 21 months and in particular at least 24 months.

In an embodiment, the present invention is directed to a pharmaceutical composition comprising: (a) S-ketamine hydrochloride 161.4 mg/mL; (b) NaOH q.s. ad pH 4.5; wherein the NaOH is preferably added to the pharmaceutical composition as a 1N solution; (c) purified water q.s. ad 1000 µL; and wherein pharmaceutical compositions does not contain antimicrobial preservative.

In another embodiment, the present invention is directed to a pharmaceutical composition comprising: (a) S-ketamine hydrochloride @ 161.4 mg/mL; (b) NaOH q.s. ad pH 4.5; wherein the NaOH is preferably added to the pharmaceutical composition as a 1N solution; (c) purified water q.s. ad 1000 µL; and (d) TUDCA @ 1.25 mg/mL; and wherein pharmaceutical compositions does not contain antimicrobial preservative.

In another embodiment, the present invention is directed to a pharmaceutical composition comprising: (a) S-ketamine hydrochloride @ 161.4 mg/mL; (b) NaOH q.s. ad pH 4.5; wherein the NaOH is preferably added to the pharmaceutical composition as a 1N solution; (c) purified water q.s. ad 1000 µL; and (d) TUDCA @ 2.5 mg/mL; and wherein pharmaceutical compositions does not contain antimicrobial preservative.

In another embodiment, the present invention is directed to a pharmaceutical composition comprising: (a) S-ketamine hydrochloride @ 161.4 mg/mL; (b) NaOH q.s. ad pH 4.5; wherein the NaOH is preferably added to the pharmaceutical composition as a 1N solution; (c) purified water q.s. ad 1000 µL; and (d) TUDCA @ 5 mg/mL; and wherein pharmaceutical compositions does not contain antimicrobial preservative.

In another embodiment, the present invention is directed to a pharmaceutical composition comprising: (a) S-ketamine hydrochloride @ 161.4 mg/mL; (b) NaOH q.s. ad pH 4.5; wherein the NaOH is preferably added to the pharmaceutical composition as a 1N solution; (c) purified water q.s. ad 1000 µL; and (d) TUDCA @ 10 mg/mL; and wherein pharmaceutical compositions does not contain antimicrobial preservative.

In another embodiment, the present invention is directed to a pharmaceutical composition comprising: (a) S-ketamine hydrochloride @ 161.4 mg/mL; (b) NaOH q.s. ad pH 4.5; wherein the NaOH is preferably added to the pharmaceutical composition as a 1N solution; (c) purified water q.s. ad 1000 µL; and (d) TUDCA @ 15 mg/mL; and wherein pharmaceutical compositions does not contain antimicrobial preservative.

In an embodiment, the pharmaceutical composition of the present invention is prepared by adding water to the S-ketamine hydrochloride; followed by addition of 1N $NaOH_{(aq)}$ to adjust the pH of the resulting mixture to the desired pH, preferably to a pH in the range of from about pH 3.5 to about pH 6.0, more preferably to about pH in the range of from about pH 4.0 to about pH 5.0, more preferably to about pH 4.5.

In a preferred embodiment, the pharmaceutical compositions of the present invention are ready to use, i.e. do not require particular treatment steps such as dissolution in a solvent before they may be administered to the patient.

A skilled person recognizes that the pharmaceutical compositions of the present invention may alternatively be commercialized as a precursor in form of a dry powder that is to be dissolved or dispersed in an appropriate amount of water prior to the first use.

A further aspect of the invention relates to a pharmaceutical dosage form comprising the pharmaceutical composition according to the invention. All preferred embodiments that are described above in connection with the composition according to the invention also apply to the dosage form according to the invention.

In an embodiment, the dosage form according to the invention is adapted for nasal administration. Preferably, the dosage form according to the invention is adapted for administration once every couple of days, on individually determined days only; or once daily, twice daily, thrice daily, four times daily, five times daily, six times daily or even more frequently; or clustered as between 2 and up to 8 consecutive administrations within a limited time period ranging from 1 to about 60 minutes.

The present invention is further directed to methods for the treatment of depression, preferably resistant depression or treatment refractory depression, comprising administering to a subject in need thereof, a therapeutically effective amount of any of the pharmaceutical compositions a described herein. Preferably, the administration is nasal.

In an embodiment, the present invention is directed to a method for the treatment of depression, preferably resistant depression or treatment refractory depression, comprising the nasal administration of the pharmaceutical composition according to the invention as described above or of the pharmaceutical dosage form according to the invention as described above, to a subject in need thereof.

As used herein, the term "depression" shall be defined to include major depressive disorder, unipolar depression, treatment-refractory depression, resistant depression, anxious depression, bipolar depression and dysthymia (also referred to as dysthymic disorder). Preferably, the depression is major depressive disorder, unipolar depression, treatment-refractory depression, resistant depression, anxious depression or bipolar depression.

As used herein, the term "treatment-refractory or treatment-resistant depression" and the abbreviation "TRD"

shall be defined as major depressive disorder that does not respond to adequate courses of at least two antidepressants, preferably two or more antidepressants, more preferably two to three, antidepressants.

As used herein, the term "bipolar depression" is intended to mean the depression associated with, characteristic of or symptomatic of a bipolar disorder. Thus, methods of treating bipolar depression of the present invention are directed to methods which treat the depression and/or depressed phase of bipolar disorders.

One skilled in the art will recognize that the failure to respond to an adequate course of a given antidepressant may be determined retrospectively or prospectively. In an embodiment, at least one of the failures to respond to an adequate course of antidepressant is determined prospectively. In another embodiment, at least two of the failures to respond to an adequate course of antidepressant are determined prospectively. In another embodiment, at least one of the failures to respond to an adequate course of antidepressant is determined retrospectively. In another embodiment, at least two of the failures to respond to an adequate course of antidepressant are determined retrospectively.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Optimal dosages to be administered may be readily determined by those skilled in the art, and will vary with the particular compound used, the mode of administration, the strength of the preparation, the mode of administration, the number of consecutive administrations within a limited period of time (e.g. up to 60 minutes) and the advancement of the disease condition. In addition, factors associated with the particular patient being treated, including patient age, weight, diet and time of administration, will result in the need to adjust dosages.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

The following Examples are set forth to aid in the understanding of the invention, and are not intended and should not be construed to limit in any way the invention set forth in the claims which follow thereafter.

EXAMPLE 1

Microbial Challenge Test for Nasal Spray Pharmaceutical Composition Containing S-ketamine Hydrochloride (eq. 140 mg/ml An aqueous formulation of S-ketamine hydrochloride referred to as "S-ketamine eq. 140 mg/ml below, was prepared by mixing S-ketamine hydrochloride (at a concentration of 161.4 mg/ml) in water and then adding 1N $NaOH_{(aq)}$ to pH 5.0.

A challenge test was initiated to investigate whether the formulation could prevent microorganisms from proliferating. The challenge test consisted of challenging the formulation with a prescribed inoculum of microorganisms. The inoculated formulation was then stored at room temperature and at specified time intervals a sample was withdrawn to count the microorganisms in the sample.

As shown in Table 2 below, the challenge test results on S-ketamine eq. 140 mg/ml pH 5.0 show that S-ketamine eq. 140 mg/ml pH 5.0 reduced the original spike ($10^5$-$10^6$ CFU/ml) of bacteria (i.e. *Pseudomonas aeruginosa, Staphylococcus aureus, Escherichia coli* and environmental isolate *Staphylococcus haemolyticus*) and also of the yeast *Candida albicans*. S-ketamine eq. 140 mg/ml pH 5.0 was not able to reduce the original spike of *Aspergillus brasiliensis* to the same extent as for the bacteria and yeast, but no increase was observed after 28 days of incubation at room temperature.

TABLE 2

Challenge Test S-ketamine eq. 140 mg/ml pH 5.0 (CFU/ml)

| Organism | Blank at 0 hours | Product at 0 hours | at 2 days | at 7 days | at 14 days | at 28 days |
|---|---|---|---|---|---|---|
| *A. brasiliensis* | 1.50 × $10^5$ | 1.90 × $10^5$ | ND | 4.80 × $10^4$ | 5.80 × $10^4$ | 2.65 × $10^4$ |
| *C. albicans* | 1.15 × $10^5$ | 6.50 × $10^4$ | ND | <5 | <5 | <5 |
| *P. aeruginosa* | 2.65 × $10^5$ | 1.59 × $10^4$ | <50 | <5 | <5 | <5 |
| *S. aureus* | 1.90 × $10^5$ | 1.70 × $10^5$ | <50 | <5 | <5 | <5 |
| *E. coli* | 1.20 × $10^5$ | 6.00 × $10^4$ | <50 | <5 | <5 | <5 |
| *S. haemolyticus* | 1.20 × $10^5$ | 7.50 × $10^4$ | <50 | <5 | <5 | <5 |

ND: not determined

EXAMPLE 2

Microbial Challenge for Nasal Spray Pharmaceutical Composition Containing S-ketamine Hydrochloride Aqueous formulation of S-ketamine hydrochloride as listed in Table 3, below, were prepared by mixing S-ketamine hydrochloride (at the listed concentrations) in water and then adding 1N $NaOH_{(aq)}$ to the listed pH levels. Formulation F-5 additionally contained 10 mg/mL of tauroursodeoxycholic acid (TUDCA).

TABLE 3

Composition of edge of failure batches

| Formulation | Concentration API(mg/ml) | pH |
|---|---|---|
| F-1 | eq. 126 | 4.0 |
| F-2 | eq. 140 | 4.5 |
| F-3 | eq. 126 | 5.0 |
| F-4 | eq. 126 | 4.5 |
| F-5 | eq. 140 | 4.5 |

*This formulation also contained 10 mg/mL Tauroursodeoxycholic acid (TUDCA)

Low Level *A brasiliensis* Challenge

The formulations listed in Table 3, above were subjected to a low level challenge with *A. brasiliensis* to evaluate whether the formulations would be able to reduce this lower spike, with results as shown in Table 4, below. A spike of $10^3$ CFU/ml was chosen instead of $10^5$-$10^6$ CFU/ml, which is the standard spike for a challenge test.

TABLE 4

Low Level Challenge with *A. brasiliensis*

| | Product (CFU/ml) | | | |
|---|---|---|---|---|
| Formulation | 0 hours | 7 days | 14 days | 28 days |
| F-1 | 4.45E+02 | 2.35E+02 | 2.15E+02 | 1.75E+02 |
| F-2 | 3.80E+02 | 2.50E+02 | 2.00E+02 | 2.00E+02 |
| F-3 | 5.50E+02 | 2.75E+02 | 2.65E+02 | 1.10E+02 |

TABLE 4-continued

Low Level Challenge with *A. brasiliensis*

| | Product (CFU/ml) | | | |
|---|---|---|---|---|
| Formulation | 0 hours | 7 days | 14 days | 28 days |
| F-4 | 3.85E+02 | 2.70E+02 | 2.60E+02 | 1.55E+02 |
| F-5 | 4.10E+02 | 4.00E+02 | 3.15E+02 | 2.25E+02 |
| Blank | 4.75E+02 | NA | NA | NA |

The results, as listed in Table 3, above, show that in none of the tested formulation was an increase in *Aspergillus brasiliensis* observed after 28 days of incubation, rather a minor and slow decrease was observed.

Full AET Challenge Test

The formulations listed in Table 3 were additionally subjected to a Full AET challenge, with results for the individual formulations are shown in Tables 5-9, below. Additionally, Table 10 below, provides results for a Full AET challenge of a reference formulation containing 0.00 mg/mL S-ketamine hydrochloride, denatonium benzoate (to mimic the taste of the S-ketamine HCl formulation(s)), and adjusted to pH 5.21 with 1N NaOH.

TABLE 5

Full AET Challenge Test
Formulation F-1: S-ketamine eq. 126 mg/ml pH 4.0 (CFU/ml)

| | | Product | | | | |
|---|---|---|---|---|---|---|
| Organism | Blank at 0 hrs | at 0 hrs | at 2 days | at 7 days | at 14 days | at 28 Days |
| *A. brasiliensis* | 1.55 × $10^5$ | 2.15 × $10^5$ | ND | 5.30 × $10^4$ | 2.10 × $10^4$ | 3.5 × $10^3$ |
| *C. albicans* | 1.05 × $10^5$ | 1.15 × $10^4$ | ND | <5 | <5 | <5 |
| *P. aeruginosa* | 5.05 × $10^5$ | 1.10 × $10^4$ | <50 | <5 | <5 | <5 |
| *S. aureus* | 6.00 × $10^5$ | 6.25 × $10^5$ | <50 | <5 | <5 | <5 |
| *E. coli* | 6.05 × $10^5$ | 4.00 × $10^4$ | <50 | <5 | <5 | <5 |
| *M. luteus* | 1.65 × $10^5$ | 7.50 × $10^4$ | <50 | <5 | <5 | <5 |

ND: not determined

TABLE 6

Full AET Challenge Test
Formulation F-2: S-ketamine eq. 140 mg/ml pH 4.5 (CFU/ml)

| | | Product | | | | |
|---|---|---|---|---|---|---|
| Organism | Blank at 0 hrs | at 0 hrs | at 2 days | at 7 days | at 14 days | at 28 days |
| *A. brasiliensis* | 1.55 × $10^5$ | 1.20 × $10^5$ | ND | 1.65 × $10^4$ | 1.00 × $10^4$ | 2.0 × $10^3$ |
| *C. albicans* | 1.05 × $10^5$ | 1.15 × $10^4$ | ND | <5 | <5 | <5 |
| *P. aeruginosa* | 5.05 × $10^5$ | 7.55 × $10^4$ | <50 | <5 | <5 | <5 |
| *S. aureus* | 6.00 × $10^5$ | 5.70 × $10^5$ | <50 | <5 | <5 | <5 |
| *E. coli* | 6.05 × $10^5$ | 2.80 × $10^4$ | <50 | <5 | <5 | <5 |
| *M. luteus* | 1.65 × $10^5$ | 1.70 × $10^4$ | <50 | <5 | <5 | <5 |

ND: not determined

TABLE 7

Full AET Challenge Test
Formulation F-3: S-ketamine eq. 126 mg/ml pH 5.0 (CFU/ml)

| Organism | Blank at 0 hrs | Product at 0 hrs | at 2 days | at 7 days | at 14 days | at 28 days |
|---|---|---|---|---|---|---|
| A. brasiliensis | $1.55 \times 10^5$ | $1.90 \times 10^5$ | ND | $3.50 \times 10^4$ | $2.15 \times 10^4$ | $8.0 \times 10^3$ |
| C. albicans | $1.05 \times 10^5$ | $1.60 \times 10^4$ | ND | <5 | <5 | <5 |
| P. aeruginosa | $5.05 \times 10^5$ | $1.03 \times 10^4$ | <50 | <5 | <5 | <5 |
| S. aureus | $6.00 \times 10^5$ | $6.05 \times 10^5$ | <50 | <5 | <5 | <5 |
| E. coli | $6.05 \times 10^5$ | $2.00 \times 10^4$ | <50 | <5 | <5 | <5 |
| M. luteus | $1.65 \times 10^5$ | $1.60 \times 10^4$ | <50 | <5 | <5 | <5 |

ND: not determined

TABLE 8

Full AET Challenge Test
Formulation F-4: S-ketamine eq. 126 mg/ml pH 4.5 (CFU/ml)

| Organism | Blank at 0 hrs | Product at 0 hrs | at 2 days | at 7 days | at 14 days | at 28 days |
|---|---|---|---|---|---|---|
| A. brasiliensis | $1.55 \times 10^5$ | $2.10 \times 10^5$ | ND | $5.30 \times 10^4$ | $2.10 \times 10^4$ | $5.5 \times 10^3$ |
| C. albicans | $1.05 \times 10^5$ | $2.85 \times 10^4$ | ND | <5 | <5 | <5 |
| P. aeruginosa | $5.05 \times 10^5$ | $8.35 \times 10^4$ | <50 | <5 | <5 | <5 |
| S. aureus | $6.00 \times 10^5$ | $7.60 \times 10^5$ | <50 | <5 | <5 | <5 |
| E. coli | $6.05 \times 10^5$ | $4.80 \times 10^4$ | <50 | <5 | <5 | <5 |
| M. luteus | $1.65 \times 10^5$ | $7.00 \times 10^4$ | <50 | <5 | <5 | <5 |

ND: not determined

TABLE 9

Full AET Challenge Test
Formulation F-5: S-ketamine eq. 140 mg/ml
pH 4.5, TUDCA @ 10 mg/mL (CFU/ml)

| Organism | Blank at 0 hrs | Product at 0 hrs | at 2 days | at 7 days | at 14 days | at 28 days |
|---|---|---|---|---|---|---|
| A. brasiliensis | $1.55 \times 10^5$ | $8.50 \times 10^5$ | ND | $4.15 \times 10^4$ | $2.40 \times 10^4$ | $8.5 \times 10^3$ |
| C. albicans | $1.05 \times 10^5$ | $1.30 \times 10^4$ | ND | <5 | <5 | <5 |
| P. aeruginosa | $5.05 \times 10^5$ | <50 | <50 | <5 | <5 | <5 |
| S. aureus | $6.00 \times 10^5$ | $6.20 \times 10^5$ | <50 | <5 | <5 | <5 |
| E. coli | $6.05 \times 10^5$ | <50 | <50 | <5 | <5 | <5 |
| M. luteus | $1.65 \times 10^5$ | $6.50 \times 10^4$ | <50 | <5 | <5 | <5 |

ND: not determined

TABLE 10

Full AET Challenge Test
Reference Formulation: 0.0 mg/mL S-ketamine, Denatonium Benzoate (to mimic S-ketamine HCl taste), pH 5.21

| Organism | Blank at 0 hours | At 0 hours | At 2 days | At 7 days | At 14 days | At 28 days |
|---|---|---|---|---|---|---|
| A. Brasileinsis | $1.55 \times 10^5$ | $1.75 \times 10^5$ | — | $4.35 \times 10^4$ | $8.00 \times 10^4$ | $9.00 \times 10^4$ |
| C. Albicans | $1.05 \times 10^5$ | $1.20 \times 10^5$ | — | $1.02 \times 10^5$ | $1.40 \times 10^5$ | $1.30 \times 10^5$ |
| P. aeruginosa | $5.05 \times 10^5$ | $4.05 \times 10^5$ | $6.55 \times 10^5$ | >$2.00 \times 10^5$ | $9.75 \times 10^5$ | $2.40 \times 10^6$ |
| S. aureus | $6.00 \times 10^5$ | $5.15 \times 10^5$ | $3.90 \times 10^5$ | $1.55 \times 10^2$ | <5 | <5 |
| E. coli | $6.05 \times 10^5$ | $5.55 \times 10^5$ | $6.40 \times 10^5$ | >$2.00 \times 10^5$ | $8.25 \times 10^5$ | $1.09 \times 10^6$ |
| M. luteus | $1.65 \times 10^5$ | $6.00 \times 10^4$ | $8.50 \times 10^4$ | $4.30 \times 10^2$ | $2.50 \times 10^3$ | $3.90 \times 10^2$ |

As shown in Tables 5-10 above, after 28 days, all the tested formulations reduced the original spike ($10^5$-$10^6$ CFU/ml) of bacteria (i.e. *Pseudomonas aeruginosa, Staphylococcus aureus, Escherichia coli* and environmental isolate *Staphylococcus haemolyticus*) and environmental *Micrococcus Luteus*, and also of the yeast *Candida albicans*. The tested formulations were not able to reduce the original spike of *Aspergillus brasiliensis* to the same extent as for the bacteria and yeast, but no increase was observed after 28 days of incubation at room temperature.

In summary, the results presented in Biological Example 1 and Biological Example 2 indicated that S-ketamine hydrochloride exhibits strong antimicrobial properties against *Pseudomonas aeruginosa, Staphylococcus aureus, Escherichia coli*, environmental isolate *Staphylococcus haemolyticus*, environmental *Micrococcus Luteus*, and the yeast *Candida albicans*. For *Aspergillus brasiliensis* the decrease in microorganisms is less pronounced, but no increase was observed, indicating some inhibitory activity.

EXAMPLE 3

Rat pK Penetration Studies

Rat Study Procedure:

Male Sprague Dawley rats weighing around 250 g were housed individually in cages of 800 cm² with limited access under routine test conditions of temperature (20° C.-24° C.), relative humidity (45%-65%) and 12/12 light cycle. Nine male Sprague Dawley rats per formulation were tested. The animals were shortly anesthetized with isoflurane (2-2.5% for 5 minutes) and were then dosed intranasally. The test formulations were dosed at a volume of 10 µl/rat in a single dose. The approximate body weight of the rats was 250 g, thus S-ketamine was dosed at ±6 mg/kg. Intranasal dosing was done by placing a small pipette at the opening of the right nostril, then the compound was given and the rat was kept for another minute under anesthesia. Afterwards, the rat was placed back in his cage. Blood for pharmacokinetics was taken at 2.5, 5, 10 and 15 minutes after dosing via the tail vein.

Formulation 3-A:

S-ketamine hydrochloride (eq. 150 mg/mL) was mixed with water and the pH of the resulting mixture adjusted with 1N NaOH to pH 4.52.

Formulations 3-B, 3-C, 3-D:

S-ketamine hydrochloride (eq. 150 mg/mL) and TUDCA (3-B: @1.25 mg/mL, 3-C: @5.0 mg/mL, 3-D: @10 mg/mL)

were mixed with water and the pH of the resulting mixture adjusted with 1N NaOH to pH 4.51.

Formulation 3-E:

S-ketamine hydrochloride (eq. 150 mg/mL) was mixed with water and the pH of the resulting mixture adjusted with 1N NaOH to pH 3.77.

Formulation 3-F:

S-ketamine hydrochloride (eq. 150 mg/mL) was mixed with water, then citric acid monohydrate at 2.73 mg/ml and the pH of the resulting mixture adjusted with 1N NaOH to pH 4.45.

Formulations 3-A through 3-F were tested according to the procedure as described above, with measured plasma levels of S-ketamine as listed in Table 11, below.

TABLE 11

Rat pK Study Results

| Formulations | Plasma Level Mean ± SEM (ng/mL) | | | |
| --- | --- | --- | --- | --- |
| | 2.5 min | 5 min | 10 min | 15 min |
| 3-A | 150 ± 24 | 254 ± 24 | 374 ± 26 | 344 ± 29 |
| 3-B | 135 ± 16 | 288 ± 24 | 379 ± 102 | 353 ± 37 |
| 3-C | 246 ± 28 | 499 ± 52 | 522 ± 47 | 446 ± 35 |
| 3-D | 283 ± 24 | 474 ± 41 | 430 ± 32 | 338 ± 28 |
| 3-E | 145 ± 24 | 240 ± 24 | 296 ± 22 | 277 ± 29 |
| 3-F | 144 ± 22 | 217 ± 20 | 292 ± 31 | 284 ± 36 |

EXAMPLE 4

Dog pK Penetration Studies

Beagle dogs weighing from 7 to 12 kg were used in this study. The dogs were housed separately in barriered testing rooms with limited access, and placed in individual pens under routine test conditions of temperature (18° C.-25° C.), ventilation (10-15 cycles/hour) and illumination.

Four beagle dogs per formulation were tested, 2 males and 2 females per group. The test formulations were dosed at 3 mg/kg, a volume of 20 μl/kg in a single dose was given. The animals were dosed intranasally by placing a small pipette at the opening of the right nostril. For the next minute, the head of the dog was tilted so no fluid could run out of the nose or into the throat. Afterwards, the dog was placed back in his pen.

Blood for pharmacokinetics were taken at 5, 10, 15 and 30 minutes after dosing via the jugular vein.

Formulation 4-A:

S-ketamine hydrochloride (eq. 150 mg/mL) was mixed with water and the pH of the resulting mixture adjusted with 1N NaOH to pH 4.52.

Formulation 4-B:

S-ketamine hydrochloride (eq. 150 mg/mL) and TUDCA (10 mg/mL) were mixed with water and the pH of the resulting mixture adjusted with 1N NaOH to pH 4.51.

Formulations 4-A and 4-B were tested according to the procedure as described above, with measured plasma levels of S-ketamine as listed in Table 12, below.

TABLE 12

Dog pK Study Results

| | Plasma Level Mean ± SEM (ng/mL) | |
| --- | --- | --- |
| Time (min) | Formulation 4-A | Formulation 4-B |
| 5 | 613 ± 206 | 3296 ± 1901 |
| 10 | 681 ± 265 | 1728 ± 203 |
| 15 | 380 ± 66 | 10556 ± 397 |
| 30 | 307 ± 69 | 192 ± 40 |

EXAMPLE 5

Rat pK Study (KET-04/KET-06

Rat Study Procedure:

Male Sprague Dawley rats weighing around 250 g were housed individually in cages of 800 cm² with limited access under routine test conditions of temperature (20° C.-24° C.), relative humidity (45%-65%) and 12/12 light cycle. Nine male Sprague Dawley rats per formulation were tested. The animals were shortly anesthetized with isoflurane (2-2.5% for 5 minutes) and were then dosed intranasally. The test formulations were dosed at a volume of 10 μl/rat or 25 μl/rat (as noted below) in a single dose. The approximate body weight of the rats was 250 g, thus S-ketamine was dosed at ±6 mg/kg. Intranasal dosing was done by placing a small pipette at the opening of the right nostril, then the compound was given and the rat was kept for another minute under anesthesia. Afterwards, the rat was placed back in his cage. Blood for pharmacokinetics was taken at 2.5, 5, 10 and 15 minutes after dosing via the tail vein.

Formulation 5-A:

S-ketamine hydrochloride (eq. 150 mg/mL) was mixed with water and the pH of the resulting mixture adjusted with 1N NaOH to pH 4.5.

Formulations 5-B, 5-C, 5-D:

S-ketamine hydrochloride (eq. 150 mg/mL) and TUDCA (5-B: @5 mg/mL, 5-C: @10.0 mg/mL, 5-D: @15 mg/mL) were mixed with water and the pH of the resulting mixture adjusted with 1N NaOH to pH 4.5.

Reference Formulation 5-E:

TUDCA @ 10 mg/mL

Formulations 5-A through 5-D and reference formulation 5-E were tested according to the procedure as described above, with measured plasma levels of S-ketamine (in ng/mL) as a function of time, as shown in FIGS. 1, 2, and 3.

Formulations 5-A through 5-D and reference formulation 5-E were tested according to the procedure as described above, with measured S-ketamine and TUDCA plasma levels, as listed in Table 13, below.

TABLE 13

Rat pK Study Results

| Formulations | 2.5 min | 5 min | 10 min | 15 min |
| --- | --- | --- | --- | --- |
| | S-Ketamine Plasma Level Mean ± SEM (ng/mL) Dosing 10 μl/rat | | | |
| 5-A | 130 ± 12 | 271 ± 19 | 367 ± 33 | 352 ± 37 |
| 5-B | 365 ± 76 | 511 ± 53 | 525 ± 71 | 430 ± 60 |

TABLE 13-continued

Rat pK Study Results

| Formulations | 2.5 min | 5 min | 10 min | 15 min |
|---|---|---|---|---|
| 5-C | 494 ± 62 | 681 ± 60 | 623 ± 65 | 492 ± 60 |
| 5-D | 422 ± 53 | 588 ± 78 | 556 ± 72 | 432 ± 51 |
| S-Ketamine Plasma Level Mean ± SEM (ng/mL) Dosing 25 µL/rat | | | | |
| 5-A | 339 ± 109 | 642 ± 143 | 899 ± 118 | 797 ± 143 |
| 5-C | 732 ± 246 | 1154 ± 304 | 1018 ± 261 | 997 ± 183 |
| TUDCA Plasma Level Mean ± SEM (ng/mL) Dosing 25 µL/rat | | | | |
| 5-C | 250 ± 17 | 346 ± 27 | 303 ± 35 | 242 ± 32 |
| 5-E | 624 ± 128 | 1209 ± 219 | 822 ± 152 | 756 ± 118 |

Nasal Cavity Histopathology

Nasal cavity (respiratory epithelium) histology was visually evaluated and scored for tissue damage, including but not limited to degeneration and detachment, as follows: 1=minimal, 2=slight, 3=moderate, 4=marked, 5=severe/massive.

Respiratory epithelium from rats treated with Formulations 5-A through 5-D at 1 µL/rat and rats treated with Formulation 5-A, 5-C and reference formulation 5-E at 25 µL/rat were evaluated and scored as described above, with results as listed in Table 14, below.

TABLE 14

Nasal cavity (Respiratory Epithelium) Histopathology

| Formulations dosed @ 10 µl/rat | |
|---|---|
| 5-A | Minimal degeneration of respiratory epithelium; No tissue change |
| 5-B and 5-C | Slight to moderate degeneration of respiratory epithelium, with/without detachment of respiratory epithelium |
| 5-D | Slight degeneration of respiratory epithelium, with detachment of respiratory epithelium |
| Formulations dosed at 25 µl/rat | |
| 5-A | Slight degeneration of respiratory epithelium; Slightly more severe than minimal scope |
| 5-C | Minimal to moderate degeneration of respiratory epithelium; More variable than Formulation 5-A |
| 5-E (Ref.) | No degeneration |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A method comprising:
   intranasally administering to a human patient a pharmaceutical composition comprising (S)-2-(2-chlorophenyl)-2-(methylamino)cyclohexanone hydrochloride and water; wherein the (S)-2-(2-chlorophenyl)-2-(methylamino)cyclohexanone hydrochloride is present in a concentration in the range of from about eq. 120 mg/mL to about eq. 250 mg/mL, based on the total volume of the pharmaceutical composition;
   wherein the pharmaceutical composition is administered as clusters of from 2 and up to 8 consecutive sprays within a time period of up to about 60 minutes, and wherein the patient is in need of treatment for depression, wherein the depression is major depressive disorder, and a therapeutically effective amount of the pharmaceutical composition is administered to alleviate one or more symptoms of the depression.

2. The method of claim 1, wherein the time period is from 1 to about 60 minutes.

3. The method of claim 1, wherein the major depressive disorder is treatment resistant depression.

4. The method of claim 1, wherein the pharmaceutical composition is administered once every couple of days.

5. The method of claim 3, wherein the pharmaceutical composition is administered once every couple of days.

6. The method of claim 1, wherein the (S)-2-(2-chlorophenyl)-2-(methylamino)cyclohexanone hydrochloride is present in a concentration in the range of from about eq. 120 mg/mL to about eq. 175 mg/mL, based on the total volume of the pharmaceutical composition.

7. The method of claim 1, wherein the (S)-2-(2-chlorophenyl)-2-(methylamino)cyclohexanone hydrochloride is present in a concentration in the range of from about eq. 125 mg/mL to about eq. 180 mg/mL, based on the total volume of the pharmaceutical composition.

8. The method of claim 1, wherein the (S)-2-(2-chlorophenyl)-2-(methylamino)cyclohexanone hydrochloride is present in a concentration in the range of from about eq. 125 mg/mL to about eq. 150 mg/mL, based on the total volume of the pharmaceutical composition.

9. The method of claim 1, wherein the (S)-2-(2-chlorophenyl)-2-(methylamino)cyclohexanone hydrochloride is present in a concentration in the range of from about eq. 140 mg/mL to about eq. 160 mg/mL, based on the total volume of the pharmaceutical composition.

10. The method of claim 1, wherein the (S)-2-(2-chlorophenyl)-2-(methylamino)cyclohexanone hydrochloride is present in a concentration of about eq. 140 mg/mL, based on the total volume of the pharmaceutical composition.

11. The method of claim 1, wherein the water content of the pharmaceutical composition is in the range of from 75 to 99.99 wt %, based on the total weight of the pharmaceutical composition.

12. The method of claim 1, wherein the pharmaceutical composition
   (i) additionally comprises one or more buffers; or
   (ii) has a pH value in the range of from about 3.5 to about 6.5.

13. The method of claim 12, wherein the pharmaceutical composition comprises the one or more buffers and has a pH value in the range of from about 4.0 to about 6.0.

14. The method of claim 13, wherein the one or more buffers is selected from the group consisting of citric acid, sodium dihydrogen phosphate, disodium hydrogen phosphate, acetic acid, boric acid, sodium borate, succinic acid, tartaric acid, malic acid, lactic acid, fumaric acid, and sodium hydroxide.

15. The method of claim 14, wherein the one or more buffers is selected from the group consisting of sodium hydroxide, citric acid, sodium dihydrogen phosphate, and disodium hydrogen phosphate.

16. The method of claim 15, wherein the buffer comprises citric acid or sodium hydroxide.

17. The method of claim 16, wherein the buffer comprises sodium hydroxide.

18. The method of claim 16, wherein the pH of the pharmaceutical composition is in the range of from about 4.0 to about 5.5.

19. The method of claim 18, wherein the pH of the pharmaceutical composition is in the range of from about 4.5 to about 5.0.

20. The method of claim 1, wherein the pharmaceutical composition further comprises a preservative.

21. The method of claim 20, wherein the preservative is selected from the group consisting of benzalkonium chloride, benzethonium chloride, benzoic acid, sodium benzoate, benzyl alcohol, bronopol, cetrimide, cetylpyridinium chloride, chlorhexidine, chlorbutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, sodium propionate, thimerosal, methyl paraben, ethyl paraben, propyl paraben, butyl paraben, isobutyl paraben, benzyl paraben, sorbic acid, and potassium sorbate, and mixtures thereof.

22. The method of claim 1, wherein the pharmaceutical composition does not contain a preservative.

23. The method of claim 1, wherein the pharmaceutical composition further comprises a penetrating agent.

24. The method of claim 23, wherein the penetrating agent is selected from the group consisting of tetradecyl maltoside, sodium glycocholate, tauroursodeoxycholic acid (TUDCA), lecithines, chitosan, benzalkonium chloride, sodium dodecyl sulfate, sodium docusate, polysorbates, laureth-9, oxtoxynol, sodium deoxycholate, polyarginine, and mixtures thereof.

25. The method of claim 14, wherein the pharmaceutical composition further comprises one or more additional excipients selected from the group consisting of a wetting agent, a surfactant, a solubilizing agent, a thickening agent, an isotonizing agent, a suspending agent, a colorant agent, and an antioxidant.

26. The method of claim 25, wherein the additional excipient is an antioxidant selected from the group consisting of a sulfite; ascorbic acid; an ascorbate; fumaric acid; ethylene diamine tetraacetic acid (EDTA) or its sodium or calcium salt; tocopherol; a gallate; vitamin E; and mixtures thereof.

27. The method of claim 25, wherein the additional excipient is a solubilizing agent selected from the group consisting of polyethylene glycol, glycerin, D-mannitol, trehalose, benzyl benzoate, ethanol, trisaminomethane, cholesterol, triethanolamine, sodium carbonate, sodium citrate, sodium salicylate, sodium acetate, and mixtures thereof.

28. The method of claim 25, wherein the additional excipient is an isotonizing agent selected from the group consisting of sodium chloride, glycerin, D-mannitol, D-sorbitol, glucose, and mixtures thereof.

29. The method of claim 25, wherein the additional excipient is a suspending agent selected from the group consisting of hydroxypropyl methylcellulose, sodium carmellose, microcrystalline cellulose, carbomer, pectin, sodium alginate, chitosan salts, gellan gum, poloxamer, polyvinyl pyrrolidone, xanthan gum, and mixtures thereof.

30. The method of claim 1, wherein the pharmaceutical composition further comprises an emulsifying agent selected from the group consisting of gelatin, cholesterol, acacia, tragacanth, pectin, methyl cellulose, carbomer, and mixtures thereof.

31. The method of claim 1, wherein the pharmaceutical composition further comprises a chelating agent.

32. The method of claim 31, wherein the chelating agent is EDTA, or its sodium or calcium salt.

33. The method of claim 1, wherein the (S)-2-(2-chlorophenyl)-2-(methylamino)cyclohexanone hydrochloride is present in a concentration in the range of from about eq. 140 mg/mL to about eq. 160 mg/mL, based on the total volume of the pharmaceutical composition, and the pharmaceutical composition further comprises citric acid, EDTA, and sodium hydroxide, wherein the pH of the pharmaceutical composition is in the range of from about 4.0 to about 5.5.

34. The method of claim 33, wherein the (S)-2-(2-chlorophenyl)-2-(methylamino)cyclohexanone hydrochloride is present in a concentration of about eq. 140 mg/mL.

35. The method of claim 33, wherein the pH of the pharmaceutical composition is about 4.5.

36. The method of claim 34, wherein the pH of the pharmaceutical composition is about 4.5.

37. The method of claim 3, wherein the (S)-2-(2-chlorophenyl)-2-(methylamino)cyclohexanone hydrochloride is present in a concentration in the range of from about eq. 140 mg/mL to about eq. 160 mg/mL, based on the total volume of the pharmaceutical composition, and the pharmaceutical composition further comprises citric acid, EDTA, and sodium hydroxide, wherein the pH of the pharmaceutical composition is about 4.0 to about 5.5.

38. The method of claim 37, wherein the (S)-2-(2-chlorophenyl)-2-(methylamino)cyclohexanone hydrochloride is present in a concentration of about eq. 140 mg/mL.

39. The method of claim 37, wherein the pH of the pharmaceutical composition is about 4.5.

40. The method of claim 38, wherein the pH of the pharmaceutical composition is about 4.5.

41. A method comprising:
intranasally administering to a human patient a pharmaceutical composition comprising (S)-2-(2-chlorophenyl)-2-(methylamino)cyclohexanone hydrochloride and water; wherein the (S)-2-(2-chlorophenyl)-2-(methylamino)cyclohexanone hydrochloride is present in a concentration in the range of from about 126 mg/mL to about 250 mg/mL, based on the total volume of the pharmaceutical composition;
wherein the pharmaceutical composition is administered as clusters of from 2 and up to 8 consecutive sprays within a time period of up to about 60 minutes, and
wherein the patient is in need of treatment for depression, wherein the depression is major depressive disorder, and a therapeutically effective amount of the pharmaceutical composition is administered to alleviate one or more symptoms of the depression.

42. The method of claim 41, wherein the time period is from 1 to about 60 minutes.

43. The method of claim 41, wherein the major depressive disorder is treatment resistant depression.

44. The method of claim 41, wherein the pharmaceutical composition is administered once every couple of days.

45. The method of claim 43, wherein the pharmaceutical composition is administered once every couple of days.

46. The method of claim 41, wherein the (S)-2-(2-chlorophenyl)-2-(methylamino)cyclohexanone hydrochloride is present in a concentration in the range of from about 126 mg/mL to about 162 mg/mL, based on the total volume of the pharmaceutical composition.

47. The method of claim 41, wherein the (S)-2-(2-chlorophenyl)-2-(methylamino)cyclohexanone hydrochloride is present in a concentration in the range of from about 150 mg/mL to about 200 mg/mL, based on the total volume of the pharmaceutical composition.

48. The method of claim 41, wherein the (S)-2-(2-chlorophenyl)-2-(methylamino)cyclohexanone hydrochloride is present in a concentration in the range of from about 150 mg/mL to about 175 mg/mL, based on the total volume of the pharmaceutical composition.

49. The method of claim 41, wherein the (S)-2-(2-chlorophenyl)-2-(methylamino)cyclohexanone hydrochloride is present in a concentration in the range of from about 160 mg/mL to about 163 mg/mL, based on the total volume of the pharmaceutical composition.

50. The method of claim 41, wherein the water content of the pharmaceutical composition is in the range of from 75 to 99.99 wt %, based on the total weight of the pharmaceutical composition.

51. The method of claim 41, wherein the pharmaceutical composition
   (i) additionally comprises one or more buffers; or
   (ii) has a pH value in the range of from about 3.5 to about 6.5.

52. The method of claim 51, wherein the pharmaceutical composition comprises the one or more buffers and has a pH value in the range of from about 4.0 to about 6.0.

53. The method of claim 52, wherein the one or more buffers is selected from the group consisting of citric acid, sodium dihydrogen phosphate, disodium hydrogen phosphate, acetic acid, boric acid, sodium borate, succinic acid, tartaric acid, malic acid, lactic acid, fumaric acid, and sodium hydroxide.

54. The method of claim 53, wherein the one or more buffers is selected from the group consisting of sodium hydroxide, citric acid, sodium dihydrogen phosphate, and disodium hydrogen phosphate.

55. The method of claim 54, wherein the buffer comprises citric acid or sodium hydroxide.

56. The method of claim 55, wherein the buffer comprises sodium hydroxide.

57. The method of claim 55, wherein the pH of the pharmaceutical composition is in the range of from about 4.0 to about 5.5.

58. The method of claim 57, wherein the pH of the pharmaceutical composition is in the range of from about 4.5 to about 5.0.

59. The method of claim 41, wherein the pharmaceutical composition further comprises a preservative.

60. The method of claim 59, wherein the preservative is selected from the group consisting of benzalkonium chloride, benzethonium chloride, benzoic acid, sodium benzoate, benzyl alcohol, bronopol, cetrimide, cetylpyridinium chloride, chlorhexidine, chlorbutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, sodium propionate, thimerosal, methyl paraben, ethyl paraben, propyl paraben, butyl paraben, isobutyl paraben, benzyl paraben, sorbic acid, and potassium sorbate, and mixtures thereof.

61. The method of claim 41, wherein the pharmaceutical composition does not contain a preservative.

62. The method of claim 41, wherein the pharmaceutical composition further comprises a penetrating agent.

63. The method of claim 62, wherein the penetrating agent is selected from the group consisting of tetradecyl maltoside, sodium glycocholate, tauroursodeoxycholic acid (TUDCA), lecithines, chitosan, benzalkonium chloride, sodium dodecyl sulfate, sodium docusate, polysorbates, laureth-9, oxtoxynol, sodium deoxycholate, polyarginine, and mixtures thereof.

64. The method of claim 53, wherein the pharmaceutical composition further comprises one or more additional excipients selected from the group consisting of a wetting agent, a surfactant, a solubilizing agent, a thickening agent, an isotonizing agent, a suspending agent, a colorant agent, and an antioxidant.

65. The method of claim 64, wherein the additional excipient is an antioxidant selected from the group consisting of a sulfite; ascorbic acid; an ascorbate; fumaric acid; ethylene diamine tetraacetic acid (EDTA) or its sodium or calcium salt; tocopherol; a gallate; vitamin E; and mixtures thereof.

66. The method of claim 64, wherein the additional excipient is a solubilizing agent selected from the group consisting of polyethylene glycol, glycerin, D-mannitol, trehalose, benzyl benzoate, ethanol, trisaminomethane, cholesterol, triethanolamine, sodium carbonate, sodium citrate, sodium salicylate, sodium acetate, and mixtures thereof.

67. The method of claim 64, wherein the additional excipient is an isotonizing agent selected from the group consisting of sodium chloride, glycerin, D-mannitol, D-sorbitol, glucose, and mixtures thereof.

68. The method of claim 64, wherein the additional excipient is a suspending agent selected from the group consisting of hydroxypropyl methylcellulose, sodium carmellose, microcrystalline cellulose, carbomer, pectin, sodium alginate, chitosan salts, gellan gum, poloxamer, polyvinyl pyrrolidone, xanthan gum, and mixtures thereof.

69. The method of claim 41, wherein the pharmaceutical composition further comprises an emulsifying agent selected from the group consisting of gelatin, cholesterol, acacia, tragacanth, pectin, methyl cellulose, carbomer, and mixtures thereof.

70. The method of claim 41, wherein the pharmaceutical composition further comprises a chelating agent.

71. The method of claim 70, wherein the chelating agent comprises EDTA, or its sodium or calcium salt.

72. The method of claim 41, wherein the (S)-2-(2-chlorophenyl)-2-(methylamino)cyclohexanone hydrochloride is present in a concentration in the range of from about 160 mg/mL to about 163 mg/mL, based on the total volume of the pharmaceutical composition, and the pharmaceutical composition further comprises citric acid, EDTA, and sodium hydroxide, wherein the pH of the pharmaceutical composition is in the range of from about 4.0 to about 5.5.

73. The method of claim 72, wherein the pH of the pharmaceutical composition is about 4.5.

74. The method of claim 43, wherein the (S)-2-(2-chlorophenyl)-2-(methylamino)cyclohexanone hydrochloride is present in a concentration in the range of from about 160 mg/mL to about 163 mg/mL, based on the total volume of the pharmaceutical composition, and the pharmaceutical composition further comprises citric acid, EDTA, and sodium hydroxide, wherein the pH of the pharmaceutical composition is in the range of from about 4.0 to about 5.5.

75. The method of claim 74, wherein the pH of the pharmaceutical composition is about 4.5.

* * * * *